(12) United States Patent
Golemis et al.

(10) Patent No.: US 6,653,074 B1
(45) Date of Patent: Nov. 25, 2003

(54) METHODS FOR IDENTIFYING AGENTS WHICH AFFECT CELLULAR MORPHOLOGY, LOCOMOTION AND DEATH

(75) Inventors: Erica A. Golemis, Oreland, PA (US); Geraldine O'Neill, Philadelphia, PA (US); Sarah Fashena, Jenkintown, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 107 days.

(21) Appl. No.: 09/669,459

(22) Filed: Sep. 25, 2000

Related U.S. Application Data

(60) Continuation-in-part of application No. 09/196,466, filed on Nov. 19, 1998, which is a continuation of application No. 08/968,633, filed on Nov. 12, 1997, now Pat. No. 6,100,384, which is a division of application No. 08/491,357, filed on Jun. 30, 1995, now Pat. No. 5,716,782.

(51) Int. Cl.[7] .......................... C12Q 1/68; C12P 19/34; C12N 15/64; C07H 21/02; C07H 21/04
(52) U.S. Cl. .................. 435/6; 435/91.1; 435/91.42; 536/23.1
(58) Field of Search .................. 536/23.1; 435/91.1, 435/91.42, 6

(56) References Cited

FOREIGN PATENT DOCUMENTS

WO            WO 97/02362       *   1/1997

OTHER PUBLICATIONS

Parker, et al., 1989, Virology, 173:664–673.*
Adams et al., 1992, Oncogene 7:611–618.
Altschul et al., 1990, J. Mol. Bio. 215:403–410.
Bear et al., 1989, Proc. Natl. Acad. Sci. USA 86:7495–7499.
Blacketer et al., 1993, Mol. Cell Biol. 13:5567–5581.
Sakai et al., 1994, EMBO J. 13:3748–3756.
Brent and Ptashne, 1985, Cell 57:1045–1052.
Devereux et al., 1984, Nucl. Acids Res. 12:387–397.
DiPersio et al., 1991, Mol. Cell Biol. 11:4405–4414.
Eva and Aaronson, 1985, Nature 316:273–275.
Gilks et al., 1993, Mol. Cell Biol. 13:1759–1768.
Gimeno et al., 1992, Cell 68:1077–1090.
Gimeno and Fink, 1994, Mol. Cell Biol. 14:2100–2112.
Golemis and Brent, 1992, Mol. Cell Biol. 12:3006–3014.
Gyuris et al., 1993, Cell 75:791–803.
Liu et al., 1993, Science 262:1741–1744.
McCormick, 1993, Nature 363:15–16.
Samson et al., 1989, Cell 57:1045–1052.
Ridley and Hall, 1992, Cell 70:389–399.
Ridley et al., 1992, Cell 70:401–410.
Ron et al., 1988, EMBO J. 7:2465–2473.

* cited by examiner

*Primary Examiner*—Anthony C. Caputa
*Assistant Examiner*—Natalie Davis
(74) *Attorney, Agent, or Firm*—Dann, Dorfman, Herrell and Skillman

(57) ABSTRACT

An isolated nucleic acid molecule is provided which encodes a mammalian signal mediator protein, HEF-1, involved in regulation of cellular morphological alterations. The encoded protein comprises an amino-terminal SH3 domain, an internal domain containing several SH2 binding motifs, and a carboxy-terminal effector domain that can induce pseudohyphal budding in yeast. The invention also provides the novel signal mediator protein, and antibodies thereto. These biological molecules are useful as research tools and as diagnostic and therapeutic agents in methods for the identification, detection and regulation of complex signaling events leading to morphological, potentially neoplastic, cellular changes.

4 Claims, 22 Drawing Sheets

```
accccacgctaccgaaATGAAGTATAAGAATCTTATGGCAAGGGCCTTATATGACAAT
                 M  K  Y  K  N  L  M  A  R  A  L  Y  D  N
GTCCCAGAGTGTGCCGAGGAACTGGCCTTTCGCAAGGGAGACATCCTGACCGTCATAGAG
 V  P  E  C  A  E  E  L  A  F  R  K  G  D  I  L  T  V  I  E
CAGAACACAGGGGGACTGGAAGGATGGTGGCTGTGCTCGTTACACGGTCGGCAAGGCATT
 Q  N  T  G  G  L  E  G  W  W  L  C  S  L  H  G  R  Q  G  I
GTCCCAGGCAACCGGGTGAAGCTTCTGATTGGCCCCATGCAGGAGACTGCCTCCAGTCAC
 V  P  G  N  R  V  K  L  L  I  G  P  M  Q  E  T  A  S  S  H
GAGCAGCCTGCCTCTGGACTGATGCAGCAGACCTTTGGCCAACAGAAGCTCTATCAAGTG
 E  Q  P  A  S  G  L  M  Q  Q  T  F  G  Q  Q  K  L  Y  Q  V
CCAAACCCACAGGCTGCTCCCCGAGACACTATCTACCAAGTGCCACCTTCCTACCAAAAT
 P  N  P  Q  A  A  P  R  D  T  I  Y  Q  V  P  P  S  Y  Q  N
CAGGGAATTTACCAAGTCCCCACTGGCCACGGCACCCAAGAACAAGAGGTATATCAGGTG
 Q  G  I  Y  Q  V  P  T  G  H  G  T  Q  E  Q  E  V  Y  Q  V
CCACCATCAGTGCAGAGAAGCATTGGGGGAACCAGTGGGCCCCACGTGGGTAAAAAGGTG
 P  P  S  V  Q  R  S  I  G  G  T  S  G  P  H  V  G  K  K  V
ATAACCCCCGTGAGGACAGGCCATGGCTACGTATACGAGTACCCATCCAGATACCAAAAG
 I  T  P  V  R  T  G  H  G  Y  V  Y  E  Y  P  S  R  Y  Q  K
GATGTCTATGATATCCCTCCTTCTCATACCACTCAAGGGGTATACGACATCCCTCCCTCA
 D  V  Y  D  I  P  P  S  H  T  T  Q  G  V  Y  D  I  P  P  S
TCAGCAAAAGGCCCTGTGTTTTCAGTTCCAGTGGGAGAGATAAAACCTCAAGGGGTGTAT
 S  A  K  G  P  V  F  S  V  P  V  G  E  I  K  P  Q  G  V  Y
GACATCCCGCCTACAAAAGGGGTATATGCCATTCCGCCCTCTGCTTGCCGGGATGAAGCA
 D  I  P  P  T  K  G  V  Y  A  I  P  P  S  A  C  R  D  E  A
GGGCTTAGGGAAAAAGACTATGACTTCCCCCCTCCCATGAGACAAGCTGGAAGGCCGGAC
 G  L  R  E  K  D  Y  D  F  P  P  P  M  R  Q  A  G  R  P  D
CTCAGACCGGAGGGGGTTTATGACATTCCTCCAACCTGCACCAAGCCAGCAGGGAAGGAC
 L  R  P  E  G  V  Y  D  I  P  P  T  C  T  K  P  A  G  K  D
CTTCATGTAAAATACAACTGTGACATTCCAGGAGCTGCAGAACCGGTGGCTCGAAGGCAC
```

Figure 1A

```
L   H   V   K   Y   N   C   D   I   P   G   A   A   E   P   V   A   R   R   H
CAGAGCCTGTCCCCGAATCACCCACCCCCGCAACTCGGACAGTCAGTGGGCTCTCAGAAC
Q   S   L   S   P   N   H   P   P   P   Q   L   G   Q   S   V   G   S   Q   N
GACGCATATGATGTCCCCCGAGGCGTTCAGTTTCTTGAGCCACCAGCAGAAACCAGTGAG
D   A   Y   D   V   P   R   G   V   Q   F   L   E   P   P   A   E   T   S   E
AAAGCAAACCCCCAGGAAAGGGATGGTGTTTATGATGTCCCTCTGCATAACCCGCCAGAT
K   A   N   P   Q   E   R   D   G   V   Y   D   V   P   L   H   N   P   P   D
GCTAAAGGCTCTCGGGACTTGGTGGATGGGATCAACCGATTGTCTTTCTCCAGTACAGGC
A   K   G   S   R   D   L   V   D   G   I   N   R   L   S   F   S   S   T   G
AGCACCCGGAGTAACATGTCCACGTCTTCCACCTCCTCCAAGGAGTCCTCACTGTCAGCC
S   T   R   S   N   M   S   T   S   S   T   S   S   K   E   S   S   L   S   A
TCCCCAGCTCAGGACAAAAGGCTCTTCCTGGATCCAGACACAGCTATTGAGAGACTTCAG
S   P   A   Q   D   K   R   L   F   L   D   P   D   T   A   I   E   R   L   Q
CGGCTCCAGCAGGCCCTTGAGATGGGTGTCTCCAGCCTAATGGCACTGGTCACTACCGAC
R   L   Q   Q   A   L   E   M   G   V   S   S   L   M   A   L   V   T   T   D
TGGCGGTGTTACGGATATATGGAAAGACACATCAATGAAATACGCACAGCAGTGGACAAG
W   R   C   Y   G   Y   M   E   R   H   I   N   E   I   R   T   A   V   D   K
GTGGAGCTGTTCCTGAAGGAGTACCTCCACTTTGTCAAGGGAGCTGTTGCAAATGCTGCC
V   E   L   F   L   K   E   Y   L   H   F   V   K   G   A   V   A   N   A   A
TGCCTCCCGGAACTCATCCTCCACAACAAGATGAAGCGGGAGCTGCAACGAGTCGAAGAC
C   L   P   E   L   I   L   H   N   K   M   K   R   E   L   Q   R   V   E   D
TCCCACCAGATCCTGAGTCAAACCAGCCATGACTTAAATGAGTGCAGCTGGTCCCTGAAT
S   H   Q   I   L   S   Q   T   S   H   D   L   N   E   C   S   W   S   L   N
ATCTTGGCCATCAACAAGCCCCAGAACAAGTGTGACGATCTGGACCGGTTTGTGATGGTG
I   L   A   I   N   K   P   Q   N   K   C   D   D   L   D   R   F   V   M   V
GCAAAGACGGTGCCCGATGACGCCAAGCAGCTCACCACAACCATCAACACCAACGCAGAG
A   K   T   V   P   D   D   A   K   Q   L   T   T   T   I   N   T   N   A   E
GCCCTCTTCAGACCCGGCCCTGGCAGCTTGCATCTGAAGAATGGGCCGGAGAGCATCATG
A   L   F   R   P   G   P   G   S   L   H   L   K   N   G   P   E   S   I   M
```

Figure 1B

```
AACTCAACGGAGTACCCACACGGTGGCTCCCAGGGACAGCTGCTGCATCCTGGTGACCAC
 N  S  T  E  Y  P  H  G  G  S  Q  G  Q  L  L  H  P  G  D  H

AAGGCCCAGGCCCACAACAAGGCACTGCCCCCAGGCCTGAGCAAGGAGCAGGCCCCTGAC
 K  A  Q  A  H  N  K  A  L  P  P  G  L  S  K  E  Q  A  P  D

TGTAGCAGCAGTGATGGTTCTGAGAGGAGCTGGATGGATGACTACGATTACGTCCACCTA
 C  S  S  S  D  G  S  E  R  S  W  M  D  D  Y  D  Y  V  H  L

CAGGGTAAGGAGGAGTTTGAGAGGCAACAGAAAGAGCTATTGGAAAAAGAGAATATCATG
 Q  G  K  E  E  F  E  R  Q  Q  K  E  L  L  E  K  E  N  I  M

AAACAGAACAAGATGCAGCTGGAACATCATCAGCTGAGCCAGTTCCAGCTGTTGGAACAA
 K  Q  N  K  M  Q  L  E  H  H  Q  L  S  Q  F  Q  L  L  E  Q

GAGATTACAAAGCCCGTGGAGAATGACATCTCGAAGTGGAAGCCCTCTCAGAGCCTACCC
 E  I  T  K  P  V  E  N  D  I  S  K  W  K  P  S  Q  S  L  P

ACCACAAACAGTGGCGTGAGTGCTCAGGATCGGCAGTTGCTGTGCTTCTACTATGACCAA
 T  T  N  S  G  V  S  A  Q  D  R  Q  L  L  C  F  Y  Y  D  Q

TGTGAGACCCATTTCATTTCCCTTCTCAACGCCATTGACGCACTCTTCAGTTGTGTCAGC
 C  E  T  H  F  I  S  L  L  N  A  I  D  A  L  F  S  C  V  S

TCAGCCCAGCCCCCGCGAATCTTCGTGGCACACAGCAAGTTTGTCATCCTCAGTGCACAC
 S  A  Q  P  P  R  I  F  V  A  H  S  K  F  V  I  L  S  A  H

AAACTGGTGTTCATTGGAGACACGCTGACACGGCAGGTGACTGCCCAGGACATTCGCAAC
 K  L  V  F  I  G  D  T  L  T  R  Q  V  T  A  Q  D  I  R  N

AAAGTCATGAACTCCAGCAACCAGCTCTGCGAGCAGCTCAAGACTATAGTCATGGCAACC
 K  V  M  N  S  S  N  Q  L  C  E  Q  L  K  T  I  V  M  A  T

AAGATGGCCGCCCTCCATTACCCCAGCACCACGGCCCTGCAGGAAATGGTGCACCAAGTG
 K  M  A  A  L  H  Y  P  S  T  T  A  L  Q  E  M  V  H  Q  V

ACAGACCTTTCTAGAAATGCCCAGCTGTTCAAGCGCTCTTTGCTGGAGATGGCAACGTTC
 T  D  L  S  R  N  A  Q  L  F  K  R  S  L  L  E  M  A  T  F

TGAGAAGAAAAAAAAGAGGAAGGGGACTGCGTTAACGGTTACTAAGGAAAACTGGAAATA

CTGTCTGGTTTTTGTAAATGTTATCTATTTTTGTAGATAATTTTTATATAAAAATGAAATA
TTTTAACATTTTATGGGTCAGACAACTTTCAGAAATTCAGGGAGCTGGAGAGGGAAATCT
TTTTTTCCCCCCTGAGTXGTTCTTATGTATACACAGAAGTATCTGAGACATAAACTGTAC
AGAAAACTTGTCCACGTCCTTTTGTATGCCCATGTATTCATGTTTTTGTTTGTAGATGTT
```

```
HEF1      LSQFQLLEQEITKPVENDISKWKPSQSL.PTTNSGV AQDROLLCFYYDQCETHFISL
MEF1      LSQFQLLEQEITKPVENDISKWKPSQSL.PTTNNSV AQDROLLCFYYDQCETHFISL
p130cas   LKQFERLEQEVSRPIDHDLANWTPAQPLVPGRTGGLGPSDRQLLLFYLEQCEANLTTL HEF1      LNAIDALFSCVSSAQPPRIFV
MEF1      LNAIDALFSCVSSAQPPRIFV
p130cas   TDAVDAFFTAVATNQPPKIFV
```

Figure 3

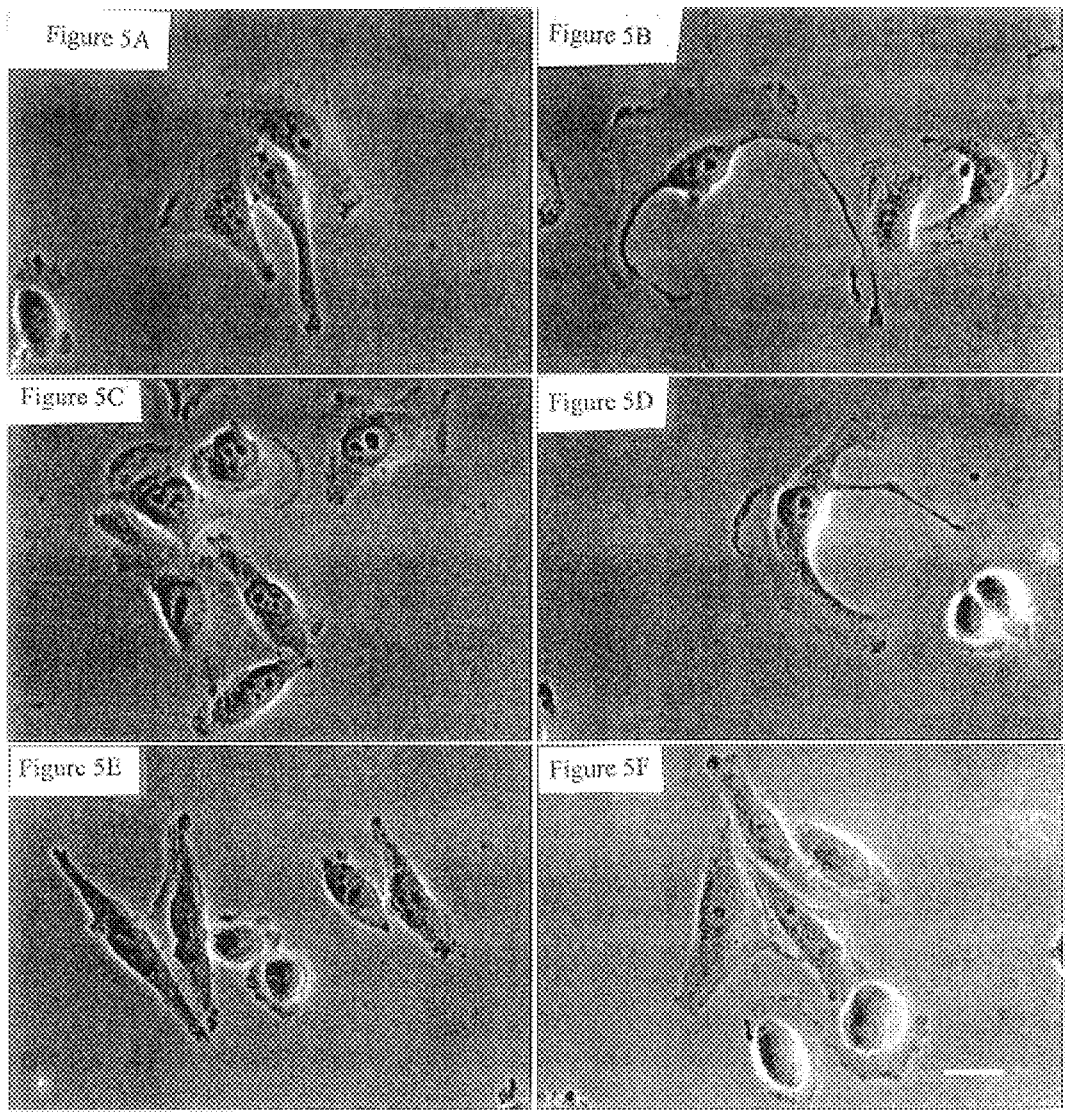

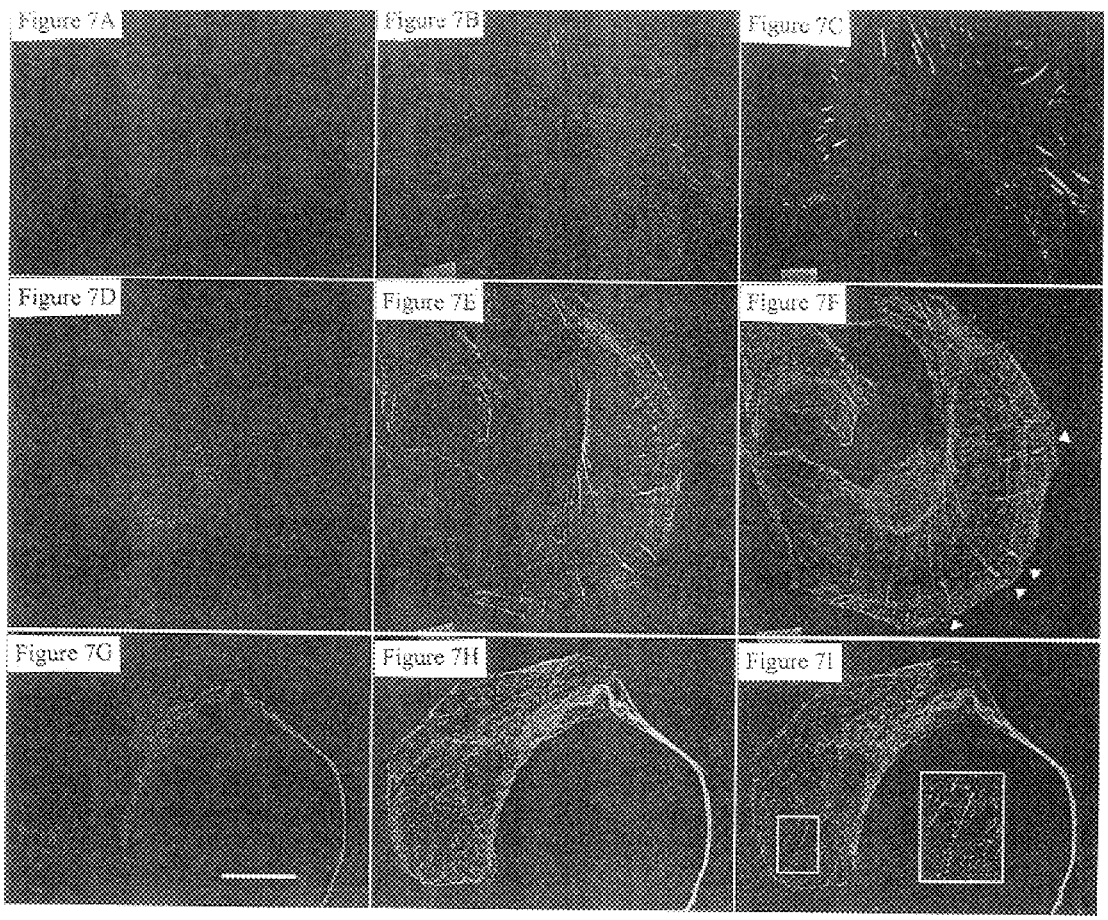

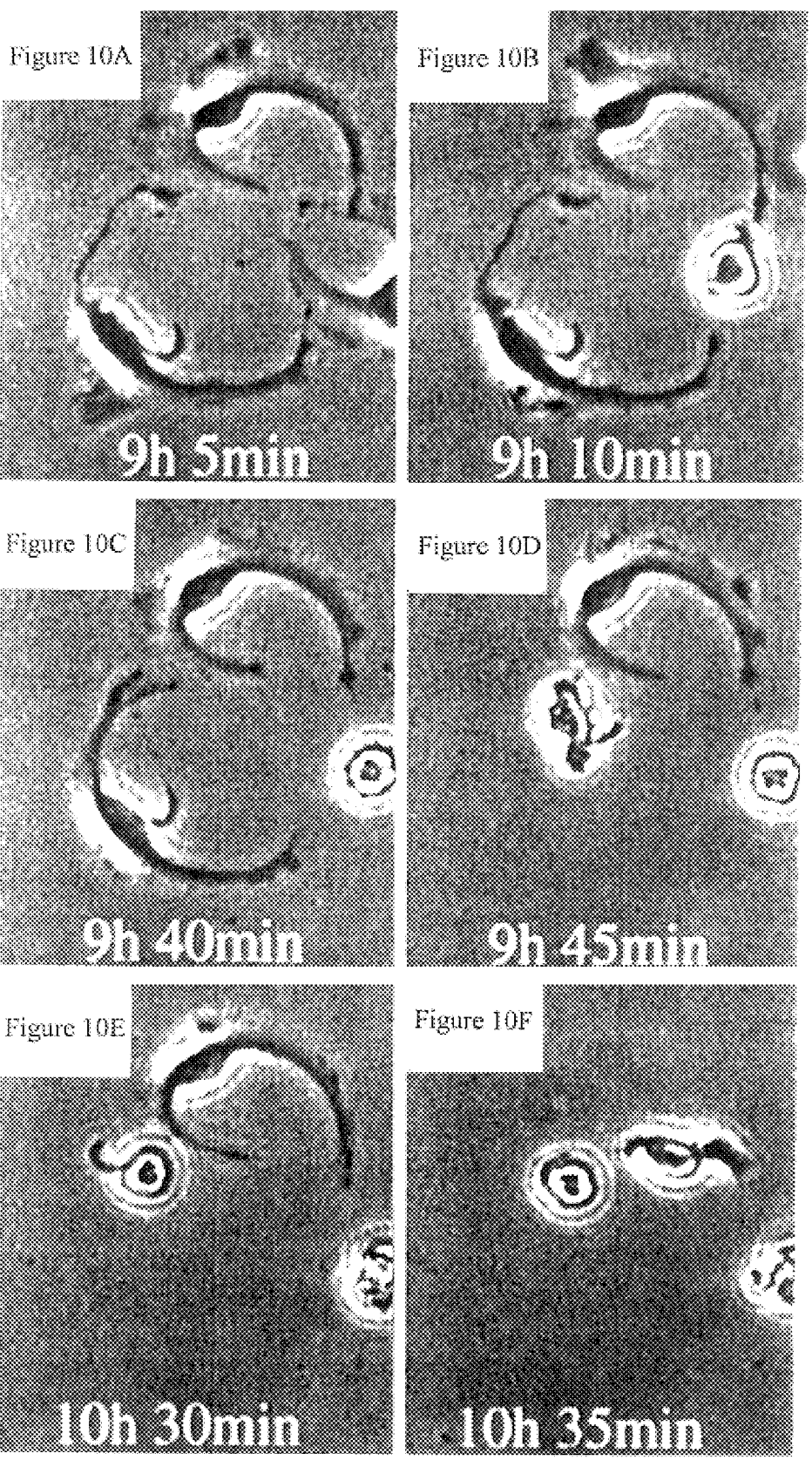

METHODS FOR IDENTIFYING AGENTS WHICH AFFECT CELLULAR MORPHOLOGY, LOCOMOTION AND DEATH

This application is a continuation-in-part of U.S. application Ser. No. 09/196,466, filed Nov. 19, 1998, which is a continuation of Ser. No. 08/968,633, now U.S. Pat. No. 6,100,384, filed Nov. 12, 1997, which is a divisional of Ser. No. 08/491,357, now U.S. Pat. No. 5,716,782, filed Jun. 30, 1995, the entirety of which is incorporated by reference herein.

Pursuant to 35 U.S.C. §202(c), it is hereby acknowledged that the U.S. Government has certain rights in the invention described herein, which was made in part with funds from the National Institutes of Health, Grant Nos:RO1CA63366, CA-06927 and T32 CA09035.

FIELD OF THE INVENTION

This invention relates to diagnosis and treatment of neoplastic diseases. More specifically, this invention provides methods useful for identifying agents which affect the complex signaling events involved in motility, morphological and potentially neoplastic cellular changes, including apoptotic cell death.

BACKGROUND OF THE INVENTION

Various scientific and scholarly articles are cited throughout the specification. These articles are incorporated by reference herein to describe the state of the art to which this invention pertains.

Cellular transformation during the development of cancer involves multiple alterations in the normal pattern of cell growth regulation. Primary events in the process of carcinogenesis involve the activation of oncogene function by some means (e.g., amplification, mutation, chromosomal rearrangement), and in many cases, the removal of anti-oncogene function. In the most malignant and untreatable tumors, normal restraints on cell growth are completely lost as transformed cells escape from their primary sites and metastasize to other locations in the body. One reason for the enhanced growth and invasive properties of some tumors may be the acquisition of increasing numbers of mutations in oncogenes, with cumulative effect (Bear et al., Proc. Natl. Acad. Sci. USA 86:7495–7499, (1989)). Alternatively, insofar as oncogenes function through the normal cellular signaling pathways required for organismal growth and cellular function (reviewed in McCormick, Nature 363:15–16, (1993)), additional events corresponding to mutations or deregulation in the oncogenic signaling pathways may also contribute to tumor malignancy (Gilks et al., Mol. Cell Biol. 13:1759–1768, (1993)), even though mutations in the signaling pathways alone may not cause cancer.

Several discrete classes of proteins are known to be involved in bringing about the different types of changes in cell division properties and morphology associated with transformation. These changes can be summarized as, first, the promotion of continuous cell cycling (immortalization); second, the loss of responsiveness to growth inhibitory signals and cell apoptotic signals; and third, the morphological restructuring of cells to enhance invasive properties.

Of these varied mechanisms of oncogene action, the role of control of cell morphology is one of the least understood. Research using non-transformed mammalian cells in culture has demonstrated that simply altering the shape of a cell can profoundly alter its pattern of response to growth signals (DiPersio et al., Mol. Cell Biol. 11:4405–4414, (1991)), implying that control of cell shape may actually be causative of, rather than correlative to, cell transformation. For example, mutation of the antioncogene NF2 leads to development of nervous system tumors. Higher eucaryotic proteins involved in promoting aberrant morphological changes related to cancer may mediate additional functions in normal cells that are not obviously related to the role they play in cancer progression, complicating their identification and characterization.

Recent evidence suggests that certain key proteins involved in control of cellular morphology contain conserved domains referred to as SH2 and SH3 domains. These domains consist of non-catalytic stretches of approximately 50 amino acids (SH3) and 100 amino acids (SH2, also known as the "Src homology domain"). SH2/SH3 domains are found in cytoskeletal components, such as actin, and are also found in signaling proteins such as Abl. The interaction of these proteins plays a critical role in organizing cytoskeleton-membrane attachments.

Besides the numerous SH2/SH3-containing molecules with known catalytic or functional domains, there are several signaling molecules, called "adapter proteins," which are so small that no conserved domains seem to exist except SH2 and SH3 domains. Oncoproteins such as Nck, Grb2/Ash/SEM5 and Crk are representatives of this family. The SH2 regions of these oncoproteins bind specific phosphotyrosine-containing proteins by recognizing a phosphotyrosine in the context of several adjacent amino acids. Following recognition and binding, specific signals are transduced in a phosphorylation dependent manner.

As another example, P47v-Crk (CrK) is a transforming gene from avian sarcoma virus isolate CT10. This protein contains one SH2 and one SH3 domain, and induces an elevation of tyrosine phosphorylation on a variety of downstream targets. One of these targets, p130cas, is tightly associated with v-Crk. The SH2 domain of v-Crk is required for this association and subsequent cellular transformation. P130cas is also a substrate for Src mediated phosphorylation. Judging from its structure, p130cas may function as a "signal assembler" of Src family kinases and several cellular SH2-containing proteins. These proteins bind to the SH2 binding domain of p130cas, which is believed to induce a conformational change leading to the activation and inactivation of downstream signals, modulated by multiple domains of the protein.

Another oncogene, Ras, is a member of a large evolutionarily conserved superfamily of small GTP-binding proteins responsible for coordinating specific growth factor signals with specific changes in cell shape, including the development of stress fibers and membrane ruffles (Ridley and Hall, Cell 70:389–399, 1992; Ridley et al., Cell 70:401–410,(1992)). A rapidly growing family of oncoproteins, including Vav, Bcr, Ect-2, and Dbl, has been found to be involved in a variety of different tumors (Eva and Aaronson, Nature 316:273–275, (1985); Ron et al., EMBO J. 7:2465–2473, (1988); Adams et al., Oncogene 7:611–618, (1992); Miki et al., Nature 362:462–465, (1993)). Proteins of this family have been shown to interact with Ras/Rac/Rho family members, and possess sequence characteristics that suggest they too directly associate with and modulate organization of the cytoskeleton.

In view of the significant relationship between signaling or "adapter" proteins, altered cellular morphology and the development of cancer, it would be of clear benefit to identify and isolate such proteins (or genes encoding them) for the purpose of developing diagnostic/therapeutic agents for the treatment of cancer.

SUMMARY OF THE INVENTION

It is an object of the present invention to provide a purified nucleic acid molecule of human origin that encodes a signal mediator protein (SMP) also known as HEF-1, involved in the signaling cascade related to morphological cellular changes, and therefrom provide isolated and purified protein for use in methods for identifying beneficial therapeutic agents which regulate these signaling cascades. Such methods facilitate the identification and characterization of other genes and proteins involved in regulating cellular morphology, division and death.

HEF-1 is encoded by SEQ ID NO: 1 and is described and claimed in U.S. Pat. No. 5,716,782. The amino acid sequence of HEF-1 is provided in SEQ ID NO:2 and is described and claimed in U.S. application Ser. No. 09/196, 466. Antibodies immunologically specific for HEF-1 are disclosed in U.S. Pat. No. 6,100,384. All of the foregoing patents and patent applications are incorporated by reference herein in their entirety.

In accordance with the present invention, HEF-1 has been implicated in a variety of fundamental biological processes. These include, apoptosis, T cell and epithelial cell migration, and cell spreading. Various assays are provided herein for identifying therapeutic agents which regulate these processes.

Thus, in one embodiment of the invention, methods are provided for identifying test compounds which regulate apoptosis mediated by HEF1. An exemplary method involves incubating HEF1 overexpressing cells in the presence of a test compound suspected of having apoptotic regulatory activity relative to untreated controls and assessing whether the test compound alters the number of cells undergoing programmed cell death. Cell death may be assessed by a variety of methods, including without limitation, trypan blue assay, MTT assay, propridium iodide uptake, DNA fragmentation or laddering, alterations in cellular morphology and the generation of caspase cleavage products.

In another embodiment of the invention, methods are provided for identifying test compounds which affect cellular motility. An exemplary method involves incubating HEF1 overexpressing cells in the presence of a test compound suspected of having motility regulating activity relative to untreated controls and assessing whether the test compound impedes or promotes cellular motility. Cellular motility or migration may be assessed using a variety of techniques which include without limitation, Boyden two chamber assays and quantitation using Isee® imaging software.

In a further embodiment of the invention, methods are provided for determining whether germline or somatic cell samples from patients contain altered HEF1 encoding nucleic acids. Such methods include without limitation, SSCP, direct sequencing, and heteroduplex formation followed by cleavage by mismatch recognizing enzymes followed by electrophoresis.

In a final embodiment, kits for performing the foregoing methods are also provided.

BRIEF DESCRIPTION OF THE DRAWINGS

FIG. 1. Nucleotide sequence (Sequence I.D. No. 1) and deduced amino acid sequence (Sequence I.D. No. 2) of HEF1, a cDNA of human origin encoding an exemplary signal mediator protein of the invention.

FIG. 2. Amino acid sequence alignment of the deduced amino acid sequence of HEF1 (Sequence I.D. No. 2) with homologous sequences of p130cas from rat (Sequence I.D. No 3). Boxes represent regions of sequence identity between the two proteins. The closed circle marks the site of the initial methionine in the truncated clone of HEF1. The thick underline denotes the conserved SH3 domain. Tyrosines are marked with asterisks.

FIG. 3. Amino acid sequence alignment of the carboxy-terminal regions of HEF1-encoded hSMP with p130cas and the mouse homolog of hSMP, mSMP encoded by MEF1 (Sequence I.D. No. 4).

FIG. 4A: HEF1 expression is induced following removal of tetracycline. MCF7 cells were transfected with a plasmid encoding the tTA transactivator and a tetracycline-regulatable expression plasmid either without (control vector; CM 1) or with a HEF1 cDNA insert (HEF1.M1* and HEF1.M2). Total cell lysates (35 $\mu$g) derived from uninduced (Lanes 1, 3, 5) or induced/mock induced (Lanes 2, 4, 6) clones were processed by immunoblotting with anti-HEF1-SB-R1 antisera to assess HEF1 expression levels. FIG. 4B: The kinetics of HEF1 expression. Lysates (30 $\mu$g) were isolated from HEF.M1 cells induced to express HEF1 for the indicated time intervals (in hours, labeled above each lane). Negative controls include lysates isolated after 24 hours from uninduced HEF1.M1 (Lane 1) or mock induced CM1 cells (Lane 9).

FIGS. 5A–5F. A series of micrographs showing HEF1 induces a morphological conversion to crescent-shaped cells. HEF1.M1 (A and B), HEF1.M2 (C and D), and CM1 (E and F) cells were either uninduced (A, C, E) or induced/mock induced (B, D, F) for HEF1 expression. Expression of HEF1 caused dramatic morphological changes in HEF1.M1 (B) and HEF1.M2 (D) cells as compared to experimentally matched uninduced HEF1.M1 (A) and HEF1.M2 (C) cells. Morphological changes were not apparent in mock induced CM1 cells (compare panels E and F). Phase contrast CCD images were acquired with a 40× objective. Size bar equals approximately 25 $\mu$m.

FIG. 6K: a graph showing quantitation of increased cell spreading. HEF1.M1 or CM1 cells maintained for 18 hours in either non-inducing (−) or inducing (+) conditions were replated on glass coverslips either uncoated in the presence of 10% FBS (shaded) or coated with human FN in serum free media (black). The cells were fixed at 6 hours after replating. Cells were maintained in inducing or non-inducing conditions for the duration of the experiment. CCD images were acquired with a 40× objective (8–10 fields per condition) and the area was determined by outlining each cell utilizing Inovision ISEE™ software. Approximately eight fields per condition were quantitated. Results shown are the mean of three independent experiments +/− standard error.

FIGS. 7A–7I. A series of immunofluorescent micrographs showing that HEF1 localizes to prominent focal adhesion sites and the trailing edge. Immunofluorescent staining of either uninduced (FIG. 7A) or induced (FIGS. 7B–7I), HEF1.M1 cells was performed using antisera specific for HEF1 (FIGS. 7A, 7B, 7D, 7F, 7G, 7I), antibodies specific for paxillin (FIG. 7C) or tubulin (FIG. 7H), or phalloidin stained F-actin (FIG. 7E). Merged images show HEF1/F-actin (FIG. 7F) and HEF1/tubulin (FIG. 7I) staining. Expression of HEF1 induced a morphological conversion to a crescent-shaped cell (compare FIG. 7B to FIG. 7A). Note the pronounced colocalization of HEF1 and paxillin to the prominent focal adhesion sites in the leading edge lamellipodia (compare FIG. 7B to FIG. 7C). Double label immunofluorescence revealed colocalization of HEF1 to the distal ends of F-actin rich stress fibers (FIG. 7F, arrowheads). The microtubule network was most prominent in the perinuclear region and trailing edge (FIG. 7H), at which sites HEF1 staining coincided (FIG. 7G, FIG. 7I). Note also the colocalization of HEF1 and tubulin at focal adhesion sites (FIG. 7I, inset box, −300% enlargement). Indirect inununofluorescence using HEF1 antibodies alone confirmed that HEF1 was concentrated both at focal adhesion sites and in the trailing edge (data not shown). Images depict 1.4 micron sections, acquired using a Bio-Rad MRC 600 confocal microscope (60× objective). Scale bar equals approximately 25 $\mu$m.

(FIG. 9A) A graphic representation of the average speed of uninduced (shaded bars) or induced (solid bars) HEF1.M1 cells grouped into speed ranges is depicted. (FIG. 9B) A similar graphic representation of the average speed of uninduced (shaded bars) or mock induced (solid bars) CM1 cells grouped into speed ranges revealed that the speed of CM1 cells was not altered by mock induction. These data represent the average speed of HEF1.M1 cells (uninduced, N=59; induced, N=55) and CM1 cells (uninduced, N=76; mock induced, N=60) derived from two independent experiments.

FIG. 10. Prolonged expression of HEF1 induces phenotypic changes that contribute to cell death. Three late stage crescents in a HEF1.M1 population are shown in a time lapse image (FIG. 10A) and their progression followed by additional images acquired at the later indicated times (FIGS. 10B–10F) post-induction of HEF1.

FIG. 12A. Lysates from a HEF1 cell line and a control vector cell line were prepared from cells grown for 48 hours in one of the following conditions: induced, non-induced and noninduced in the presence of TNF-α. Western blots, of total cell lysates were probed with antibodies to HEF1 (α-HEF1/1) and to PARP (α-PARP). FIG. 12B. HEf1-expressing cells and vector control cells were grown for 48 hours under inducing or non-inducing conditions. Lysates were then incubated with Ac-DEVD-pNA (250 $\mu$M) for 24 hours. Formation of product was monitored at 405 nm in the absence or presence of the caspase 3 inhibitory peptide z-DEVD-fmk (0.5 $\mu$M, final concentration), as indicated. Experiments were repeated at least three times and shown is a representative experiment. Error bars represent the standard error of triplicate samples.

FIG. 13A. MCF-7 cells treated with 100 ng/ml TNF-α. FIG. 13B. MCF-7 cells treated with 100 ng/ml TNF-α in the presence or absence of the caspase 3 inhibitory peptide z-DEVD-fmk at a final concentration of 25 nM. FIG. 13C. WEHI231 cells were treated with 1 $\mu$g/ml α-IgM antibodies and extracted at the indicated times. Total proteins were extracted at the indicated timepoints and Western blots were probed with the antibodies indicated on the right.

FIG. 15A. MCF-7 cells were treated with 100 ng/ml TNF-α and total protein lysates were probed with α-HEF1/p130cas. FIG. 15B. MCF-7 cells were treated 100 ng/ml TNF-α in the presence or absence of the caspase 3 inhibitory peptide z-DEVD-fmk at a final concentration of 25nM. Westerns were probed with α-HEF1/p130 Cas. FIG. 15C. HeLa cells were transfected with empty vector (V), HEF1 (H). HEF1 carboxy-terminally tagged with the myc epitome(H-M), or p130cas (p130). Western blots were probed with aHEF1/p130Cas. FIG. 15D. Diagram of the HEF1 caspase cleavage sites and the pieces that are generated.

FIG. 16A. MCF-7 cells were treated with TNF-α in the absence or presence of the proteosome inhibitor ALLN. Lysates were probed with anti-HEF1 specific antibodies (anti-HEF1/I to detect p 115, p105, and p55, anti-HEF 1/2 to detect p65) or anti-HEF1/p130cas to detect the 28 kD species. HeLa cells transfected with the HEF1 cDNA were run in the right lane as a size control for the various HEF1 cleavage products. FIG. 16B. MCF-7 cells were synchronized by thymidine block. The cells were released for four hours prior to the addition of the proteosome inhibitor lactacystin (final concentration 10 $\mu$M). Mitotic cells were collected at 9 hours by mitotic shake off and lysates were probed with either anti-HEF1/p130cas antibodies to detect the 65 and 28 kD forms or anti-HEF1 specific antibodies which detect the 55 kD form.

DETAILED DESCRIPTION OF THE INVENTION

Figure 4A:
FIGS. 4A and 4B. Blots showing the generation of MCF7 stable cell lines in which HEF1 expression is regulated by tetracycline.

Definitions: Various terms relating to the biological molecules of the present invention are used hereinabove and also throughout the specifications and claims.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program.

The present invention also includes active portions, fragments, derivatives and functional or non-functional mimetics of HEF1 polypeptides or proteins of the invention. An "active portion" of HEF1 polypeptide means a peptide that is less than the full length HEF1 polypeptide, but which retains measurable biological activity.

A "fragment" or "portion" of the HEF1 polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the HEF1 polypeptide sequence, antigenic determinants, viral antigens or epitopes are useful for eliciting immune responses to a portion of the HEF1 amino acid sequence.

A "derivative" of the HEF1 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of original the HEF1 polypeptide.

As mentioned above, the HEF1 polypeptide or protein of the invention includes any analogue, fragment, derivative or mutant which is derived from a HEF1 polypeptide and which retains at least one property or other characteristic of the HEF1 polypeptide. Different "variants" of the HEF1 polypeptide exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the HEF1 polypeptide, (c) variants in which one or more amino acids include a substituent group, and (d) variants in which the HEF1 polypeptide is fused with another peptide or polypeptide such as a fusion partner, a protein tag or other chemical moiety, that may confer useful properties to the HEF1 polypeptide, such as, for example, an epitope for an antibody, a polyhistidine sequence, a biotin moiety and the like. Other HEF1 polypeptides of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such allelic variations, analogues, fragments, derivatives, mutants, and modifications, including alternative nucleic acid processing forms and alternative post-translational modification forms result in derivatives of the HEF1 polypeptide that retain any of the biological properties of the HEF1 polypeptide, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specfically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product. Amino acid residues described herein are preferred to be in the "L" isomeric form. However, residues in the "D" isomeric form may be substituted for any L-amino acid residue, provided the desired properties of the polypeptide are retained.

All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50–60% by weight of a given material (e.g., nucleic acid, oligonucleotide, protein, etc.). More preferably, the preparation comprises at least 75% by weight, and most preferably 90–95% by weight of the given compound. Purity is measured by methods appropriate for the given compound (e.g. chromatographic methods, agarose or polyacrylamide gel electrophoresis, HPLC analysis, and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned;by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other manners, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

Using a screen to identify human genes that promote psuedohyphal conversion in the yeast *Saccharomyces cerevisiae*, a cDNA clone was obtained that causes strong pseudohyphal growth of *S. cerevisiae* on low nitrogen medium. This dimorphic shift from normal to "pseudohyphal" budding in yeast has been shown to involve the action of growth regulatory kinase cascades and cell cycle-related transcription factors (Gimeno & Fink, Mol. Cell Biol. 14: 2100–2112, 1994; Gimeno et al., Cell 68: 1077–1090, (1992); Blacketer et al., Mol. Cell Biol. 13: 5567–5581, (1993); Liu et al. Science 262: 1741–1744, (1993)).

A full-length clone of approximately 3.7 kb (SEQ ID NO:1, FIG. 1) encoding HEF1 protein having about 834 amino acids was isolated. HEF1 contains an amino-terminal SH3 domain and an adjacent domain containing multiple SH2 binding motifs. The protein also contains a carboxy terminal "effector" domain that is capable of inducing the shift to pseudo-hyphal budding in yeast. A cDNA encoding a mouse homolog of the carboxy-terminal "effector" region has also been identified (FIG. 3). Homology searches of the Genbank data base revealed an approximately 64% similarity on the amino acid level between HEF1 and the adapter protein, p130cas, recently cloned from rat (as disclosed by Sakai et al., EMBO J. 13: 3748–3756, 1994). However, p130cas is significantly larger than HEF1 (968 amino acids for rat p130cas versus 834 amino acids for HEF1), and differs with respect to amino acid composition. A comparison of HEF1 with p130cas is set forth in greater detail in Example 1.

HEF1 can be classified within a family of docking adapters, which includes p130cas and Efs, capable of multiple associations with signaling molecules and transduction of such signals to coordinate changes in cellular growth regulation, morphology and apoptosis. The HEF1 protein comprises, from amino- to carboxy-terminus, an SH3 domain, a poly-proline domain, several SH2 binding motifs, a serine rich region, and the carboxy-terminal effector domain.

A human clone that encodes an exemplary signal mediator protein of the invention is sometimes referred to herein as "HEF1 " (human enhancer of filamentation) to reflect the screening method by which it was in part identified. The nucleotide sequence of HEF1 is set forth herein as Sequence I.D. No. 1. The amino acid sequence deduced from Sequence I.D. No. 1 is set forth herein as Sequence I.D. No. 2. The characteristics of HEF1 are described in greater detail in Example 1.

Docking adaptor proteins are found at focal adhesion sites and through multiple protein interactions activate signaling cascades in response to integrin receptor binding of the extracellular matrix.

To explore HEF1 function, we established stable MCF7 epithelial cell lines in which HEF1 expression was regulated by an inducible promoter. We demonstrate that HEF1 expression mediates enhancement of cell spreading and conversion to a polarized crescent shaped cell with a large leading edge lamellipodia and pronounced trailing edge. The conversion to a crescent-shaped morphology was accompanied by reorganization of the underlying actin cytoskeleton, pattern of focal contacts, and tubulin array. HEF1 expressing cells also exhibited enhanced motility as demonstrated by augmented fibronectin-mediated haptotaxis and an increase in cell speed in the absence of an attractant. Analysis of the periodicity of cell speed oscillations revealed that HEF1 specifically accelerated the rate at which cells move during motile phases. After prolonged HEF1 expression, crescent-shaped cells stopped moving and appeared to experience stretch-generated tension as a consequence of failure to coordinate lamellipodial extension with release of the cell rear. These morphological features correlated with the onset of cell death, suggesting that HEF1 expression eventually leads to dysregulation of cellular attachment which provides a mechanical stimulus that triggers apoptotic cell death.

We also report herein that HF1 protein expression is cell cycle regulated with the full length forms cleaved in mitosis at a caspase consensus site to generate an amino terminal 55 kD form that localizes to the mitotic spindle. The identification of a caspase sensitive site in HEF1 led us to investigate if HEF1 belongs to a select group of caspase substrates cleaved in apoptosis to promote the morphological changes characteristic of programmed cell death. Significantly, inducing expression of HEF1 in MCF-7 cells causes extensive apoptosis, as assessed by visible cell death, and an increase in caspase 3-like activity. The induction of HEF1 expression also increases JNK activation implicating this pathway in HEF1 action. Endogenous HEF1 is cleaved into 65 kD, 55 kD, and 28 kD forms in response to the induction of apoptosis via TNF-α treatment of MCF-7 cells or αIgM treatment of WEHI 231 cells, paralleling cleavage of PARP and FAK. The generation of these HEF1 forms in response to apoptotic stimuli is prevented by the inhibitory peptide z-DEVD-fmk implicating a caspase 3 like activity in their formation. The accumulation of HEF1 forms is further regulated by the proteosome as the proteosome inhibitors ALLN and lactacystin enhances their stability. Based on these results, it appears that dysregulation of HEF1 and its family members may signal the destruction of focal adhesion sites and regulate onset of apoptosis.

The following description sets forth the general procedures involved in practicing the present invention. To the extent that specific materials are mentioned, it is merely for purposes of illustration and is not intended to limit the invention. Unless otherwise specified, general cloning and gene expression procedures, such as those set forth in Current Protocols in Molecular Biology, Ausubel et al. eds., J W Wiley and Sons, NY (1998) are utilized.

I. Preparation of HEF1-Encoding Nucleic Acid Molecules, HEF1 Proteins and Antibodies Thereto A. Nucleic Acid Molecules Nucleic acid molecules encoding the HEF1 of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as the full length cDNA having Sequence I.D. No. 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 3.7 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 3.7 kb double-stranded molecule. A synthetic DNA molecule so constructed may then be cloned and amplified in an appropriate vector.

Nucleic acid sequences encoding HEF1 may be isolated from appropriate biological sources using methods known in the art. In a preferred embodiment, a cDNA clone is isolated from an expression library of human origin. In an alternative embodiment, genomic clones encoding HEF1 may be isolated. Alternatively, cDNA or genomic clones encoding HEF1 from other mammalian species may be obtained.

In accordance with the present invention, nucleic acids having the appropriate level sequence homology with the protein coding region of Sequence I.D. No. 1 may be identified by using hybridization and washing conditions of appropriate stringency. For example, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable E. coli host cell.

HEF1-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting HEF1 genes in test samples of potentially malignant cells or tissues, e.g. by PCR amplification, or for the isolation of homologous regulators of morphological control.

B. Proteins

A full-length HEF1 of the present invention may be prepared in a variety of ways, according to known methods. The protein may be purified from appropriate sources, e.g., human or animal cultured cells or tissues, by immunoaffinity purification. However, this is not a preferred method due to the low amount of protein likely to be present in a given cell type at any time.

The availability of nucleic acids molecules encoding HEF1 enables production of the protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of HEF1 may be produced by expression in a suitable procaryotic or eucaryotic system. For example, part or all of a DNA molecule, such as the cDNA having Sequence I.D. No. 1, may be inserted into a plasmid vector adapted for expression in a bacterial cell, such as *E. coli,* or into a baculovirus vector for expression in an insect cell. Such vectors comprise the regulatory elements necessary for expression of the DNA in the bacterial host cell, positioned in such a manner as to permit expression of the DNA in the host cell. Such regulatory elements required for expression include promoter sequences, transcription initiation sequences and, optionally, enhancer sequences.

The HEF1 produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The HEF1 proteins of the invention, prepared by the aforementioned methods, may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward HEF1 or fragments thereof may be prepared according to standard methods. In a preferred embodiment, monoclonal antibodies are prepared, which react immunospecifically with various epitopes of HEF1. Monoclonal antibodies may be prepared according to general methods of Köhler and Milstein, following standard protocols. Polyclonal or monoclonal antibodies that immunospecifically interact with HEF1 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-HEF1 antibodies are described below.

II. Uses of HEF1-Encoding Nucleic Acids, HEF1 Proteins and Antibodies Thereto

Cellular signalling molecules have received a great deal of attention as potential prognostic indicators of neoplastic disease and as therapeutic agents to be used for a variety of purposes in cancer chemotherapy. As a signaling molecule that induces profound morphological changes and mediates apoptotic cell death, HEF1 and related proteins from other mammalian species promise to be particularly useful research tools, as well as diagnostic and therapeutic agents.

A. HEF1-Encoding Nucleic Acids

HEF1-encoding nucleic acids may be used for a variety of purposes in accordance with the present invention. HEF1-encoding DNA, RNA, or fragments thereof may be used as probes to detect the presence of and/or expression of genes encoding HEF1. Methods in which HEF1-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The HEF1-encoding nucleic acids of the invention may also be utilized as probes to identify related genes either from humans or from other species. As is well known in the art, hybridization stringencies may be adjusted to allow hybridization of nucleic acid probes with complementary sequences of varying degrees of homology. Thus, HEF1-encoding nucleic acids may be used to advantage to identify and characterize other genes of varying degrees of relation to HEF1, thereby enabling further characterization the signaling cascade involved in the morphological control of different cell types. Additionally, they may be used to identify genes encoding proteins that interact with HEF1 (e.g., by the "interaction trap" technique), which should further accelerate elucidation of these cellular signaling mechanisms.

Nucleic acid molecules, or fragments thereof, encoding HEF1 may also be utilized to control the expression of HEF1, thereby regulating the amount of protein available to participate in oncogenic signaling pathways. Alterations in the physiological amount of "adapter protein" may act synergistically with chemotherapeutic agents used to treat cancer. In one embodiment, the nucleic acid molecules of the invention may be used to decrease expression of HEF1 in a population of malignant cells. In this embodiment, HEF1 proteins would be unable to serve as substrate acceptors for phosphorylation events mediated by oncogenes thereby effectively abrogating the activation signal. In this embodiment, antisense oligonucleotides are employed which are targeted to specific regions of HEF1-encoding genes that are critical for gene expression. The use of antisense oligonucleotides to decrease expression levels of a pre-determined gene is known in the art. In a preferred embodiment, such antisense oligonucleotides are modified in various ways to increase their stability and membrane permeability, so as to maximize their effective delivery to target cells in vitro and in vivo. Such modifications include the preparation of phosphorothioate or methylphosphonate derivatives, among many others, according to procedures known in the art.

In another embodiment, overexpression of HEF1 is induced in a target population of cells to generate an excess of HEF1 molecules. Overexpression of HEF1 leads to alterations in the cytoskeleton and induces cell death. Additionally, overexpression of HEF1 by this method facilitates the isolation and characterization of other components involved in the protein-protein complex formation that occurs via the SH2 homology domains during signal transduction.

As described above, HEF1-encoding nucleic acids are also used to advantage to produce large quantities of substantially pure HEF1 protein, or selected portions thereof. In a preferred embodiment, the C-terminal "effector domain" of HEF1 is produced by expression of a nucleic acid encoding the domain. The full-length protein or selected domain is thereafter used for various research, diagnostic and therapeutic purposes, as described below.

B. HEF1 Protein and Antibodies

Purified HEF1, or fragments thereof, may be used to produce polyclonal or monoclonal antibodies which also may serve as sensitive detection reagents for the presence and accumulation of HEF1 (or complexes containing HEF1) in cultured cells or tissues from living patients (the term "patients" refers to both humans and animals). Recombinant techniques enable expression of fusion proteins containing part or all of the HEF1 protein. The full length protein or fragments of the protein may be used to advantage to generate an array of monoclonal antibodies specific for various epitopes of the protein, thereby providing even greater sensitivity for detection of the protein in cells or tissue.

Polyclonal or monoclonal antibodies immunologically specific for HEF1 may be used in a variety of assays designed to detect and quantitate the protein, which may be useful for rendering a prognosis as to a malignant disease. Such assays include, but are not limited to: (1) flow cytometric analysis; (2) immunochemical localization in HEF1 in cultured cells or tissues; and (3) immunoblot analysis (e.g., dot blot, Western blot) of extracts from various cells and tissues. Additionally, as described above, anti-HEF1 can be used for purification of HEF1 (e.g., affinity column purification, immunoprecipitation).

Anti-HEF1 antibodies may also be utilized as therapeutic agents to block the normal functionality of HEF1 in a target cell population, such as a tumor. Thus, similar to the antisense oligonucleotides described above, anti-HEF1 antibodies may be delivered to a target cell population by methods known in the art (i.e. through various lipophilic carriers that enable delivery of the compound of interest to the target cell cytoplasm) where the antibodies may interact with intrinsic HEF1 to render it nonfunctional.

From the foregoing discussion, it can be seen that HEF1-encoding nucleic acids and HEF1 proteins of the invention can be used to detect HEF1 gene expression and protein accumulation for purposes of assessing the genetic and protein interactions involved in the regulation of morphological control pathways of a cell or tissue sample. Aberrant morphological changes are often correlatable with metastatic cellular proliferation in various cancers, such as breast cancer. It is expected that these tools will be particularly useful for diagnosis and prognosis of human neoplastic disease. Potentially of greater significance, however, is the utility of HEF1-encoding nucleic acids, proteins and antibodies as therapeutic agents to disrupt the signal transduction pathways mediated by activated oncogenes that result in aberrant morphological cellular alterations and cell death.

Although the compositions of the invention have been described with respect to human diagnostics and therapeutics, it will be apparent to one skilled in the art that these tools will also be useful in animal and cultured cell experimentation with respect to various malignancies and/or other conditions manifested by alterations in cellular morphology. As diagnostic agents, they can be used to monitor the effectiveness of potential anti-cancer agents on signal transduction pathways mediated by oncogenic proteins in vitro, and/or the development of neoplasms or malignant diseases in animal model systems. As therapeutics, they can be used either alone or as adjuncts to other chemotherapeutic drugs to improve the effectiveness of such anti-cancer agents.

III. Detection of HEF1 Associated Mutations and Diagnostic Screening Assays Therefore Given the role HEF1 plays in the maintenance of cell morphology, it is highly likely that mutated HEF1 plays a role in certain cancers. Identifying such mutant molecules of HEF1 facilitates the design of therapeutic agents for the treatment of malignancy.

Currently, the most direct method for mutational analysis is DNA sequencing, however it is also the most labor intensive and expensive. It is usually not practical to sequence all potentially relevant regions of every experimental sample. Instead some type of preliminary screening method is commonly used to identify and target for:sequencing only those samples that contain mutations. Single stranded conformational polymorphism (SSCP) is a widely used screening method based on mobility differences between single-stranded wild type and mutant sequences on native polyacrylamide gels. Other methods are based on mobility differences in wild type/mutant heteroduplexes (compared to control homoduplexes) on native gels (heteroduplex analysis) or denaturing gels (denaturing gradient gel electrophoresis). Sample preparation is relatively easy in these assays, and conditions for electrophoresis required to generate the often subtle mobility differences that form the basis for identifying the targets that contain mutations are known to those of skill in the art. Another parameter to be considered is the size of the target region being screened. In general, SSCP is used to screen target regions no longer than about 200–300 bases. Another type of screening technique currently in use is based on cleavage of unpaired bases in heteroduplexes formed between wild type probes hybridized to experimental targets containing point mutations. The cleavage products are also analyzed by gel electrophoresis, as subfragments generated by cleavage of the probe at a mismatch generally differ significantly in size from full length, uncleaved probe and are easily detected with a standard gel system. Mismatch cleavage has been effected either chemically (osmium tetroxide, hydroxylamine) or with a less toxic, enzymatic alternative, using RNase A. The RNase A cleavage assay has also been used, although much less frequently, to screen for mutations in endogenous mRNA targets for detecting mutations in DNA targets amplified by PCR. A mutation detection rate of over 50% was reported for the original RNase screening method.

A newer method to detect mutations in DNA relies on DNA ligase which covalently joins two adjacent oligonucleotides which are hybridized on a complementary target nucleic acid. The mismatch must occur at the site of ligation. As with other methods that rely on oligonucleotides, salt concentration and temperature at hybridization are crucial. Another consideration is the amount of enzyme added relative to the DNA concentration.

In summary, exemplary approaches for detecting alterations in HEF1 encoding nucleic acids or polypeptides/proteins include:

a) comparing the sequence of nucleic acid in the sample with the wild-type HEF1 nucleic acid sequence to determine whether the sample from the patient contains mutations; or b) determining the presence, in a sample from a patient, of the polypeptide encoded by the HEF1 gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal HEF1 gene or from known mutations thereof; or, d) using a specific binding member capable of binding to a HEF1 nucleic acid sequence (either normal sequence or known mutated sequence), the specific binding member comprising nucleic acid hybridizable with the HEF1 sequence, or substances comprising an antibody domain with specificity for a native or mutated HEF1 nucleic acid sequence or the polypeptide encoded by it, the specific binding member being labeled so that binding of the specific binding member to its binding partner is detectable; or, e) using PCR involving one or more primers based on normal or mutated HEF1 gene sequence to screen for normal or mutant HEF1 gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for susceptibility alleles, the HEF1 nucleic acid in the sample will initially be amplified, e.g. using PCR, to increase the amount of the analyte as compared to other sequences present in the sample. This allows the target HEF1 sequences to be detected with a high degree of sensitivity if they are present in the sample. This initial step may be avoided by using highly sensitive array techniques that are becoming increasingly important in the art.

The identification of the HEF1 gene and its association with cellular morphology, signal transduction and apoptosis paves the way for aspects of the present invention to provide the use of materials and methods, such as are disclosed and discussed above, for establishing the presence or absence in a test sample of a variant form of the gene, in particular an allele or variant specifically associated with the neoplastic state. This may be for diagnosing a predisposition of an individual to cancer. It may be for diagnosing cancer in a patient with the disease as being associated with the altered HEF1 gene.

This allows for planning of appropriate therapeutic and/or prophylactic measures, permitting stream-lining of diagnosis, treatment and outcome assessments. The approach further!stream-lines treatment by targeting those patients most likely to benefit.

According to another aspect of the invention, methods of screening drugs for therapy to identify suitable drugs for restoring HEF1 product functions are provided.

The HEF1 polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a HEF1 polypeptide or fragment and the agent being tested, or examine the degree to which the formation of a complex between a HEF1 polypeptide or fragment and a known ligand is interfered with by the agent being tested.

Another technique for drug screening provides high throughput screening for compounds having suitable binding affinity to HEF1 polypeptides and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with HEF1 polypeptide and washed. Bound HEF1 polypeptide is then detected by methods well known in the art.

A further technique for drug screening involves the use of host eukaryotic cell lines or cells (such as described above) which have a nonfunctional HEF1 gene. These host cell lines or cells are defective at the HEF1 polypeptide level. The host cell lines or cells are grown in the presence of drug compound. The rate of growth and morphology of the host cells is measured to determine if the compound is capable of regulating the growth and morphology of HEF1 defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19–21. In one approach, one first determines the three-dimensional structure of a protein of interest (e.g., HEF1 polypeptide) or, for example, of the HEF1-substrate complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527–533). In addition, peptides (e.g., HEF1 polypeptide) may be analyzed by an alanine scan (Wells, 1991) Meth. Enzym. 202:390–411. In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved HEF1 polypeptide activity or stability or which act as inhibitors, agonists, antagonists, etc. of HEF1 polypeptide activity. By virtue of the availability of cloned HEF1 sequences, sufficient amounts of the HEF1 polypeptide may be made available to perform such analytical studies as x-ray crystallography. In addition, the knowledge of the HEF1 protein sequence provided herein will guide those employing computer modeling techniques in place of, or in addition to x-ray crystallography.

IV. Therapeutics

A. Pharmaceuticals and Peptide Therapies

The elucidation of the role played by HEF1 in cellular morphology and apoptosis facilitates the development of pharmaceutical compositions useful for treatment and diagnosis HEF1 associated disorders. These compositions may comprise, in addition to one of the above substances, a pharmaceutcally acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

B. Methods of Gene Therapy

As a further alternative, the nucleic acid encoding the authentic biologically active HEF1 polypeptide could be used in a method of gene therapy, to treat a patient who is unable to synthesize the active "normal" polypeptide or unable to synthesize it at the normal level, thereby providing the effect elicited by wild-type HEF1 and suppressing the occurrence of "abnormal" HEF1 associated altered cellular morphology and apoptosis.

Vectors, such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses.

Gene transfer techniques which selectively target the HEF1 nucleic acid to oral tissues are preferred. Examples of this include receptor-mediated gene transfer, in which the nucleic acid is linked to a protein ligand via polylysine, with the ligand being specific for a receptor present on the surface of the target cells.

The following Examples are provided to describe the invention in further detail. The Examples are intended to illustrate and not to limit the invention.

EXAMPLE 1

Isolation and Characterization of a Nucleic Acid Molecule Encoding Human HEF1

In this Example, we describe the cloning of a cDNA molecule encoding human HEF1. This cDNA is referred to herein as HEF1 for human enhancer of filamentation, because of its identification in the pseudohyphal screen. We also provide an analysis of the structure of the human HEF1 (hHEF1) protein. Additionally, we describe the antibodies immunospecific for the recombinant hHEF1 protein, and their use in immunological detection of phosphorylated HEF1 from normal and Abl transformed NIH3T3 cells.

Isolation of cDNA and Cloning

A HeLa cDNA library constructed in the TRP1+vector JG4-4 (Gyuris et al., Cell 75:791–803), was translated with inserts expressed as native proteins under the control of the galactose-inducible GALL promoter, into CGx74 yeast (MATa/α trp1/trp1; see Gimeno et al., 1992, supra). TRP+ transformants were plated to the nitrogen-restricted SLAGR medium (like SLAD, but with 2% galactose, 1% raffinose as a carbon source), and 120,000 colonies were visually screened using a Wild dissecting microscope at 50× amplification to identify colonies that produced pseudohyphae more extensively than background. cDNAs from these colonies were isolated and retransformed to naive CGx74; those that reproducibly generated enhanced pseudohyphae were sequenced. A 900 bp cDNA encoding a 182 amino acid open reading frame corresponding to the COOH-terminus of hHEF1 (HEF1-Cterm 182) possessed the most dramatic phenotype of cDNA obtained in this screen. Using the original 900 bp cDNA isolated in the pseudohyphal screen to probe a placental cDNA library cloned in lambda gt11, a larger clone (3.4 kb) was isolated. The longer clone obtained in this screen was used as a basis for 5' RACE using a kit from Clontech containing RACE-ready cDNA prepared from human kidney. Three independent clones from the RACE approach yielded identical 5' end-points located 18 base pairs upstream of the ATG encoding the first methionine in the sequence shown in FIG. 1. Repeated efforts with multiple primer sets showed no evidence for an N-terminally extended sequence. The full length clone, HEF1, is about 3.7 kb and encodes a protein about 835 amino acids in length.

Sequence Analysis

Both strands of the HEF1 clone were sequenced using oligonucleotide primers to the JG4-4 vector and to internal HEF1 sequences in combination with the Sequenase system (United States Biochemical) Database searching was performed using the BLAST algorithm (Altschul et al., J. Mol. Biol. 215:403–410, 1990) and sequence analysis was carried out using the package of programs from UWGCG (Devereux et al., Nucl. Acids Res. 12:387–397, 1984).

Northern Analysis

HEF1 cDNA was labeled with $^{32}$P-dCTP by random priming, and used to probe a Northern blot containing 2 μg/lane human mRNA from multiple tissues. The blot was stripped and reprobed with a $^{32}$P-labeled oligonucleotide specific for actin as a control for equivalent loading.

Immunoprecipitation and Western Blotting

Immunoprecipitation of HEF1 from normal and Abl transformed NIH 3T3 cells was accomplished using polyclonal antiserum raised against a peptide derived from the hHEF1 C-terminus. Immunoprecipitates were resolved by electrophoresis on a 12% SDS-polyacrylamide gel. Following electrophoresis, immunoprecipitates were transferred to nitrocellulose, and reprobed with anti-phosphotyrosine antibody (4G10).

Growth Profiles

Yeast were transformed with HEF1 or vector alone and grown to saturated overnight cultures in trp$^-$ glucose defined minimal medium, and re-diluted to OD600<0.05 in trp$^-$ galactose for growth curves. Growth curves were performed, with readings taken at 90 minute intervals for 12 hours, and at less frequent intervals up to 48 hours or longer.

Interaction Trap or Two Hybrid Analysis

EGY48 yeast (Gyuris et al., 1993, supra) were transformed by standard methods with plasmids expressing LexA-fusions, activation-domain fusions, or both, together with the LexA operator-LacZ reporter SH18-34 (Gyuris et al., 1993, supra). For all fusion proteins, synthesis of a fusion protein of the correct length in yeast was confirmed by Western blot assays of yeast extracts (Samson et al., Cell 57: 1045–1052, 1989) using polyclonal antiserum specific for LexA (Brent and Ptashne, Nature 312: 612–615, 1984) or for hemagglutinin (Babco, Inc), as appropriate. Activation of the LacZ reporter was determined as previously described (Brent and Ptashne, Cell 43: 729–736, 1985). Beta-galactosidase assays were performed on three independent colonies, on three separate occasions, and values for particular plasmid combinations varied less than 25%. Activation of the LEU2 reporter was determined by observing the colony forming ability of yeast plated on complete minimal medium lacking leucine. The LexA-PRD/HD expressing plasmid has been described (Golemis and Brent, Mol. Cell Biol. 12: 3006–3014, 1992).

Results

Overexpression of the C-terminal domain of HEF1 influences *Saccharomyces cerevisiae* cell morphology. To identify proteins that regulate the morphology and polarity of human cells, a human cDNA library was screened for genes which enhanced formation of pseudohyphae when expressed in *S. cerevisiae*. The yeast undergoes a dimorphic shift in response to severe nitrogen limitation that involves changes in budding pattern, cell cycle control, cell elongation, and invasive growth into agar (Gimeno et al., 1992, supra). A galactose-inducible HeLa cell cDNA library was used to transform a yeast strain that can form pseudohyphae on nitrogen-restricted media, and a number of human genes which specifically enhanced pseudohyphal formation were identified.

One of the cDNAs derived from this screen was found to cause the constitutive formation of pseudohyphae on rich and nitrogen restricted media. This cDNA is sometimes referred to as "HEF1-Cterm182" (because it encodes 182 amino acids of the C-terminal domain of the human HEF1). A full-length clone containing the cDNA sequence was thereafter obtained. Analysis of the sequence of this cDNA (Sequence I.D. No. 1; FIG. 1) revealed that it was a novel human gene with strong sequence similarity to the rat p130cas gene (as disclosed by Sakai et al. EMBO J. 13: 3748–3756, 1994). This gene was designated HEF1, and its encoded protein was designated hHEF1 (Sequence I.D. No. 2). A comparison of the amino acid compositions (% by weight) of the HEF1 and rat p130cas is shown in Table 1 below.

TABLE 1

| Amino Acid | % Composition | |
|---|---|---|
| | HEF1 | p130cas |
| Alanine | 4.3 | 6.2 |
| Arginine | 6.1 | 7.5 |
| Asparagine | 4.1 | 1.8 |
| Aspartic acid | 5.6 | 6.5 |
| Cysteine | 1.5 | 0.6 |
| Glutamine | 8.3 | 8.1 |
| Glutamic acid | 6.6 | 5.8 |
| Glycine | 3.5 | 4.5 |
| Histidine | 4.0 | 3.1 |
| Isoleucine | 4.2 | 1.6 |
| Leucine | 8.7 | 9.6 |
| Lysine | 6.2 | 4.8 |
| Methionine | 2.8 | 1.0 |
| Phenylalanine | 3.2 | 1.6 |
| Proline | 7.0 | 11.1 |
| Serine | 6.6 | 6.7 |
| Threonine | 4.8 | 4.9 |
| Tryptophan | 1.1 | 1.1 |

TABLE 1-continued

| Amino Acid | % Composition | |
|---|---|---|
| | HEF1 | p130cas |
| Tyrosine | 4.8 | 4.7 |
| Valine | 5.6 | 7.7 |

The deduced length of HEF1 is 834 amino acids and its deduced molecular weight is about 107,897 Da. The deduced length of the rat p130cas is 968 amino acids and its deduced molecular weight is about 121,421 Da.

Tissue specific expression of HEF1. RNA production was assessed by Northern blot analysis. HEF1 is expressed as two predominant transcripts of approximately 3.4 and 5.4 kb. Although present in all tissues examined (heart, brain, placenta, lung, liver, skeletal muscle, kidney and pancreas), these transcripts are present at significantly higher levels in kidney, lung, and placenta. In contrast, a more uniform distribution throughout the body has been reported for p130cas. Two other cross-hybridizing minor species were detected, migrating at 8.0 kb in lung and 1.2 kb in liver. These may represent alternatively spliced HEF1 transcripts or other HEF1/p130cas related genes. HEF1 represents a distinct gene from p130 cas rather than a human homolog, inasmuch as a screen of a murine genomic library with HEF1 cDNA led to identification of an exon that encoded a mouse C-terminal effector protein having a sequence essentially identical to HEF1-Cterm182 (FIG. 3). Furthermore, probe of a zoo blot at high stringency with a HEF1 cDNA probe indicates this gene is highly conserved from humans to yeast.

HEF1 does not induce constitutive pseudohyphal budding by causing severe cell stress. The possibility that the C-terminal domain of hHEF1 was enhancing pseudohyphae formation by causing severe cell stress was excluded by comparing the growth rates of yeast containing the HEF1-Cterm182 cDNA to yeast containing the expression vector control on plates and in liquid culture, with galactose as a sugar source to induce expression of HEF1-Cterm182. The growth rate data shows that HEF1-encoding genes are not simply toxic to yeast.

HEF1 belongs to a class of "adapter proteins" important in signaling cascades influencing morphological control. The HEF1 gene is approximately 3.7 kb and encodes a single continuous open reading frame of about 835 amino acids. The HEF1 protein notably contains an amino-terminal SH3 domain and an adjacent domain containing multiple SH2 binding motifs. Homology search of the Genbank database revealed that HEF1 is 64% similar at the amino acid level to the adapter protein p130cas, recently cloned from rat (Sakai et al., EMBO J. 13:3748–3756, 1994).

Figure 2:
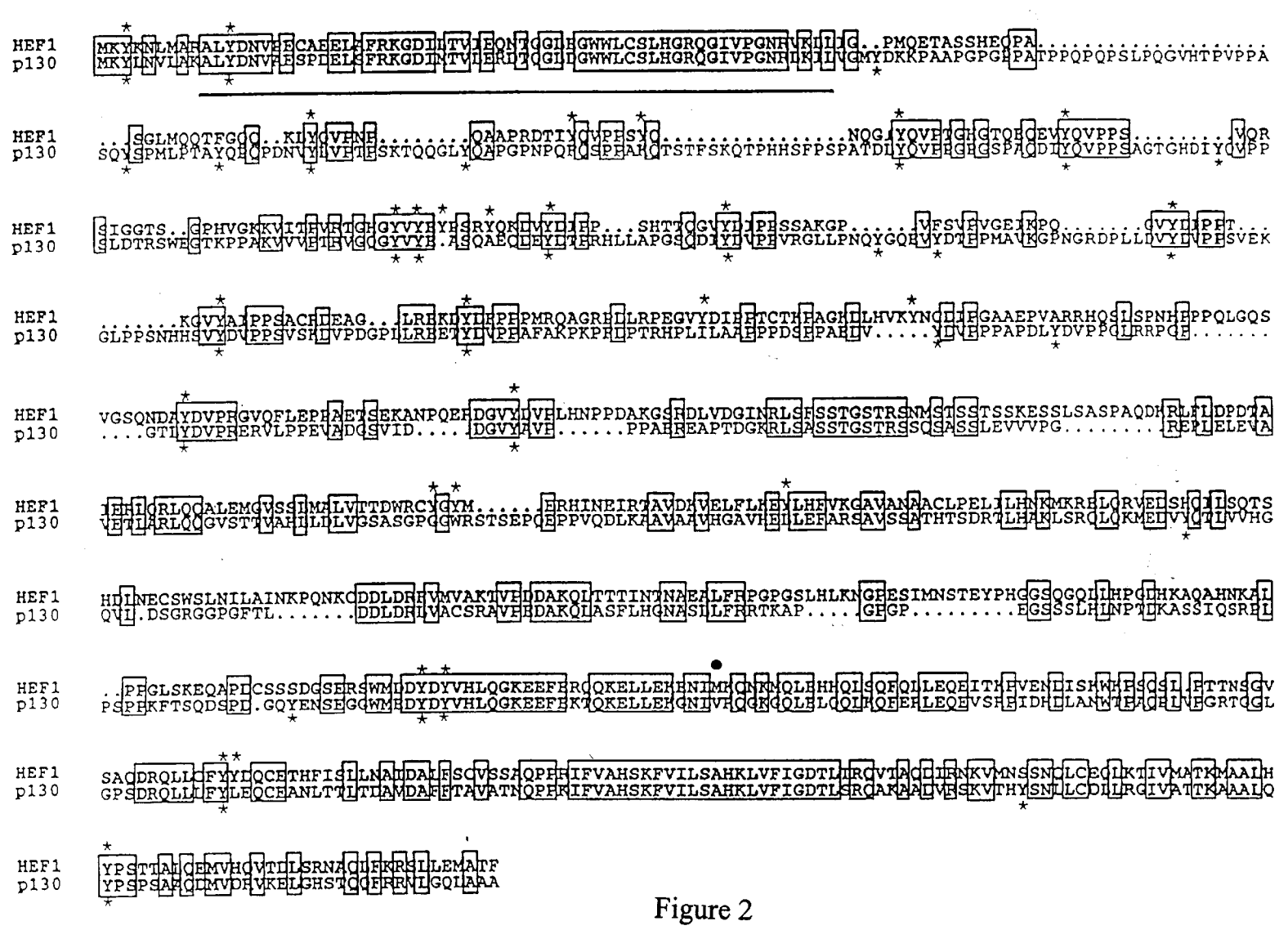

The amino acid alignment of HEF1 and p130cas is shown in FIG. 2. P130cas was determined to be the predominant phosphorylated species in cells following transformation by the oncoprotein Crk and also complexes with, and is a substrate for Abl and Src. As shown in Table 2 below, the homology between HEF1 and 130cas is most pronounced over the SH3 domain (92% similarity, 74% identity) and in the region corresponding to the HEF1-Cterm182 fragment (74% similarity, 57% identity). Although the domain containing SH2-binding motifs is more divergent from p130cas, HEF1 similarly possesses a large number of tyrosines in this region. The majority of SH2 binding sites in p130cas match the consensus for the SH2 domain of the oncoprotein Crk, while the amino acids flanking the tyrosine residues in HEF1 are more diverse, suggesting a broader range of associating proteins. Various SH2 binding motifs conserved between hHEF1 and p130cas are shown in Table 3.

TABLE 2

Domain Alignment: HEF1 and p130cas
(Domains from amino to carboxyl terminus down the Table)

| Domain | Size (a.a.) HEF1 | Size (a.a.) p130cas | % Similarity/Identity (HEF1:p130cas) |
|---|---|---|---|
| SH3 | 50 | 50 | 92% similar, 74% identical |
| Polyproline | 10 | 38 | (not compared) |
| SH2 binding motifs | 290 | 410 | 55% similar, 36% identical |
| Serine-rich region | 250 | 260 | 56% similar, 35% identical |
| C-terminal effector domain | 210 | 210 | 74% similar, 57% identical |

TABLE 3

Conserved SH2 Binding Motifs and Associating Proteins

| SH2 Binding Motif | Associating Proteins |
|---|---|
| YDIP | Crk |
| YDVP | |
| YDFP | |
| YEYP | Vav or fps/fes |
| YAIP | Abl |
| YQNQ | Grb2 |
| YQVP | Novel |
| YQKD | |
| YVYE | |
| YPSR | |
| YNCD | |

The enhancement of pseudohyphal formation by hHEF1-Cterm182 fragment in addition to the relatively high degree of homology to p130cas suggests that this domain acts as an effector in regulating cellular morphology. A test was performed to assay whether the homologous region of p130cas also enhanced pseudohyphal formation. The results show that the C-terminal fragment of p130cas did enhance psuedohyphal formation but not to the same extent as the C-terminal fragment of HEF1. HEF1 was found to induce the strongest pseudohyphal phenotype. By comparison, p130cas and another pseudohyphal inducer, RBP7 (subunit 7 of human RNA polymerase II, Golemis et al., Mol. Biol. of the Cell, 1995) were only about 60% as effective as the HEF1-Cterm182 fragment.

The possible functions for the novel carboxy-terminal domains were investigated further using two-hybrid analysis. These experiments revealed that this domain mediated HEF1 homodimerization, and HEF1/p130cas heterodimerization, yet failed to interact with non-specific control proteins.

HEF1 is a substrate for oncogene mediated phosphorylation. HEF1 was immunoprecipitated from normal and v-Abl transformed NIH3T3 cells using polyclonal antisera raised against a MAP peptide derived from the HEF1 C-terminal domain. Probe of these immunoprecipitates with antibody to phosphotyrosine revealed a species migrating at approximately 130–140 kD that was specifically observed in Abl-transformed fibroblasts. This species may represent HEF1 phosphorylated by Abl, as HEF1 possesses a good match to SH2 binding domain recognized by Abl. The larger apparent molecular weight as compared with HEF1 deduced molecular weight may reflect glycosylation or may be a result of its phosphorylated state.

HEF1 dimerizes with other important cellular regulatory proteins. To assay whether HEF1 dimerizes with other cellular proteins, the interaction trap/two hybrid analysis system was used. Briefly, a LexA-fusion and an epitope-tagged, activation-domain fusion to HEF1 were synthesized. The expression of proteins of the predicted size in yeast was confirmed using antibodies specific for the fusion moieties. Using a LexA-operator reporter, it was observed that LexA-HEF1 fusion protein activates transcription extremely weakly. However, LexA-HEF1 is able to interact with co-expressed activation domain-fused HEF1 to activate transcription of the reporter, indicating that it is able to form dimers (or higher order multimers).

HEF1 joins p130cas in defining a new family of docking adapters that, through multiple associations with signaling molecules via SH2 binding domains, coordinate changes in cellular growth regulation. The interactions between HEF1 homodimers and HEF1-p130cas heterodimers may negatively regulate HEF1 and p130cas proteins by making them inaccessible to their targets. Alternatively, HEF1 and p130cas could work together to recruit new proteins to the signaling complex. The fact that the novel C-terminal domain shared between HEF1 and p130cas has the ability to cause pseudohyphal formation in yeast implicates these proteins in the alteration of cellular morphology by interacting with the cytoskeleton. In fact, previous yeast-morphology based screens for higher eucaryotic proteins have tended to isolate cytoskeletally related proteins. This invention therefore provides reagents influencing the changes in cell morphology that accompany oncoprotein-mediated transformation in carcinogenesis.

EXAMPLE 2

HEF1 Mediates Epithelial Cell Spreading, Increased Motility and Cell Death

Cell migration plays a critical role in many biological processes including embryonic development, tumor metastasis, wound repair, and inflammation. The transition to and maintenance of a motile phenotype requires that a cell coordinately regulate cell surface receptors and the underlying cytoskeleton to generate traction. This transition requires that a spatial asymmetry of cellular components be established in order to translate such internally generated forces into directed cell movement (Lauffenburger and Horwitz, 1996, Cell 84: 359–369). Polarization can occur in response to a stimulatory gradient (see (Bailly et al., 1998, Exp. Cell Res. 241:285–299), a collision which imparts momentum (Verkhovsky et al. 1999, Curr. Biol. 9:11–20), or spontaneously in an apparently homogeneous environment. Spontaneous polarization may, however, be a consequence of a cell's perception of molecular gradients or response to dynamic receptor-ligand interactions (Lauffenburger and Horwitz 1996, supra). Redistribution of chemosensory signaling receptors and focal adhesion sites to the leading edge lamellipodia reinforces the polarization and hence, promotes directed cell locomotion (Sullivan et al. 1984, J. Cell Biol. 99:1461–7; Schmidt et al. 1993, J. Cell Biol. 123:977–91; Lawson and Maxfield 1995, Nature .377:75–79).

The dynamics of focal adhesion assembly/disassembly and subsequent reorganization of the underlying actin cytoskeleton greatly impact cell movement. Focal adhesion sites consist of integrin receptors clustered following their engagement by extracellular ligands and and an associated complex of intracellular proteins which includes actin filaments, actin binding and crosslinking proteins, and a number of tyrosine kinases, phosphatases, and docking/adaptor proteins (Dedhar and Hannigan, 1996, Curr. Opin. Cell Biol. 8:657–669). This complex of proteins has both a structural function to connect the intracellular actin scaffold to the extracellular matrix (ECM) and a signaling function to generate and convey information from the cell periphery that impacts on cell growth, motility, and differentiation (Dedhar and Hannigan 1996, supra). Focal adhesions integrate the mechanical signals derived from morphological changes with the chemical signals triggered by receptor engagement (Chen et al. 1997, Science 276:1425–1428; Chicurel et al. 1998, Curr. Opin. Cell Biol 10:232–9; Huang et al. 1998, Mol. Biol. Cell 9:3179–3193). Although much remains to be investigated, the contributions of a number of kinases and docking/adaptor proteins to the signaling capacity of focal adhesions have been elucidated. For example, focal adhesion kinase (FAK) and FAK family members are tyrosine kinases that localize to focal adhesion sites, undergo autophosphorylation following integrin receptor engagement, and contribute to focal adhesion regulation. Members of the Src family of tyrosine kinases colocalize with FAK and phosphorylate components of focal adhesions. The enzymatic activity of these kinase families creates binding sites for SH2 domain docking/adaptor proteins, thereby promoting assembly of a network of focal adhesion proteins and initiating downstream signaling cascades. Substrates of these kinases include actin binding proteins like paxillin and adaptor proteins like Crk and the Cas (Crk-associated substrate family of signaling proteins (reviewed in (Hanks and Polte 1997, Bioessays 19:137–145)).

The Cas family of adaptor proteins includes p130cas (Sakai et al. 1994, supra), human enhancer of filamentation I (HEF1) ((Law et al. 1996, supra); also known as CasL (Minegishi et al. 1996, J. Exp. Med. 184:1365–1375)), and Efs ((Ishino et al. 1995, Oncogene 11:2331–2338); also known as Sin (Alexandropoulos and Baltimore 1996, Genes Dev. 10:1341–1355)). Members of this family were initially identified as components of viral transformation signaling pathways and/or as modulators of cell growth and morphology. The Cas proteins have a conserved domain structure composed of an amino terminal SH3 domain, a substrate domain which contains multiple tyrosine motifs that are recognized by SH2 domain proteins following phosphorylation, a serine rich region, and a carboxyl terminal dimerization motif. HEF1, p130cas, and Efs are all recruited to focal adhesion sites via interaction of their SH3 domains with FAK (Polte and Hanks 1995, supra; Law et al. 1996, supra. The localization of the Cas family members to focal adhesions suggests that they perform similar functions at this cellular locale. In fact, both HEF1 and p130cas are known to contribute to the assembly of signaling complexes downstream of the integrin receptor following ligand binding (reviewed in (O'Neill et al. 2000, Trends in Cell Biol. in press)).

Recent studies have established a profile of effects mediated by p130cas expression in fibroblasts. p130cas is required for FAK-induced fibroblast migration and this phenomenon is mediated through direct SH3-dependent interaction of p130cas with FAK (Cary et al. 1998, J. Cell Biol. 140:211–221). In lymphoid cells, a recent study showed that HEF1 (CasL) expression restores T cell migration induced by ligation of CD3 and β1 integrin (Ohashi et al. 1999, J. Immun. 163: 3727–3734). Furthermore, expression of either p130cas or the adaptor protein Crk also induces fibroblast migration. This migratory response is dependent on Cas/Crk complex formation and is blocked by a dominant negative form of the GTPase Rac (Klemke et al. 1998, J.Cell Biol. 140:961–972). This is consistent with the well documented contributions of the Rho family GTPases RhoA, Rac, and Cdc42 to cell motility. The p21 (Cdc42/Rac) activated kinases (Paks), another family of proteins known to regulate motility, may mediate some of the Rho family motility effects, although their contribution appears to vary with the Pak isoform and cell type studied.

A number of studies characterizing HEF1 and p130cas have underscored the potential for functional divergence between these Cas family proteins. For example, HEF1 and p130cas are differentially regulated; HEF1 is expressed at maximal levels in cells of epithelial and lymphoid origin, whereas p130cas is expressed ubiquitously (Sakai et al. 1994, supra). HEF1 is also regulated in a cell cycle dependent manner and is processed by caspases to truncated isoforms that localize to distinct subcellular compartments (Law et al. 1998, Mol. Cell Biol. 18:3540–3551). Most notably, we have recently found that HEF1 expression mediates apoptosis in epithelial cells, which constitutes a novel function for a Cas family member. This feature of HEF1 will be further described in Example 3.

In this example, the roles of HEF1 in control of cell shape, motility, and death in epithelial cells are described. We demonstrate that overexpression of HEF1 induced a temporal cascade of events initiating with dramatic changes in epithelial cell morphology, typified by enhanced cell spreading and the acquisition of a highly polarized crescent-shaped phenotype with a large leading edge lamellipodia and trailing edge. The underlying actin cytoskeleton, pattern of focal contacts, and microtubule array of HEF1 expressing crescent-shaped cells also exhibited profound reorganization. All of these features were consistent with a motile phenotype, which was confirmed by demonstrating that HEF1 expression augmented fibronectin (FN)-mediated haptotaxis and conferred an increase in the absolute speed at which these epithelial cells move in the absence of either a haptotactic or chemotactic gradient. After prolonged exposure to high levels of transgene expression, HEF1 expressing cells stopped moving and assumed a static "trailing edge-tethered" phenotype that appeared to undergo progressively greater stretch-generated tension. This tension appears to be a consequence of a failure to coordinate lamellipodial extension with release of the cell rear and may contribute to the ultimate fate of HEF1 over-expressing cells, which is death. To our knowledge, this is the first demonstration of a protein that induces a spectrum of cellular events that begins with altered cell morphology and cytoskeletal organization, progresses to augmented haptotaxis and enhanced cell speed, and culminates in apoptosis.

The following materials and methods are provided to facilitate the practice of the invention as described in Example 2.

Expression Plasmids. A full length EcoRI-XhoI HEF1 clone was subcloned into pBluescript to acquire 3' and 5' flanking NotI sites. The resultant NotI flanked HEF1 cDNA was then subcloned into the pBPSTR1 retroviral vector (Paulus et al. (1996) J Virol 70: 62–67) downstream of a tetracycline responsive element to create pBPSTR1-HEF1.A second plasmid, pTet-tTAK, encodes the tTA protein which is a fusion of the Tet repressor DNA binding domain and the transcriptional activation domain of VP16 (Gibco/BRL). Coexpression of pBPSTR1-HEF1 and pTet-tTAK in cells therefore produced a tightly regulated system in which HEF1 was expressed in an inducible fashion following removal of tetracycline from the media.

Cell Culture. The human breast adenocarcinoma cell line MCF7 and derivatives were maintained in DME plus 10% fetal bovine serum (FBS). To prepare stable, regulated clonal cell lines, MCF7 cells were cotransfected with pBPSTR1-HEF1, pTet-tTAK, and MSCVhygroR (which provides a hygomycin resistance gene; available from J. Testa, Fox Chase Cancer Center) by Lipofectamine™ mediated DNA transfer (Gibco/BRL). Forty-eight hours after transfection, the cells were selected in media containing 2 $\mu$g/ml puromycin (to retain the tetracycline-regulated pBPSTR1-HEF1), 400 $\mu$g/ml hygromycin, and 1 $\mu$g/ml tetracycline (to repress HEF1 expression during selection). Cell lines were derived from isolated single colonies, expanded, and examined for inducible HEF1 expression. Unless otherwise stated, experiments were carried out in DME plus 10% FBS.

Induction of HEF1, Cell Lysis, and Western Analysis.

Cells were plated at low cell density (~60,0000 cells/100-mm culture dish) in the presence (uninduced) or absence (induced) of tetracycline for ~24 h prior to lysis. Adherent monolayers were washed twice with phosphate buffered saline and then lysed in Triton X-100 lysis buffer [50 mM HEPES (pH 7.5), 50 mM NaCl, 5 mM EDTA, 1% Triton X-100, 50 mM NaF, 10 mM $Na_4P_2O_7$] supplemented with 1 mM sodium orthovanadate, 0.1 mM phenylmethylsulfonyl fluoride, 1 $\mu$g/ml aprotinin, and 1 $\mu$g/ml leupeptin. The protein concentration of total cell lysates was quantitated using the Pierce BCA protein determination kit (Pierce). Total cell lysate was separated by SDS-PAGE and transferred to polyvinyl difluoride membranes (Immobilon). Membranes were blocked using 5% fat free milk, probed with rabbit polyclonal antisera specific for HEF1 ($\alpha$HEF1-SB-R1; (Law et al. (1996) Mol Cell Biol 16: 3327–3337)), and developed using a horseradish peroxidase based chemiluminescent system (NEN).

Cell Spreading Analysis. Cells were initially plated at ~60% confluence in the presence or absence of tetracycline for 18 hours. Cells were then detached by incubation in PBS+5 mM EDTA for 15 minutes at 37° C., replated onto either uncoated glass coverslips in DME plus FBS or human FN (Gibco/BRL) coated coverslips (6 $\mu$g/ml) in serum free DME, and maintained in either inducing, or non-inducing conditions for the indicated times prior to fixation in 3.5% paraformaldehyde. CCD images of eight representative fields per condition were acquired with a 40× objective. In each field, cell area measurements were determined utilizing Inovision ISEE™ software to outline perimeters of individual cells and calculate the number of pixels encompassed. From the resulting area measurements (number of pixels/cell), a mean cell area per condition was determined. The results shown are the mean of three independent experiments +/− the standard error.

Immunofluorescence Detection. Cells cultured on coverslips were fixed in 3.5% paraformaldehyde, permeabilized with 0.2% Tween-20, and blocked with 0.1% BSA in Tris buffer [10 mM Tris (pH 7.5), 150 mM NaCl]. Cells were then incubated with the following primary antibodies: anti-HEF1 rabbit antisera ($\alpha$HEF1-SB-R2), anti-paxillin mouse monoclonal antibodies (Transduction Labs), and anti-tubulin mouse monoclonal antibodies (Sigma). Secondary antibody incubation was consequently performed with either rhodamine-conjugated anti-rabbit antibodies (Molecular Probes), biotin-conjugated anti-rabbit antibodies plus Texas Red-conjugated streptavidin (Vector Laboratories), or DTAF-conjugated anti-mouse antibodies (Jackson Immunological Labs). For visualization of filamentous actin, either FITC-conjugated phalloidin or TRITC conjugated phalloidin (Molecular Probes) was included in a final incubation. A Bio-Rad MRC 600 laser scanning confocal microscope (Cell Imaging Facility, Fox Chase Cancer Center) was used to analyze and record images.

Motility Assays. For measurements of haptotaxis, cell lines (10,000 cells/35 mm-well) were plated onto the porous membrane (top well) of a modified Boyden chamber (tissue-culture treated, 8-$\mu$m pores, Transwell™, Costar Corp., Cambridge, Mass.). Both top and bottom of the Boyden chamber contained DME with or without tetracycline. Soluble human plasma FN (Gibco/BRL) was added (4 $\mu$g/ml, as indicated) to the bottom wells just before cell plating to coat the underside of the porous membrane. Cells attached to the membrane were fixed and stained with modified Giemsa. Cells on the upperside of the membrane were removed by scraping, which facilitated visualization of the cells which had migrated to the underside of the filter. Migratory cells in five to ten randomly selected fields (10× objective) per condition were counted. For each condition (with or without tetracycline), the data were normalized against the number of cells that migrated across the filter in the absence of FN (baseline migratory tendency) and expressed as fold increase over baseline.

For the speed analysis, cell lines were plated at low cell density in DME plus 10% FBS with (uninduced) or without (induced) tetracycline for 4–6 h prior to the start of time lapse videomicroscopy imaging. Phase contrast images were recorded at 5-min intervals for calculation of cell speed for 18–24 h. Cells were tracked for 70 intervals using Isee™, imaging software and the results were analyzed using Excel™.

Results

Figure 4B:
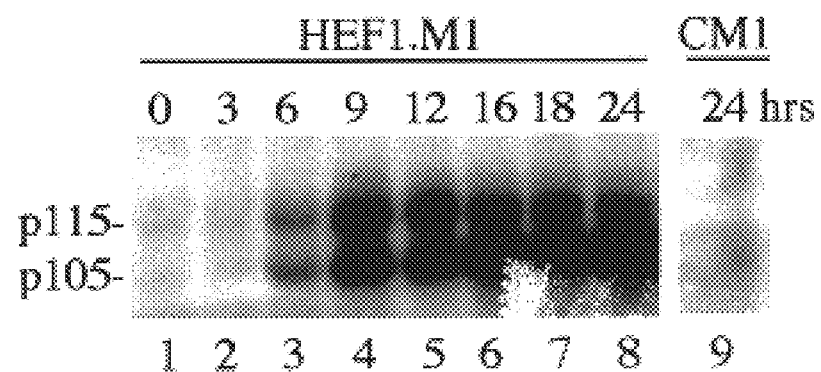

Establishment of Stable Cell Lines That Inducibly Express HEF1. To examine the consequences of HEF1 overexpression, stable cell lines derived from the MCF7 breast adenocarcinoma cell line were created in which HEF1 was under the control of an inducible promoter. HEF1 function was evaluated in an epithelial cell background because the endogenous protein is expressed at high levels in cells of epithelial origin (Law et al. (1996) Mol Cell Biol 16:3327–3337), suggesting that any HEF1 protein partners germane to its function would be present. Moreover, endogenous HEF1 regulation and protein-protein interactions were previously characterized in this cell line (Law et al. (1996) Mol Cell Biol 16:3327–3337; Law et al. (1998) Mol Cell Biol 18:3540–3551). Of note, full length HEF1 protein is differentially phosphorylated and consequently migrates as a 105/115 kD doublet when resolved by SDS-PAGE (Law et al. (1996) Mol Cell Biol 16:3327–3337; Law et al. (1998) Mol Cell Biol 18:3540–3551). Stable MCF7 clonal cell lines that expressed the HEF1 transgene in a tetracycline dependent fashion and parental vector clones were generated and characterized. Immunoblots of total cell lysates derived from HEF1 inducible clones (HEF1.M1 and HEF1.M2) probed with anti-HEF1 specific antibodies ($\alpha$HEF1-SB-R1) showed that transgene expression was tightly regulated and inducible as demonstrated by the appearance of full length p105/115 HEF1 protein following removal of tetracycline (FIG. 4A, compare lane 3 to 4 and lane 5 to 6), while the parental vector clone CM1 demonstrated low endogenous HEF1 expression levels in the presence or absence of tetracycline (FIG. 4A, compare lanes 1 and 2). Endogenous HEF1 was barely detectable under these experimental conditions, but could be better visualized with longer exposures (data not shown; FIG. 4B).

To determine the kinetics of HEF1 expression, total cell lysates were isolated from the HEF1.M1 clone at the indicated time intervals following induction and analyzed on immunoblots probed with αHEF1-SB-R1 antibodies to evaluate HEF1 protein levels. By six hours post-induction (FIG. 4B, Lane 3), HEF1 levels were significantly enhanced in induced HEF1.M1 lysates relative to those of uninduced HEF1.M1 lysates (FIG. 4B, Lane 1). Maximal levels of HEF1 expression were achieved by nine hours of induction (FIG. 4B, Lane 4) and were maintained over the course of the induction spanning twenty-four hours (FIG. 4B, Lanes 4–8). Lysates derived from the uninduced HEF1.M1 clone and the mock induced CM1 clone expressed low levels of HEF1 protein, reflecting the expression of the endogenous protein, at all time intervals examined (FIG. 4B, Lanes 1 and 9, respectively; data not shown). Significantly, the level of post-induction (Table 4; range derived from four independent experiments). This analysis also revealed that the post-induction time at which individual cells became crescents varied, presumably reflecting the heterogeneous nature of HEF1 expression levels in induced populations. Based on the timing with which individual cells converted to a crescent-shaped morphology, the mean conversion time was calculated for each experiment, which ranged from 7.9 to 18.2 hours post-induction (Table 4). Taken together, the data showed that HEF1 expression mediated dramatic changes in epithelial cell morphology at a high frequency in induced populations.

TABLE 4

HEF1 Expressing Cells Assume a Crescent Shape.

| HEF1 | Cell Line | | | | | | | | | | |
|---|---|---|---|---|---|---|---|---|---|---|---|
| | HEF1.M1 (Exp. 1) | | HEF1.M1 (Exp. 2) | | HEF1.M1 (Exp. 3) | | HEF1.M2 | | CM1 (Exp. 1) | | CM1 (Exp. 2) |
| Induction | − | + | − | + | − | + | − | + | − | + | − | + |
| % Crescents | 0 | 75 | 0 | 59 | 0 | 47 | 0 | 57 | 0 | 0 | 0 | 0 |
| Mean Time to Crescent (Hours) | N/A | 7.9 | N/A | 14.3 | N/A | 18 | N/A | 18.2 | N/A | N/A | N/A | N/A |
| Number of Cells | 45 | 32 | 26 | 29 | 30 | 15 | 43 | 21 | 32 | 36 | 49 | 37 |

HEF1 expression in these induced stable cell lines was not grossly upregulated relative to the level of endogenous HEF1 in a variety of cell lines and tissue samples (Law et al. (1998) Mol Cell Biol 18:3540–3551). Moreover, the change in HEF1 expression following induction was of a similar magnitude to that seen for endogenous HEF1 levels during cell cycle progression in MCF7 cells (Law et al. (1998) Mol Cell Biol 18:3540–3551). Thus, the level of transgene expression observed in the HEF1 clones following, induction was within a physiologically relevant range.

Expression of HEF1 Induces a Crescent-shaped Morphology. Morphological changes were evident in HEF1-expressing clones within four to six hours of induction, consistent with the concurrent increase in HEF1 protein levels (FIG. 4B). Phase contrast microscopy of HEF1 expressing clones (HEF1.M1 and HEF1.M2) following eighteen hours of HEF1 induction revealed that the cells had undergone dramatic morphological changes, typified by the appearance of crescent-shaped cells with large leading edge lamellipodia and a pronounced trailing edge (FIG. 5, compare A to B and C to D). This unusual morphology is reminiscent of fish keratocytes, epithelial cells noted for their rapid locomotion (Cooper and Schliwa (1986) J Cell Biol 102: 1384–99; Lee et al. (1993) Nature 362: 167–71). Uninduced HEF1 cells (FIG. 5A and 5C and uninduced or induced CM1 cells (FIG. 5E and 5F) exhibited no morphological changes, suggesting that the altered morphology was not due to secondary effects of tetracycline removal or tet repressor activity, but was a consequence of HEF1 expression.

In order to assess the frequency and timing of HEF1-mediated morphological changes, we analyzed HEF1.M1 and HEF1.M2 cells by time lapse videomicroscopy and determined that 47–75%. of populations expressing HEF1 assumed a crescent-shaped morphology by 18–20 hours Frequency and timing of conversion to crescent-shaped cells in HEF1 and vector control cell lines. Uninduced (−) and induced (+) or mock induced (M) cultures were established in parallel for each cell line indicated and time lapse images of each condition were recorded simultaneously. A representative field of cells was selected for each condition and individual cells included within were followed at 5-min intervals for a duration of 70 intervals. Crescent-shaped cells were identified visually. See Materials and Methods for experimental details set forth in Example 2.

Figure 6A:
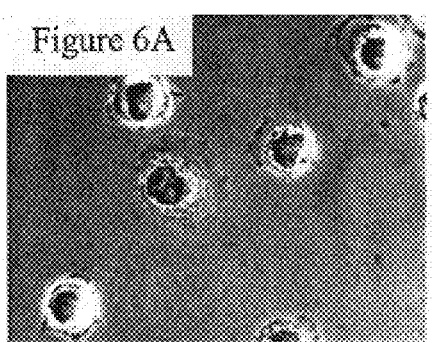
FIGS. 6A–6K. A series of micrographs (FIGS. 6A–6J) and a graph (FIG. 6K) showing HEF1 expression increases cell spreading. HEF1.M1 cells maintained for 18 hours in either non-inducing (FIGS. 6A, 6C, 6E, 6G, 6I) or inducing (FIGS. 6B, 6D, 6F, 6H, 6J) conditions were replated on glass coverslips coated with 6$\mu$g/ml human fibronectin (FN) (1.25 $\mu$g/CM$^2$). Cells were fixed at 30 minutes (FIGS. 6A, 6B); 1 hour (FIGS. 6C, 6D); 2 hours (FIGS. 6E, 6F); 3 hours (FIGS. 6G, 6H); and 6 hours (FIGS. 6I, 6J) after plating. Phase contrast CCD images were acquired with a 40× objective. Cells were maintained in inducing or non-inducing conditions for the duration of the experiment.
Figure 6B:
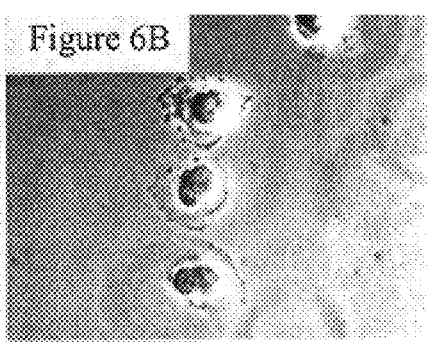
Figure 6C:
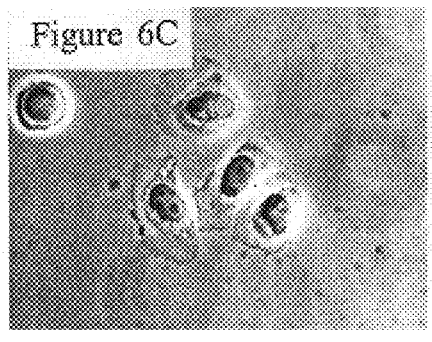
Figure 6D:
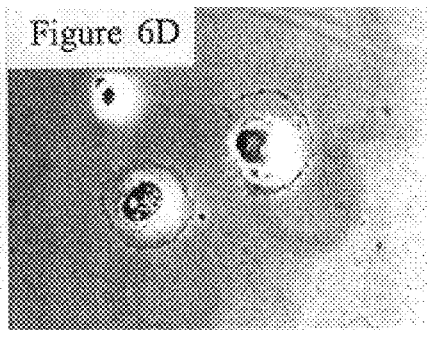
Figure 6E:
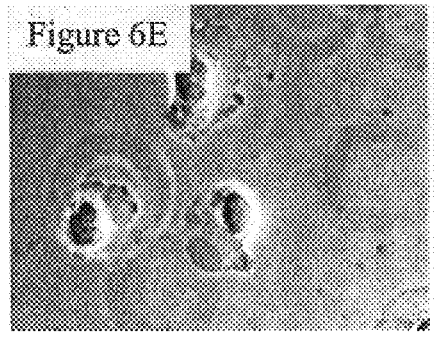
Figure 6F:
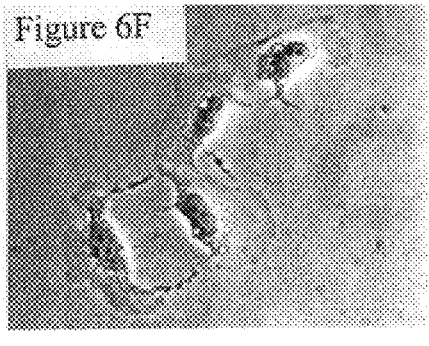
Figure 6G:
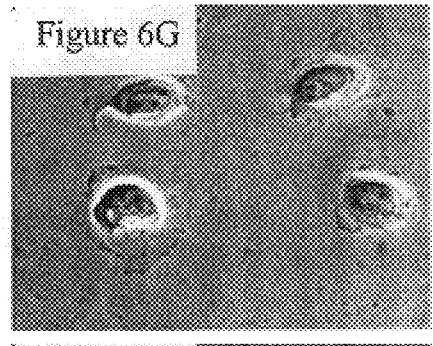
Figure 6H:
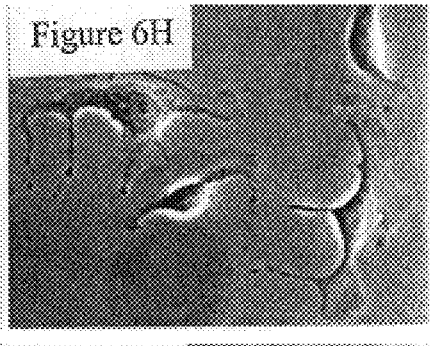
Figure 6I:
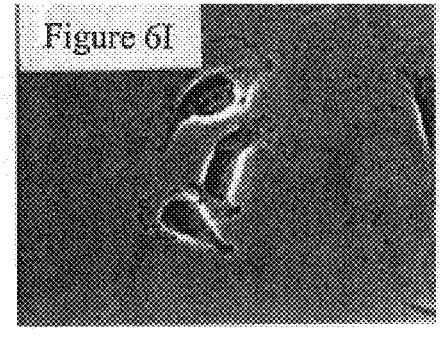
Figure 6J:
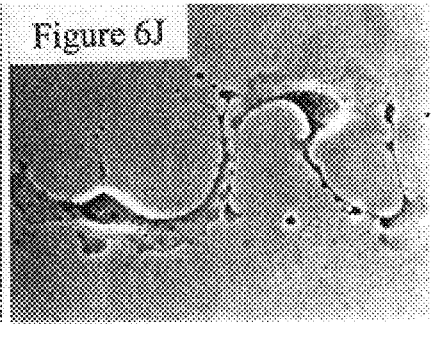
Figure 6K:
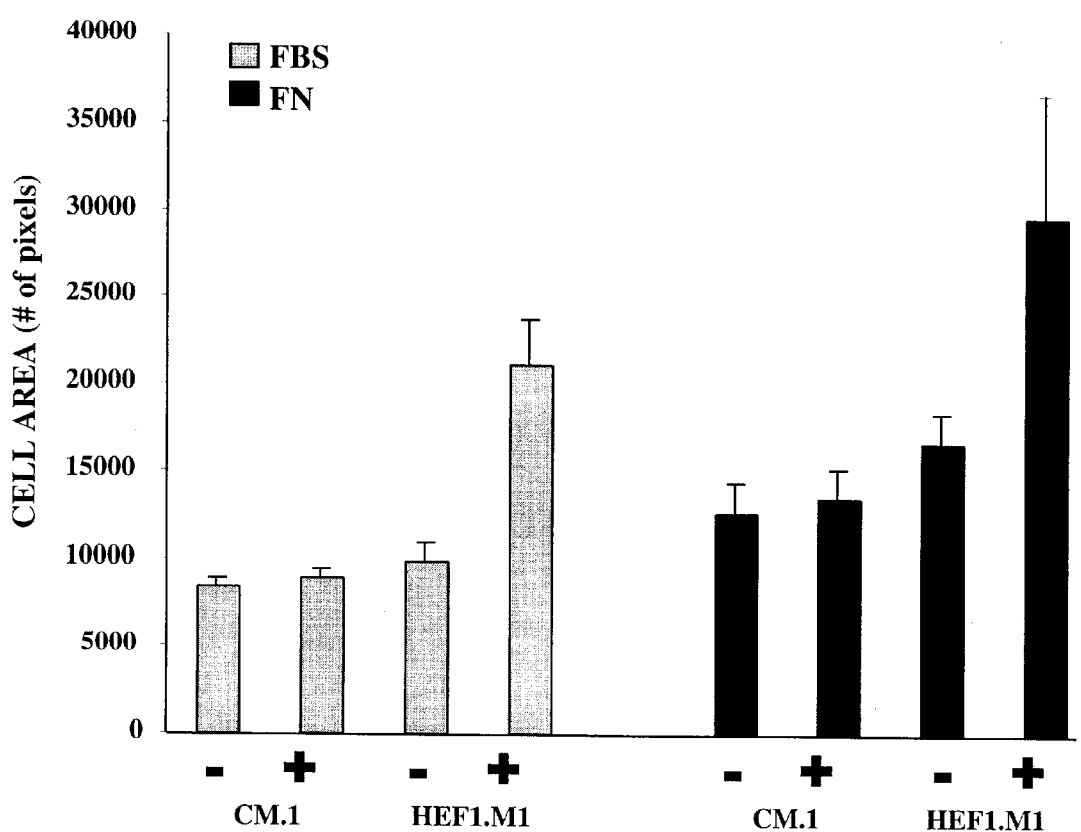

Expression of HEF1 Enhances Cell Spreading. Highly motile cells characteristically exhibit a different pattern of substrate anchorage and a greater degree of spreading than do sessile cells (see, Small et al. (1999) Curr Opin Cell Biol 11:54–60). To evaluate the contribution of increased HEF1 expression to cell spreading, HEF1.M1 cells were induced for eighteen hours to facilitate production of high levels of HEF1 and then replated and allowed to spread on fibronectin (FN)coated coverslips for the indicated time intervals in serum free media under non-inducing, (FIGS. 6 A, C, E, G, I) or inducing (FIGS. 6 B, D, F, H, J) conditions. HEF1 expression clearly enhanced cell spreading within two hours of plating onto FN (compare panel 6F to 6E). In contrast to HEF1 expressing cells, which were well spread and had developed large leading edge lamellipodia (FIG. 6F), uninduced HEF1.M1 cells continued to exhibit a rounded, largely unspread morphology (FIG. 6E). Indeed, the large lamellipodia characteristic of HEF1 expressing cells continued to increase in size and intricacy over time (FIG. 6, panels 6F, 6H, and 6J). Moreover, it was noteworthy that the crescent-shaped morphology was evident on a FN matrix, implying that integrin receptor signaling was sufficient to convey the HEF1 mediated cell shape changes that were observed in the presence of serum (FIG. 5). Interestingly, crescent-shaped cells became progressively more spread during the course of the induction (FIG. 6, compare 6F to 6H or 6J). After six hours post-plating onto FN, HEF1 expressing cells continued to exhibit a morphology distinct from that of uninduced cells and characterized by a crescent-shape, more extensive lamellipodia, and larger cell area (FIG. 6, compare 6I and 6J).

To quantitate the cell area differential, HEF1.M1 cells were induced for eighteen hours and then replated onto either uncoated coverslips in media containing serum or FN-coated coverslips in serum free media for an additional 6 hours under inducing conditions. A readily observable increase in cell area was noted in induced HEF1.M1 populations relative to that of uninduced HEF1.M1 populations, whether the cells were plated in the presence of serum onto uncoated coverslips or in serum-free media onto FN-coated coverslips. Quantification of mean cell area for induced and uninduced populations revealed that HEF1 expression resulted in a 2.2-fold (uncoated coverslips) or a 1.75-fold (FN-coated coverslips) increase in cell area (FIG. 6, lower panel). The mean cell area of uninduced HEF1.M1 cells was similar to that of uninduced or induced CM1 cells, indicating that tetracycline withdrawal had no effect on cell spreading or area. Taken together, these data suggest that HEF1 expression enhanced the degree of cell spreading and mediated a significant increase in planar cell area. The observation that the degree of spreading on a FN matrix was comparable to that observed in the presence of serum indicated that the HEF1 enhancement of cell spreading was largely integrin mediated.

HEF1 Localizes to Prominent Focal Adhesion Sites and the Trailing Edge. To investigate localization of HEF1 and the organization of relevant intracellular structures, indirect immunofluorescence was performed on uninduced and induced clones to visualize HEF1 protein on a subcellular level. Endogenous HEF1 protein was expressed diffusely in uninduced HEF1.M1 cells (FIG. 7A). Following induction, HEF1 localized to focal structures in the cell periphery, in particular to the lamellipodia and membrane ruffles (FIG. 7B). Double label immunofluorescence performed to visualize HEF1 and paxillin demonstrated that these HEF1 structures were focal adhesion sites on the leading edge lamellipodia (FIGS. 7B and 7C). These data were confirmed by colocalization of HEF1 with FAK, another component of focal adhesion sites. HEF1 expressing cells also exhibited reorganization of the actin cytoskeleton with actin bundles arranged radially at the lamellipodial front and in stress fibers radiating out from the perinuclear region to the leading edge (FIG. 7E). Costaining to visualize the actin cytoskeleton using FITC-phalloidin and HEF1 revealed that HEF1 was concentrated at the distal ends of actin stress fibers, thereby coinciding with focal adhesion sites (FIGS. 7D–7F, arrowheads).

Based on the localization of HEF1 to the mitotic spindle (Law et al. (1998) Mol Cell Biol 18:3540–3551) and recent reports demonstrating that there is "cross talk" between microtubules and early sites of substrate contact (Kaverina et al. (1998) J Cell Biol 142:181–90), the effect of HEF1 overexpression on the microtubule array was investigated. To this end, double label immunofluorescence was performed to visualize tubulin and HEF1 in induced HEF1.M1 cells. As shown by FIG. 7H, the underlying microtubule network was reorganized in parallel with the morphological changes mediated by HEF1 expression. In addition to the web-like microtubule network evident throughout the cytoplasm, tubulin staining was most pronounced in the perinuclear region and in the trailing edge of crescent-shaped cells (FIG. 7H). HEF1 colocalized with tubulin in both the perinuclear region and the trailing edge of induced HEF1.M1 cells (FIG. 7G–7I). Of note, tubulin also colocalized with HEF1 in the cell body proximal portions of focal adhesion sites (FIG. 7H). Localization of tubulin to focal contacts has been previously characterized in a variety of cells, including epithelial cells (reviewed in (Waterman-Storer and Salmon 1999 Curr. Opin. Cell Biol. 11:61–67)), where it is thought to contribute to focal adhesion stability (Kaverina et al. (1998) J Cell Biol 142:181–90).

Figure 8:
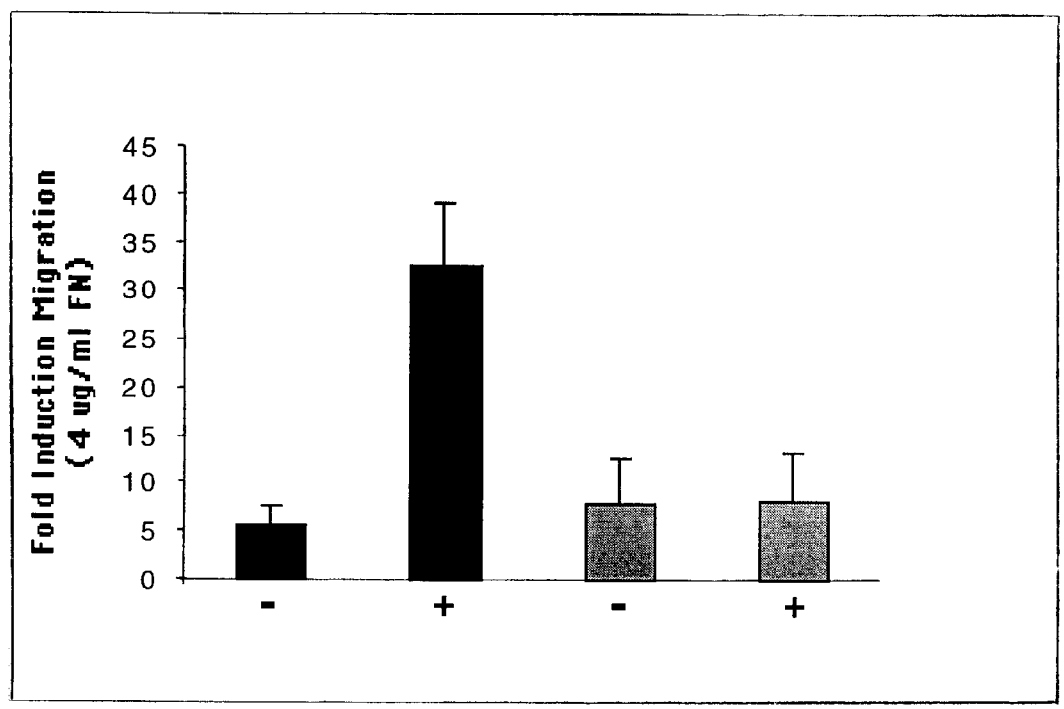
FIG. 8. A graph showing HEF1 expression augments FN mediated haptotaxis. HEF1.M1 (solid bars) or CM1 (shaded bars) cells were seeded into the top well of Boyden chambers and assessed for their ability to migrate toward FN either in non-inducing or inducing conditions. Approximately 20 hours after plating, the number of cells that traversed the membrane was determined. The haptotactic response of populations maintained in either non-inducing (−) or inducing conditions were grouped separately and normalized against the number of cells that traversed the membrane for each condition in the absence of stimulus. Results shown are the mean of two independent experiments for each cell line +/− standard error.

HEF1 Expression Augments Fibronectin Mediated Haptotaxis. Since HEF1 expression induced a morphology typical of motile cells and HEF1 has been implicated as a downstream component of integrin receptor signaling (Nojima et al. (1995) J Cell Chem 270: 15398–15402; Petch et al. (1995) J Cell Science 108: 1371–1379; Vuori and Ruoslahti (1995) J Biol Chem 270: 22259–22262; Vuori et al. (1996) Mol Cell Biol 16:2606:–2613; Astier et al. (1997) Leuk Lymph 28: 65–72), HEF1 expression enhanced FN mediated haptotactic responses in MCF7 cells were of interest. To address this, Boyden chamber assays were performed utilizing HEF1.M1, HEF1.M2, and CM1 cells. Briefly, cells were seeded in serum-free media on the upper side of Transwell filters and the number of cells that migrated through the membrane in response to the presence of soluble FN in the lower chamber was determined. The haptotactic responses of populations maintained in the presence or absence of tetracycline were grouped separately and the data represented graphically as the fold increase in the number of cells that traversed the membrane in response to soluble FN as compared to those that traversed the membrane in the absence of stimulus. Independent experiments showed the migration of HEF1.M1 and CM1 cells towards FN in Boyden chamber assays (FIG. 8). As demonstrated by the fold increase in the number of migratory cells (+/− standard error), both cell lines exhibit FN mediated haptotaxis. Uninduced HEF1.M1 cells exhibited a tendency to migrate toward FN that was comparable to induced or uninduced CM1 cells. Induction of HEF1 expression in HEF1.M1 cells, however, correlated with an approximately six-fold enhancement in FN mediated haptotaxis as compared to that of uninduced HEF1.M1 cells. This result was confirmed utilizing the HEF1.M2 clone in which induction of HEF1 conferred a three- to five-fold enhancement in haptotaxis as compared to that of uninduced HEF1.M2 cells. Qualitatively similar data were reproduced in duplicate (HEF1.M2 cells) or triplicate (HEF1.M1 and CM1 cells) utilizing multiple concentrations of FN. The expression of HEF1, therefore, augmented the natural tendency of these cells to migrate toward FN. Potential mechanisms underlying this augmentation include an overall increase of cell speed, enhanced ability to polarize in a particular direction, and/or mobilization of a greater percentage of the cell population.

Figure 9A:
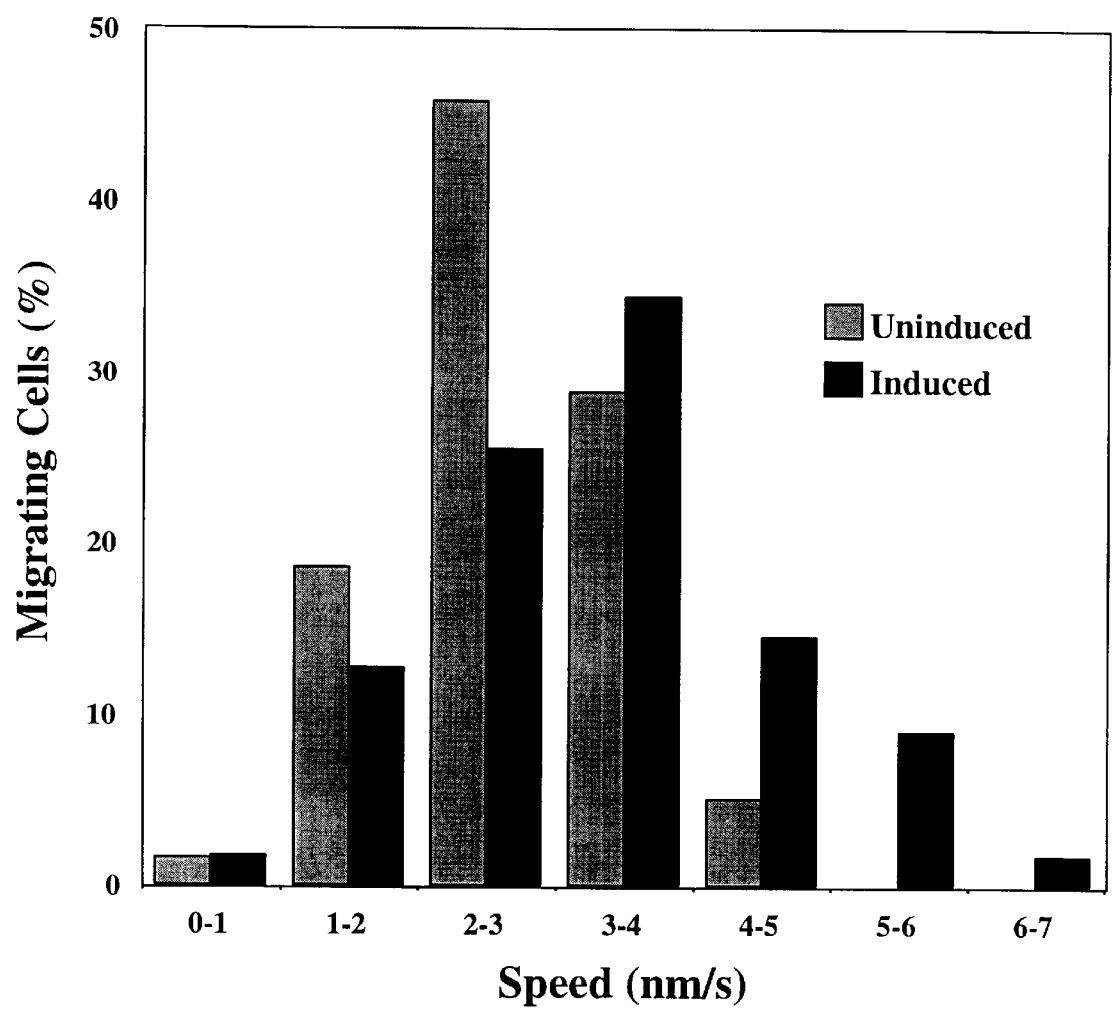
FIGS. 9A and 9B. A pair of graphs showing HEF1 expression enhances cell motility by increasing cell speed. The average speed of uninduced or induced HEF1.M1 (FIG. 9A) or CM1 (FIG. 9B) cells was determined by analyzing the movement of individual cells at 5 minute intervals over the course of approximately six hours using Inovision Isee™ nano-tracking software.
Figure 9B:
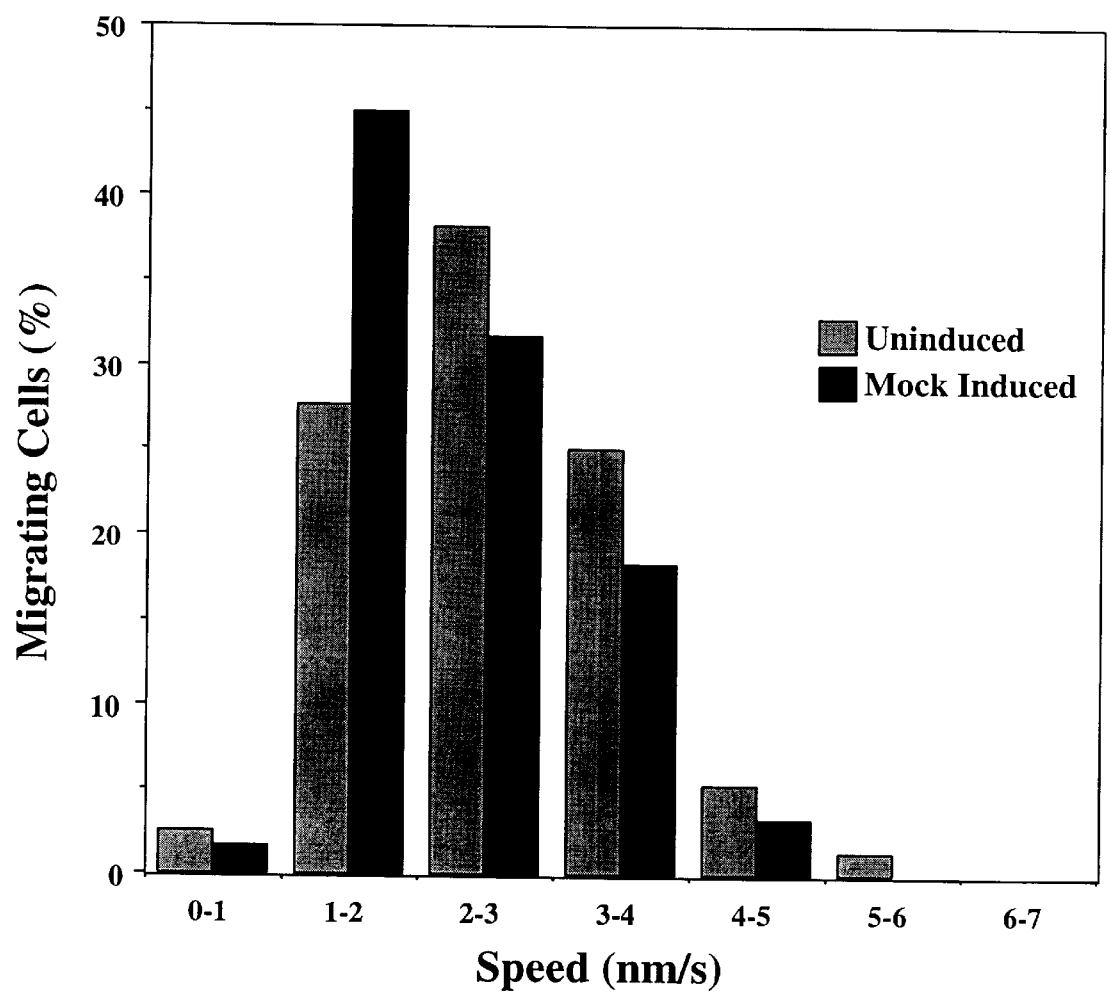

HEF1 Expression Enhances Cell Motility by Increasing Cell Speed. To analyze HEF1 effects on cell motility in greater detail, phase contrast video images of uninduced and induced cell lines were recorded at 5-minute intervals using a CCD camera, compiled, and analyzed using Nanotrack image processing software to determine cell speed. Such analyses of time lapse images revealed that the average speed of HEF1 expressing HEF1.M1 cells [3.33 nm/s +/−0.16 SE (n=55 cells)] exceeded that of uninduced cells [2.65 nm/s +/−0. 11 SE (n=59 cells)]. HEF1 expressing cells, therefore, exhibited a 26% increase in the average speed of cell movement relative to that of uninduced controls. As shown in FIG. 9A, which depicts the percent of the population migrating within defined average speed ranges, HEF1 expression correlated with a greater number of cells traveling at higher speeds. In fact, uninduced HEF1.M1 and parental vector (uninduced and mock induced; FIG. 9B) cells never achieved the maximum speed of 6.0–7.0 nm/s attained by induced HEF1.M1 cells. Parallel analyses of the CM1 clone demonstrated that the average speed of these cells following, removal of tetracycline [(2.23 nm/s +/−0.11 SE (n=60 cells)] was similar to that of cells maintained in the presence of tetracycline [2.52 nm/s +/−0.11 SE (n=76 cells)]. Moreover, the histogram depiction of CM1 cells traveling within defined ranges of speed illustrates a Gaussian distribution that was not altered in mock induced and uninduced populations (FIG. 9B). Of note, the average speed of HEF1.M1 cells (2.65 nm/s +/−0.11 SE) was similar to that of parental vector cells (2.52 nm/s +/−0.11 SE) when maintained in the presence of tetracycline, indicating that the enhanced motility was not due to alterations in the intrinsic motility of the HEF1.M1 clones that arose during the cloning process.

The quantitation of cell speed also revealed that HEF1.M1 and CM1 cells moved in an oscillating fashion, with bursts of speed interspersed with slower phases. Such periodic oscillations in cell speed and internal force generation have been previously characterized in migrating neutrophils, macrophages, and fibroblasts ((Galbraith and Sheetz (1997) Proc Natl Acad Sci U.S.A 94: 9114–8); reviewed in Ehrengruber et al. (1996) J Exp Biol 199: 741–7; Sheetz et al. (1999) Biochem Soc Symp 65:233–43). To evaluate if HEF1-mediated enhancement of cell speed was a consequence of changes in the periodicity of this oscillating pattern, the highly motile phases of individual cells were quantitated over the course of the assay. A highly motile phase was defined as a five minute interval of time during which a cell traveled with a speed equal to or greater than 2 nm/s. These analyses revealed that the expression of HEF1 did not alter the duration or frequency of the highly motile phase of individual cells. Nor did HEF1 expression increase the percent of the total population that was highly motile. Combined, the data demonstrate that HEF1 expression facilitated faster movement in cells during motile phases, but did not alter the oscillating pattern of movement or the percentage of highly motile cells in the population.

Prolonged Expression of HEF1 Induces Phenotypic Changes That Precede Cell Death. Examination of HEF1 clones after prolonged expression of HEF1 revealed a dramatic increase in the number of dead cells in HEF1.M1 and HEF1.M2 populations (Table 5). The increase in the number of dead cells in HEF1 clones after prolonged expression of HEF1 (24–48 hours) was due to apoptosis as revealed by poly (ADP-ribose) polymerase (PARP) cleavage and an increase in caspase activity. To explore the possibility that morphological changes mediated by HEF1 expression could impact on the activation of apoptotic pathways, time lapse videomicroscopy was used to examine the progression and timing of cell death in HEF1.M1 cells. Dead cells were defined visually as those which de-adhered from the plastic, appeared shrunken, and maintained these characteristics during the remaining course of the time lapse videomicroscopy. This analysis revealed that between 27–44% of an induced HEF1.M1 population was dead after twenty-four hours of HEF1 expression (Table 5). In contrast, 0–4% of the uninduced HEF1.M1 populations died (Table 5). These results were reiterated using the independent HEF1 expressing clone HEF1.M2 (Table 5). The above results were qualitatively confirmed in five (HEF1.M1) and two (HEF1.M2) independent experiments. By forty-eight hours post-induction of HEF1, greater than 70% cell death was typically observed for both HEF1.M1 and HEF1.M2 populations. Control CM1 cells did not demonstrate any changes in viability in response to the presence or absence of tetracycline (Table 5). These data demonstrate that prolonged expression of HEF1 in MCF7 cells resulted in a dramatic increase in the number of dead cells in induced populations.

TABLE 5

Prolonged HEF1 Expression Mediates Cell Death.

| | Cell Line | | | | | | | | | |
|---|---|---|---|---|---|---|---|---|---|---|
| | HEF1.M1 (Exp. 1) | | HEF1.M1 (Exp. 2) | | HEF1.M2 | | CM1 (Exp. 1) | | CM1 (Exp. 2) | |
| HEF1 Induction | − | + | − | + | − | + | − | + | − | + |
| % Dead Cells | 4 | 44 | 0 | 27 | 0 | 29 | 6 | 6 | 0 | 0 |
| Mean Time to Death (hours) | 22.4 | 11.5 | N/A | 22.6 | N/A | 19.5 | 18.2 | 21.9 | N/A | N/A |
| % Crescents that die | N/A | 58 | N/A | 43 | N/A | 42 | N/A | N/A | N/A | N/A |
| Number of Cells | 45 | 32 | 30 | 15 | 43 | 21 | 32 | 36 | 49 | 37 |

Frequency of dead cells in HEF I and vector control cell lines. Uninduced (−) and induced (+) or mock induced (M) cultures were established in parallel for each cell line indicated and time lapse images of each condition were recorded simultaneously. A representative field of cells was selected for each condition and individual cells included within were followed at 5-min intervals for a duration of 70 intervals. Dead cells were identified visually as those cells which de-adhered from the plastic, appeared shrunken, and remained inert and rounded over the remaining course of the assay. See Materials and Methods in Example 2 for experimental details.

The analysis of time lapse images also revealed that cell death was frequently preceded by the phenotypic conversion to a crescent-shaped cell which eventually appeared to undergo progressively greater stretch-generated tension as the trailing edges elongated after failing to release their attachments and eventually pulled away from the plastic. Such elongated crescent-shaped cells, which began to appear after approximately nine hours of HEF1 induction, were defined as late stage crescent-shaped cells. FIG. 10 illustrates the terminal progression of the three late stage crescent-shaped cells. Each panel represents a single frame derived from a time lapse movie of HEF1.M1 cells induced to express HEF1. In FIG. 10A, three late stage crescent-shaped cells were visualized after 9 hours, 5 minutes of HEF1 induction. Within five minutes (9 hours, 10 minutes post-induction), one of these cells has de-adhered from the plastic and become an inert, rounded cell mass (FIG. 10B). Panels 10C and 10D depict the demise of the second late stage crescent-shaped cell within a five minute interval (between 9 hours, 40 minutes and 9 hours, 45 minutes). The death of the third late stage crescent-shaped cell within a five minute interval (between 10 hours, 30 minutes and 10 hours, 35 minutes) is visualized in panels 10E and 10F. Prior to death, the trailing edge of each of these crescent-shaped cells were elongated relative to the cell body size and appeared to be statically tethered to the underlying matrix. All three of these cells remained in the state depicted in FIG. 10F throughout the duration of the assay which spanned 24 hours of HEF1 induction. Within the first twenty-four hours of HEF1 induction, 34–58% of the crescent-shaped cells analyzed by time lapse videomicroscopy underwent a similar morphological transition (range derived from five independent experiments). Moreover, 60–100% of the dead cells in the HEF1 expressing populations examined had undergone such a morphological progression (based on analyses of time lapse images from five independent experiments). Taken together, the data indicate that a correlation exists between the progression to a late stage crescent morphology and cell death.

EXAMPLE 3

HEF1 Mediates Apoptosis via JNK, PARP and FAK Pathways

Apoptosis, or programmed cell death (PCD), is critical in an array of processes apparently diverse as nervous system development (Pettmann et al., Neuron 20:633–47, 1998), maturation of lymphoid cells (Scaffidi et al., Curr. Opin. Immunol. 11:277–85, 1999), and appropriate attachment of epithelial cells (Frisch et al., J. Cell Biol. 124:619–626, 1994), but all are linked by the requirement to eliminate specific cellular populations in specific circumstances. Apoptosis is triggered by extracellular signals, such as stimulation of the TNF and Apo families of death receptor (Ashkenazi et al., Science 281:1305–1308, 1998), surface immunoglobulin crosslinking, or interference with cellular adhesion to substrate, as well as via intracellular (Green et al., Science 281:1309–1312, 1998) or activation of cell damage sensing pathways. A hallmark of apoptosis is the activation of a cascade of cellular proteases termed caspases that cleave proteins after aspartic acid residues found in an appropriate amino acid context. "Initiator" caspases (caspases 8, 10, and others) at the top of the cascade are activated, then sequentially cleave and activate downstream "effector" caspases (e.g. caspases 3 and 7), which in turn cleave a specific subset of cellular proteins. Cleavage of this subset leads to characteristic changes in cell morphology, including nuclear fragmentation and cytoskeletal rearrangement (Thornberry et al., Science 281:1312–1316, 1998), and ultimately results in production of apoptotic bodies that are engulfed by surrounding cells (Kerr et al., Br. J. Can. 26:239–257, 1972). Because of the central role of apoptosis in many biological processes, it has been of considerable interest to elucidate the steps of these morphological rearrangements, and to understand the relation between morphological controls in moribund versus normally growing It has long been noted that apoptosis and mitosis both require similar programmed changes in cell shape and some conserved elements of signaling. The first step in both processes requires cell rounding and a reduction in cell attachment to the ECM through modulation of the cell cytoskeleton. Subsequent changes in nuclear morphology, including breakdown of the nuclear envelope and hypercondensation of the chromatin, allow the packaging of nuclear fragments into apoptotic bodies or, in the case of mitosis, formation of the mitotic spindle. Although caspases were originally defined as proteins specifically active in apoptosis, recent work has identified additional roles for these proteins in non-apoptotic cells. For example, caspase 3 activity has been shown to increase upon NIH3T3 cell spreading; reciprocally, cell spreading is blocked by the general caspase inhibitor z-Asp (Watanabe, et al., J. Cell Physio. 179:45–51, 1999). Two pieces of evidence specifically link caspase activity and cell proliferation. First, a significant transient increase in caspase 3 activity is detected in peripheral T lymphocytes upon T cell activation, when these cells are actively proliferating but not engaged in apoptosis. Second, survivin, a protein which has the ability to inactivate caspases 3 and 7, is upregulated at the G2/M transition and localizes to the mitotic spindle. Expression of survivin can block taxol induced apoptosis, suggesting that survivin may act to inhibit a constitutive apoptotic signal in mitosis (Li et al., Nature 396:580–584, 1998). Thus, modulated caspase activity towards specific cellular targets may be important for normal cytoskeletal organization and cell cycle progression, while a dramatic increase or dysregulation of caspase activity is necessary to promote apoptosis.

As described in Example 1, HEF1 (Human Enhancer of Filamentation 1) was first isolated in a screen for human proteins with the ability to alter yeast morphology from round to filamentous hyperpolarized cells. As mentioned previously, HEF1 belongs to a larger family of docking adaptor proteins including p130Cas and Efs/Sin, termed the Cas family. All members of this family contain multiple protein-protein interaction domains allowing for the recruitment of additional proteins into a complex that activates signaling cascades following cell adhesion. These interaction domains include an amino terminal SH3 domain that binds poly-proline containing proteins, a substrate domain with multiple tyrosines that when phosphorylated, recruits SH2 containing proteins, and a conserved carboxy terminal domain that may contribute to dimerization of Cas family members. In interphase cells, HEF1 and other Cas proteins localize to sites of focal adhesion, bind to focal adhesion kinase (FAK) through the conserved SH3 domain, and are phosphorylated by FAK and Src family kinases in response to integrin receptor binding of the extracellular matrix (ECM). See Example 2. This phosphorylation in turn activates SH2 binding sites to recruit the adaptor protein Crk, which then stimulates the Ras/Raf/JNK signaling, cascade, contributing to the promotion of cell migration.

In contrast to p130 Cas, the HEF1 protein is regulated at multiple levels in a cell cycle-dependent manner, with regulation including changes in steady state levels, phosphorylation status, and proteolytic processing. As cells traverse through S phase and G2, full length forms of HEF1 (p105 and p115) accumulate at focal adhesion sites. Strikingly, at the G2/M transition the full length forms of HEF1 are cleaved at a caspase consensus site to generate an amino terminal HEF1 form, p55HEF1, which localizes to the mitotic spindle, while carboxyterminal species (notably a p65) are apparently degraded. The cleavage and relocation of HEF1 during mitosis suggests that HEF1 may play a role in coordinating attachment-based signals generated at focal adhesion sites with cell cycle events in the nucleus, thereby promoting, the transition from flat substrate-attached interphase cells to rounded mitotic cells. The apparent involvement of a caspase-like activity in production of p55HEF1 at mitosis therefore led us to investigate further whether HEF1 belonged to a select subset, of caspase substrates cleaved in apoplosis to promote the cytoskeletal changes characteristic of PCD, and whether misregulation of HEF1 might independently contribute to induction of apoptosis.

The breast adenocarcinoma cell line MCF-7 has been well characterized both for the endogenous expression of HEF1 and its intrinsic ability to undergo apoptosis (Boudreau et al. Science 267:891–893, 1995), making these cells suitable for studies of HEF1 biological activities. Notably, we have found that overexpression of the HEF1 protein in MCF-7 cells efficiently induces apoptosis, as assessed by promotion of caspase activation and cleavage of canonical effector caspase targets. Induction of apoptosis either by HEF1 overexpression, or by treatment with TNF-α or other standard pro-apoptotic agents, causes cleavage of HEF1 into 65 kD, 55 kD, and 28 kD forms by a caspase 3/7-like activity, in a time period paralleling cleavage of effector caspase targets poly(ADP-ribose) polymerase (PARP) and focal adhesion kinase (FAK). p130 Cas is also cleaved to produce a 28 kD species following HEF1 overexpression; comparison of HEF1 and p130 Cas sequences facilitated delineation of the likely shared caspase cleavage target site. The carboxy-terminal p65 and p28 HEF1 cleavage products were found to be subject to degradation via the proteosome, although to a lesser degree than in mitosis, suggesting differential abundance of the cleaved HEF1 species during the two processes. Finally, the accumulation of HEF1 cleavage products preceded activation of JNK kinases in HEF1 overexpressing cells, providing one possible mechanism for the pro-apoptotic effect of HEF1.

The following materials and methods are provided to facilitate the practice of the invention as described in Example 3.

Cell lines and materials. MCF-7 human breast carcinoma cells and HeLa human cervical carcinoma cells were cultured under standard conditions. The murine B cell lymphoma line, WeHI 231, as well as anti-IgM antibodies (available from Dr. Kerry Campbell, Fox Chase Cancer Center) and were maintained in DMEM. 10% fetal calf serum, glutamine, pen/strep, non-essential amino acids, and β-mercaptoethanol (10 μM). The construction of MCF-7 transfectants carrying either full length HEF1 or empty vector under the control of a tetracycline-repressible operator is described elsewhere (Example 2). The cell lines used in this study are HEF1.M1 and CM1. Antibodies used in this study include anti-p130 Cas, anti-gelsolin, and anti-FAK obtained from Transduction Laboratories (San Diego, Calif.), anti-PARP from Calbiochem (San Diego, Calif.) and anti-phospho JNK from Promega (Madison, Wis.). Anti-HEF1-R1 (here denoted HEF1/1) antibodies were previously described (Law et al., (1998) Mol. Cell. Biol. 13: 3540–3551). Anti-p103Cas has been previously shown to cross-react with the HEF1 C-terminus (Law et al., (1998) Mol. Cell. Biol. 13: 3540–3551) and is referred to herein as anti-HEF1/anti-p130 Cas. Another HEF1 specific antibody (anti-HEF1/2) was generated by injection into rabbits of the peptide KESSLSASPAQDKR, conjugated to KLH. TNF-α was purchased from R & D Laboratories. Colorimetric caspase 3 substrate, Ac-DEVD-pNA was purchased from Calbiochem (La Jolla, Calif.) and dissolved in DMSO as 5 mM stock solutions and stored at −20° C. The caspase inhibitor peptide z-DEVD-fmk and the specific proteosome inhibitor lactacystin were purchased from Calbiochem while the proteosome inhibitors ALLN and ALLM were obtained from Sigma (St. Louis, Mo.). Puromycin dihydrochloride and tetracycline hydrochloride were from Sigma, while hygromycin B was from Boehringer-Mannheim (Roche, Indianapolis, Ind.). LT2 transfection reagent was purchased from Mirus (Madison. Wis.).

Expression constructs. Construction of the pCDNA1/HEF1 construct has been previously described (Law et al., (1998) Mol. Cell. Biol. 13: 3540–3551). C-terminally Myc-His-tagged full length HEF1 was constructed by PCR amplifying HEF1 with primers containing N-terminal EcoRI and C-terminal KpnI restriction enzyme sites. The fragment was then ligated into EcoRI/KpnI digested pCNA3.Mvc/His. Mouse p130Cas cDNA insert was isolated by EcoRI digestion from pCMV5.p130Cas. The resulting fragment was religated into EcoRI digested pCDNA3 and clones containing inserts in the correct orientation determined by nucleotide sequencing.

HEF1 expression and caspase activity. Stable cell lines containing parental tetracycline-regulatable vector with or without the full length HEF1 cDNA were generated in MCF-7 cells (Example 2). These were plated at a density of approximately $1 \times 10^6$ cells per 100 mm plate into fresh DMEM plus 10% fetal bovine serum in the absence of tetracycline and other selective antibiotics (induced) or in the presence of 1 μg/ml tetracycline (uninduced). Floating and attached cells were combined and extracted in caspase assay buffer (50 mM HEPES, pH 7.4, 100 mM NaCl, 0.1% CHAPS, 10 mM DTT, 1 mM EDTA, and 10% glycerol). Protein content of extracts was determined using the Bio-Rad protein assay as per the manufacturer's instructions (Bio-Rad, Hercules, Calif.). Caspase assays were performed as previously described (DiPietrantonio et al. (1999) Biochem Biophys Res Commun 255:477–82). Briefly, 100 μg of total protein extracts were incubated at room temperature in a final volume of 200 μl with Ac-DEVD-pNA (250 μM final concentration) and, where indicated, z-DEVD-fmk (0.5 μM final concentration) in caspase assay buffer. Triplicate samples were incubated at room temperature and the release of pNA product was monitored at 405 nm a microtiter plate reader (Multiskan Plus, Labsystems, Helsinki. Finland). Initial readings were taken at the start of the incubation ($T_0$) and final readings were taken at the completion of the reaction at 24 hr ($T_1$). The change in absorbance over time was determined by subtracting $T_0$ from $T_1$ for each sample.

Induction of apoptosis. MCF-7 cells were plated and grown for 48 hours reaching a cell density of 70% prior to TNF-α addition. Media was replaced with fresh media supplemented with 100 ng/ml TNF-α. TNF-α treatment of stable cell lines was carried out by plating, cells directly into fresh DMEM plus 10% fetal bovine serum, with or without addition of tetracycline as indicated, containing 100 ng/ml TNF-α. Cells floating in the media were collected by centrifugation (1,200 rpm, 5 min) and extracted in combination with attached cells at the time points indicated, as described below. WeHI 231 cells were plated at a density of $5 \times 10^4$ cells/ml and treated with 1 μg/ml of α-IgM antibodies in complete media. Cells were collected by centrifugation and lysed as stated below. Blockade of caspase 3 and 7 activation was accomplished by incubation with the cell permeable caspase inhibitor z-DEVD-fmk at a final concentration of 25 nM, 30 minutes prior to and continuing after the addition of TNF-α or α-IgM as per manufacturer's recommendations.

Proteosome inhibition. The proteosome and calpain were inhibited by the peptide ALLN and its structurally related however less potent analog ALLM (Ikebe et al. (1998) Int J Cancer 77: 578–85). The specific proteosome inhibitor lactacystin was also used for comparison (Dick et al. (1997) J Biol Chem 272: 182–8). The proteosome inhibitors ALLN and ALLM were added coincident with the addition of TNF-α at a final concentration of 50 μM, while lactacystin was added at a final concentration of 10 μM.

Proteosome inhibition in mitosis was accomplished as follows: MCF-7 cells were blocked in 2 mM thymidine as previously described (Law et al., (1998) Mol. Cell. Biol. 13: 3540–3551). Cells were washed twice in DMEM and then released in DMEM plus 10% fetal bovine serum for four hours. Then either a DMSO control or lactacystin at a final concentration of 50 μM was added and the cells incubated for five more hours. Mitotic cells were then harvested by gently tapping the dish and collecting cells in the supernatant by centrifugation.

Transient transfection. HeLa cells were plated 24 hours prior to transfection. Transfection was accomplished using the LT2 reagent (Mirus) following the manufacturer's suggested protocol. Cells were harvested 24 hours following the initiation of the transfection.

Preparation of cell lysates and Western blot analysis.

Lysates were made as previously described (39; 41) in A-PTY buffer (50 mM HEPES, pH 7.5, 50 mM NaCl, 5 mM EDTA, 1% Triton X-100, 50 mM NaF, 10 mM $Na_4P_2O_7$ and supplemented each extraction with 1 mM phenylmethylsulfonylfluoride, 0.01 mg/ml aprotinin and 0.01 mg/ml leupeptin). For adherent cultures, floating cells were pooled with the adherent cells prior to lysis. The cell pellet was then lysed in combination with lysates from the attached cells. Western analysis was carried out with the previously described antibody concentrations or those suggested by the manufacturer. Detection was via chemiluminescence as described (Law et al. (1996) Mol. Cell. Biol. 16: 3327–3337).

RESULTS

Figure 11:
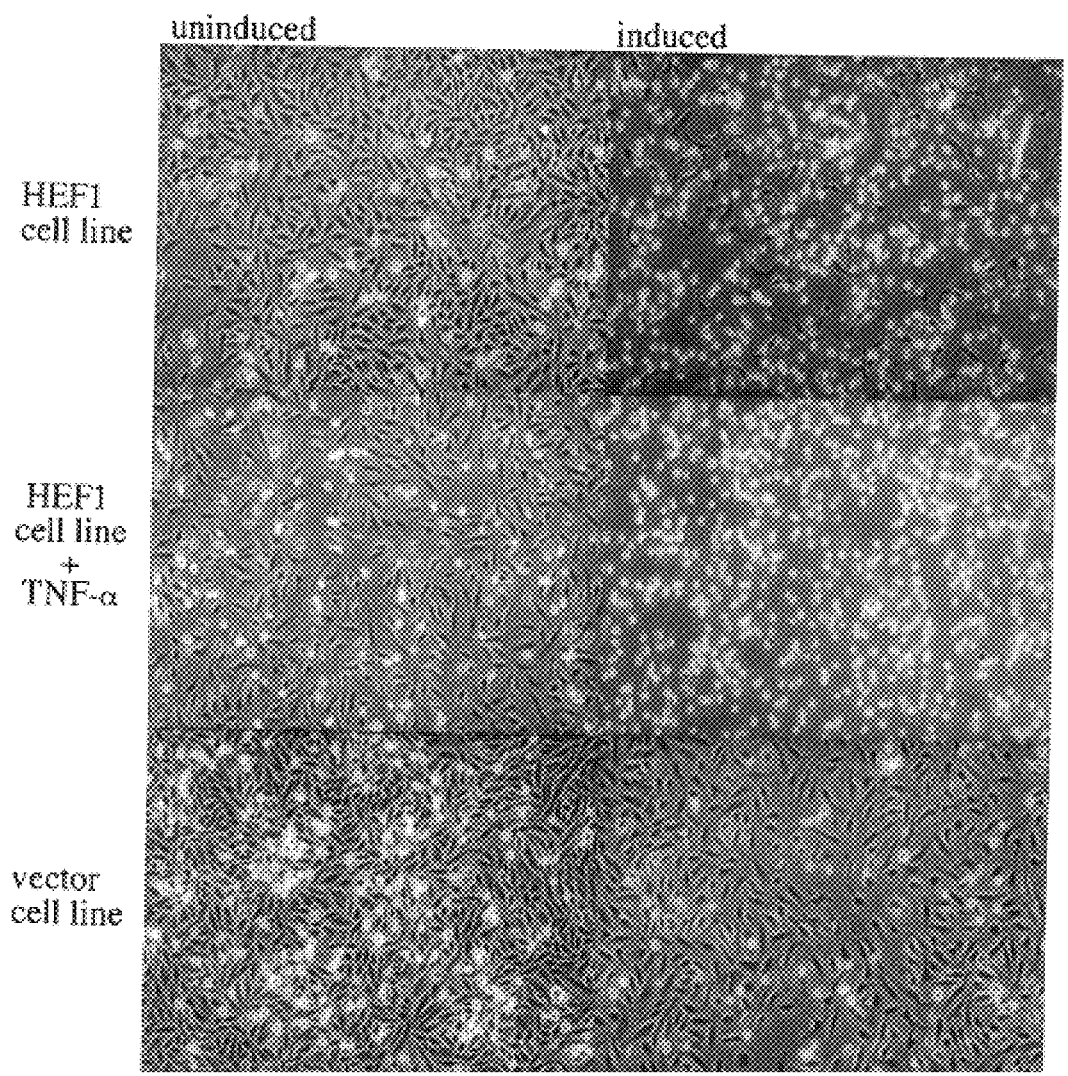
FIG. 11. Phase contrast micrographs showing that HEF1 expression causes cell death. Cells were grown for 48 hours in the presence (uninduced) or absence (induced) of tetracycline and where indicated TNF-α. HEF1 stable transfectants (HEF1 cell line) were compared with a negative control cell line (vector cell line).
Figure 12A:
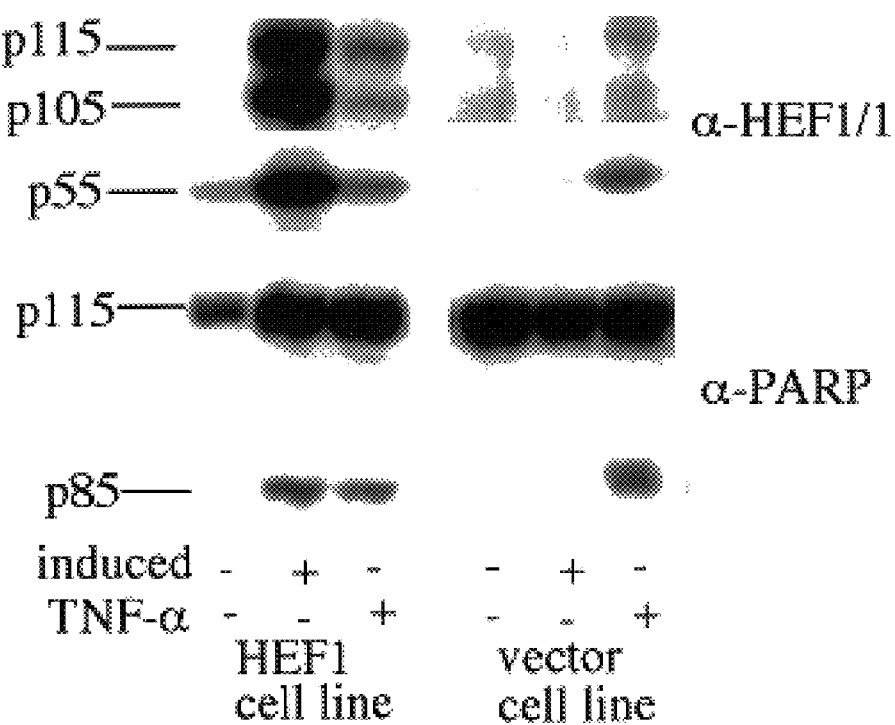
FIGS. 12A and 12B. A blot and a graph showing HEF1 expression causes protein cleavage and increased caspase activity.

Induction of HEF1 expression promotes apoptosis, while cleavage of endogenous HEF1 occurs following pro-apoptotic stimuli. Endogenous HEF1 exists during interphase as full length 105 kD and hyperphosphorylated 115 kD forms, localized primarily at focal adhesion sites. These endogenous full length forms are cleaved during mitosis, generating a 55 kD amino terminal form that localizes to the mitotic spindle (Law et al., (1998) Mol. Cell. Biol. 13: 3540–3551), while the carboxy-terminal end of the protein is apparently degraded. HEF1 transiently transfected into HeLa cells is cleaved in a non-cell cycle regulated manner at a predicted caspase 3/7 (DLVD) consensus site, producing a 55 kD amino-terminal peptide comparable in size to the mitotic p55 species (Law et al., (1998) Mol. Cell. Biol. 13: 3540–3551), and a 65 kD carboxy-terminal peptide. Significantly, careful inspection of transiently transfected populations suggested that cells expressing HEF1 appear to be dying, and HEF1-positive cells decrease in number at later times following transfection. These data raised the possibility that the overexpressed HEF1 protein might itself be promoting apoptosis and activating caspase function. If so, this would suggest that perturbation of HEF1-dependent signaling was a novel initiator of the cell death machinery. MCF-7 cell lines stably expressing HEF1 or parental vector under control of a tetracycline-regulatable promoter were already available (Example 2). To explore the role of HEF1 in apoptosis, it was initially determined whether the stable cell lines also showed signs of apoptosis upon HEF1 induction, and whether the cleavage of HEF1 and canonical caspase substrates is concomitantly activated. At 48 hours after induction of HEF1 expression, the majority (70%) of cells round up, become refractile, and float off the plate, a behavior consistent with cell death (FIG. 11, top). In contrast, uninduced cells and vector control cells appear normal with the majority of cells adherent and proliferating (FIG. 11, top, left hand panel, and bottom). At this time point, the full length HEF1, p105 and p115 species, as well as the HEF1 p55 kD cleavage product, are observed in induced HEF1 stable lines, but not in either the uninduced HEF1-containing lines or vector controls, except for endogenous HEF1 (FIG. 12A).

Figure 12B:
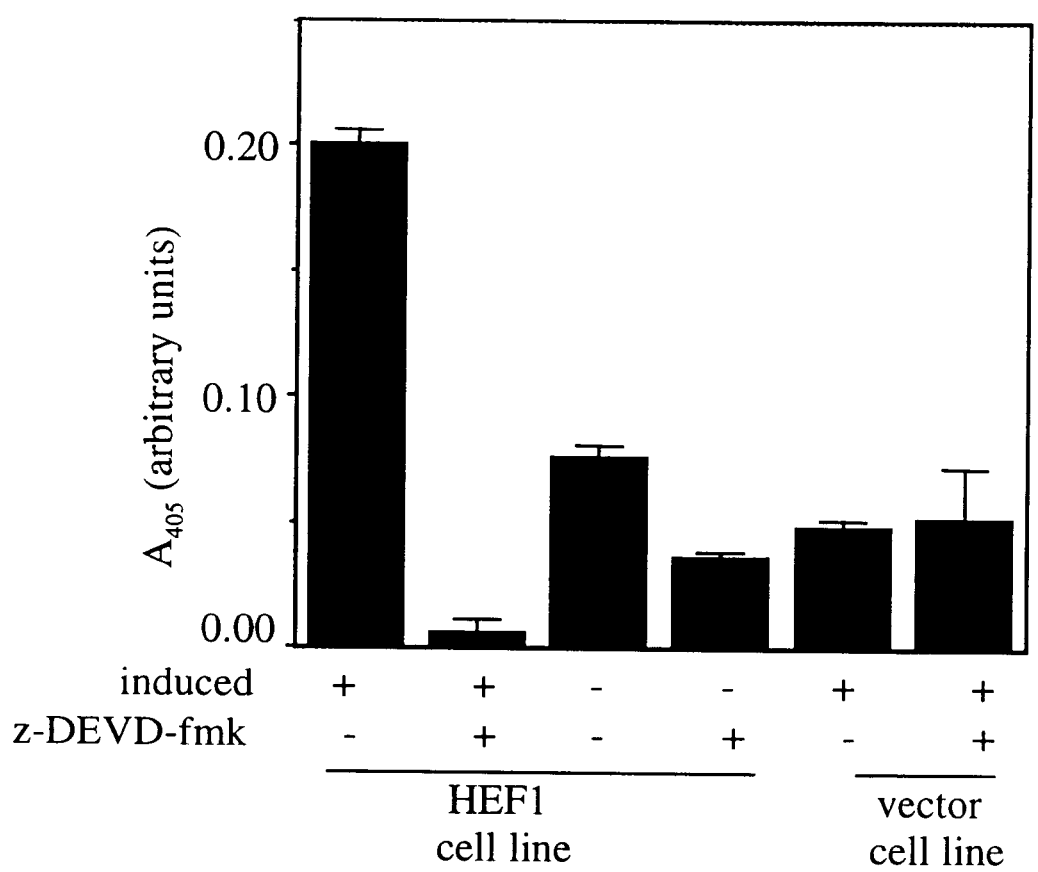

To determine if caspases were being activated by HEF1 expression, the cleavage of the known caspase-3 substrate (Lazebnik et al. (1994) Nature 371: 346–7; Boulares et al. (1999) Biol Chem 274: 22932–40) and apoptosis marker, Poly-ADP ribose polymerase (PARP) was assayed following HEF1 induction. As a positive control for PARP cleavage, uninduced HEF1 cells and vector control cells treated with TNF-α, a treatment previously shown to activate caspases and cause apoptosis in MCF-7 cells were included (Burow et al. (1998) Cancer Res 58: 4940–6). PARP cleavage was detected following either TNF-α treatment of HEF1 induction, but not in the uninduced and vector control cells (FIG. 12A). Notably, TNF-α treatment resulted in production of the 55 kD HEF1 cleavage product both in uninduced HEF1-containing and vector control lines, suggesting endogenous HEF1 was also cleaved. In addition, cells induced to express HEF1 exhibited enhanced cleavage of the colorimetric caspase 3 substrate Ac-DEVD-pNA. There is an approximately 2-fold increase in caspase activity as reflected by increased absorbance seen in the cells induced for HEF1 expression versus uninduced HEF1 cells and induced vector control cells (FIG. 12B). Further, activity towards the caspase 3 substrate in the HEF1 expressing cells is potently blocked by the inhibitory peptide z-DEVD-fmk (FIG. 12B), confirming the specificity of the cleavage.

Figure 13A:
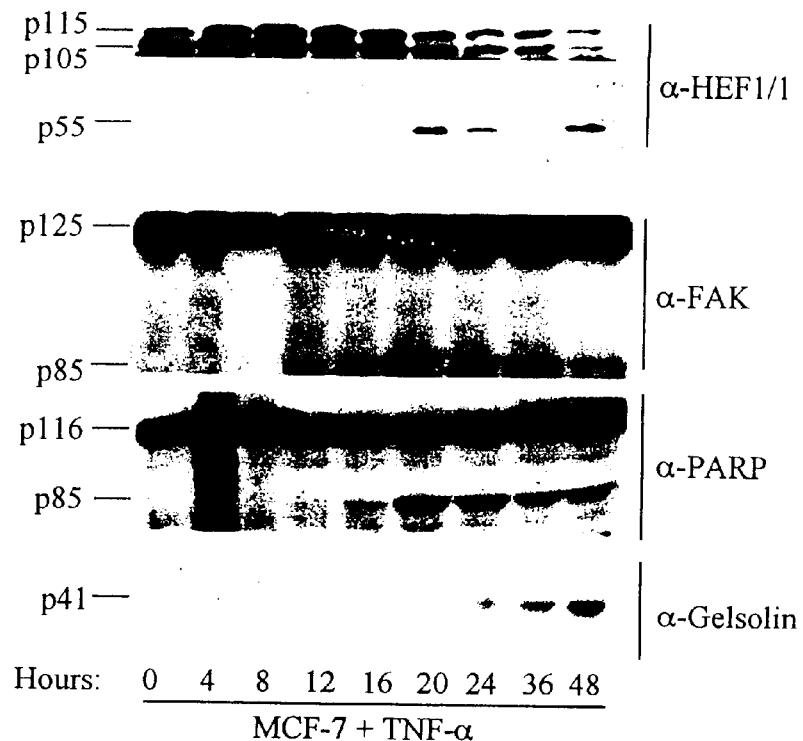
FIGS. 13A, 13B AND 13C. Endogenous MCF-7 HEF1 is cleaved by a caspase 3 like activity.
Figure 13B:
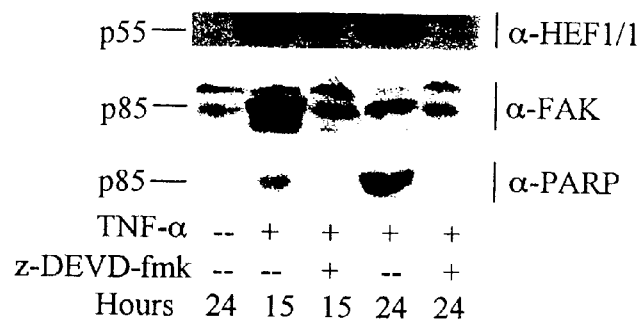
Figure 13C:
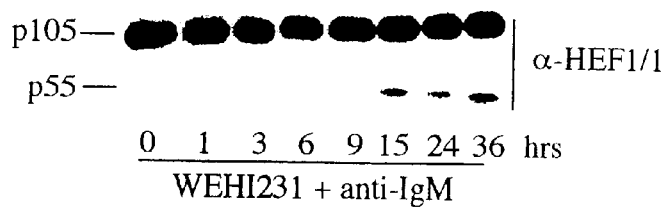

If HEF1 is a significant natural target for cleavage by caspases in apoptosis, then a time course of endogenous HEF1 cleavage should parallel that observed for other defined cytoskeletal and signaling proteins known to be cleaved following apototic stimulus. These include the HEF1 interactive partner FAK (Wen et al. (1997) J. Biol. Chem. 272: 26056–26061), the morphoregulatory kinase PAK (Rudel and Bokoch (1997) Science 276: 1571–4), the actin severing/capping protein gelsolin (Kothakota et al. (1997) Science 278: 294–8), and others (e.g. (Brancolini et al. (1995) EMBO J 14: 5179–90; Martin et al. (1995) J Biol Chem 270: 6425–8; Brancolini et al. (1997) J Cell Biol 139: 759–71; Browne et al. (1998) Cell Death Differ 5: 206–13)). The timing of endogenous HEF1 cleavage in response to TNF-α treatment was examined in parental MCF-7 cells. Approximately 16 hours after TNF-α addition, there is a decline in the 105/115 kD full length forms of HEF1 and an accumulation of the 55 kD amino terminal peptide (FIG. 13). For comparison, the cleavage of the caspase substrates FAK, PARP and gelsolin was analyzed. FAK and PARP cleavage coincide with the production of the 55 kD HEF1 form, whereas gelsolin cleavage is detected approximately 4 hours later (FIG. 13A). This suggested that HEF1 cleavage, like that of FAK and PARP, is an earlier event in the apoptotic process and may occur prior to changes in the cell cytoskeleton. The cell permeable caspase 3 inhibitory peptide z-DEVD-fmk inhibited generation of p85 FAK, p85 PARP, and the 55 kD HEF1 form at both 15 and 24 hours after TNF-α addition (FIG. 13B), confirming the caspase dependence of the cleavage events. Finally, HEF1 cleavage from full length to p55 was observed in an independent cell type, WeHI-231 B cells, in which apoptosis was induced by an entirely different stimulus, antibody crosslinking of surface IgM. This result indicated that the caspase targeting of HEF1 was not specific to MCF-7 cells and TNF-α treatment (FIG. 13C). In sum, these results indicate, that HEF1 expression in the absence of other inducing agents can induce caspase activation and cause apoptosis in MCF-7 cells. Furthermore, HEF1 cleavage is an early downstream event following apoptotic stimulation in multiple cell types.

Figure 14:
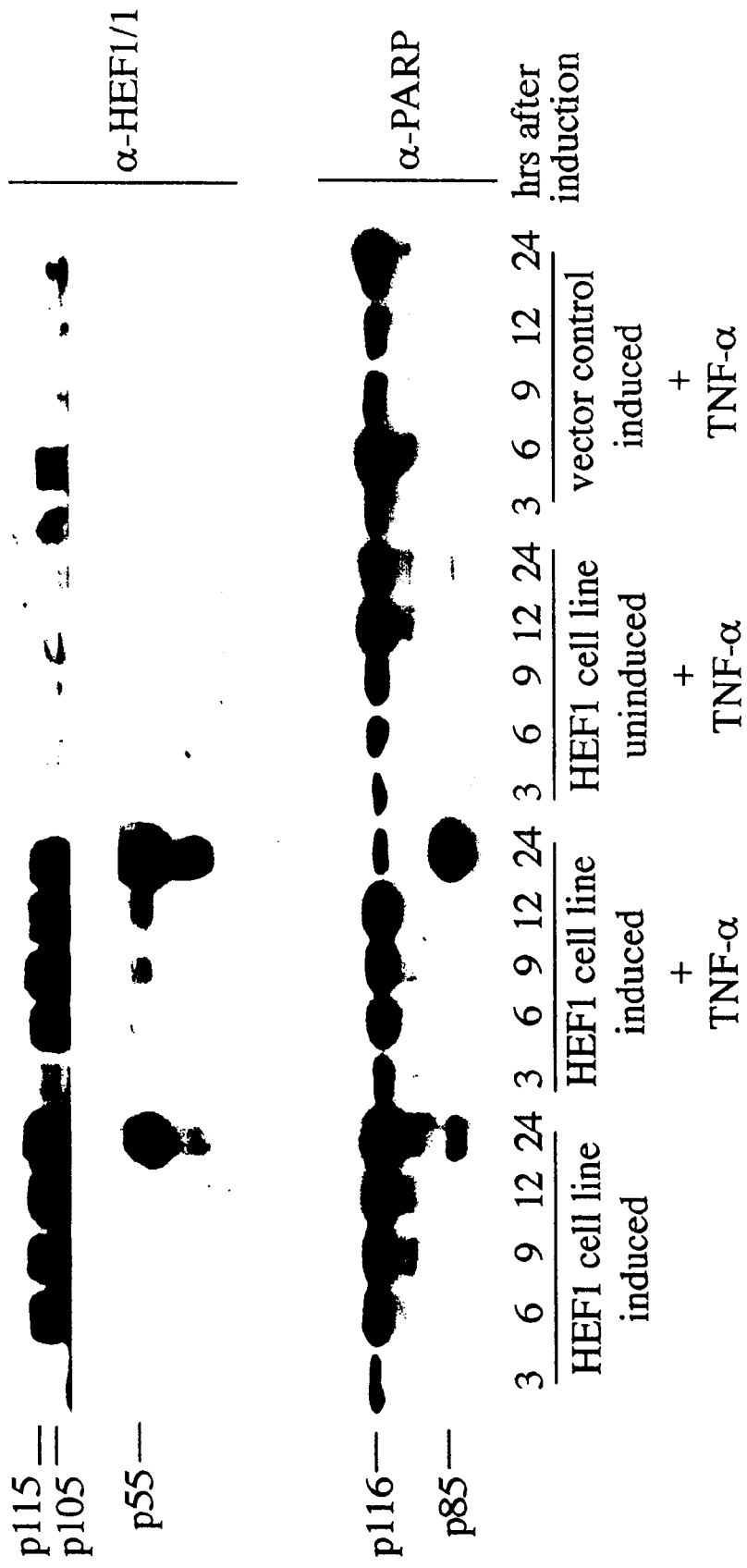
FIG. 14. Cell death induced by HEF1 expression is potentiated by TNF-α treatment. HEF1 stable transfectants were grown under inducing conditions, inducing conditions plus TNF-α and non-inducing conditions plus TNF-α. Vector control cells were grown under inducing conditions plus TNF-α. Western blots were probed with antibodies to HEF1 (α-HEF1/1) and to PARP (α-PARP).

Mechanistically, the fact that TNF-α and HEF1 induction both activate caspases can be explained by hypothesizing that HEF1 overexpression activates a pathway downstream of TNF-α, in which case, dual treatment would not have a greater effect than treatment with either TNF-α or HEF1 expression alone. Alternatively, HEF1 is activating a separate pathway. To address this point, experiments were performed to determined whether simultaneous overexpression of HEF1 and TNF-α treatment resulted in a more pronounced effect than either stimulus independently. On a gross morphological level, treatment with TNF-α alone resulted in a low level of cell rounding and death. In contrast, HEF1 induction together with TNF-α treatment led to essentially 100% cell death at 48 hours (FIG. 11, center panels). Cells were grown under inducing and non-inducing conditions with and without the addition of TNF-α as indicated, and cell lysates prepared and analyzed for HEF1 and PARP cleavage at the noted timepoints (FIG. 14). There is an increase in the degree of both HEF1 and PARP cleavage in cells induced to express HEF1 and treated with TNF-α. Control uninduced cells treated with TNF-α displayed significantly less PARP cleavage when compared with induced and induced plus TNF-α treated cells. This potentiation of cell death indicates that HEF1 expression may either prime the TNF-α death pathway or work synergistically to hasten apoptosis.

Figure 15A:
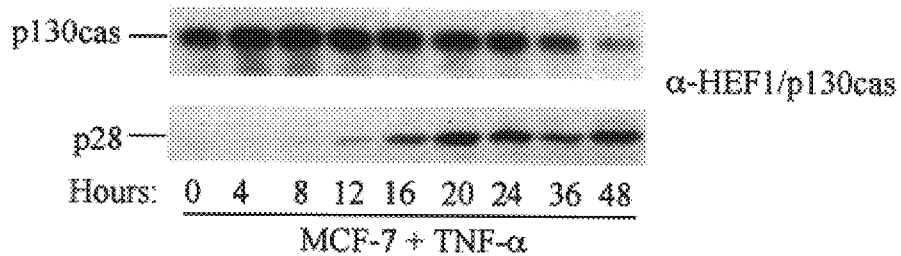
FIGS. 15A, 15B, 15C AND 15D. A 28 kD caspase cleavage product is generated from both HEF1 and p130cas.
Figure 15B:
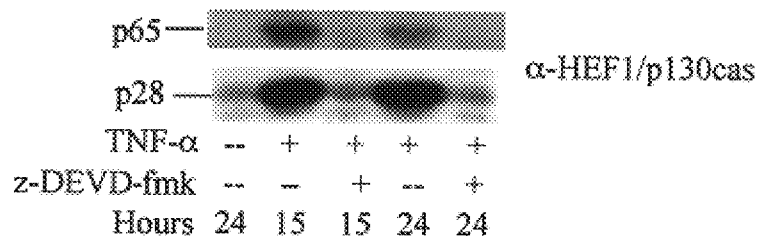
Figure 15C:
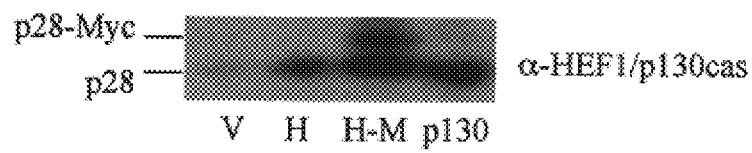
Figure 15D:
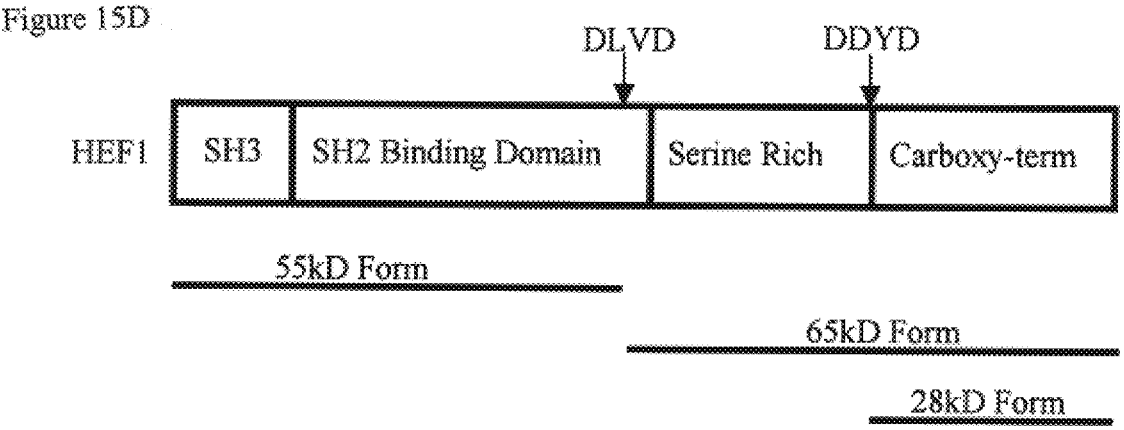

Carboxy-terminal HEF1 caspase cleavage products are differentially regulated by proteasomal degradation in mitosis and apoptosis. As previously noted, a p65 HEF1 carboxy-terminal cleavage product was readily identified following transient transfection of HEF1, a condition now defined as inducing apoptosis, but was not detectable in mitosis (Law et al. (1998) Mol. Cell. Biol. 13: 3540–3551). To probe the significance of this difference, the appearance of the lower molecular weight HEF1-derived species was examined over the time course during which p55 appeared following TNF-α stimulation of apoptosis (FIG. 15). For this purpose, antibodies were used that were specific for HEF1 at epitopes flanking the previously defined DLVD cleavage site. To scrutinize the extreme carboxy-terminal region of HEF1, it was necessary to use antibodies that cross-reacted with both HEF1 and p130cas, as antibodies specific for HEF1 are unavailable for this region. Concurrently, the production of the 65 kD carboxy-terminal peptide was assayed; however there was very little detectable p65 observed. This is possibly due to the unstable nature of this peptide. Surprisingly, during this analysis an additional immunoreactive protein with an estimated molecular mass of 28 kD appeared. The generation of this form begins at 12 hours followig TNF-α treatment of MCF-7 cells (FIG. 15A), paralleling the induction of the 55 kD species, and is inhibited by treatment with z-DEVD-fmk (FIG. 15B).

p130 Cas is cleaved in response to LPS treatment of epithelial cells (a pro-apoptotic stimulus) generating a 28 kD p130 Cas peptide (Bannerman et al. (1998) J Biol Chem 273: 35371–80). Since MCF-7 cells express both p130Cas and HEF1 and both proteins contain the anti-p130Cas epitope in their C-terminus, the observed p28 species may have been derived from either protein. To determine the origin of the p28 species, full-length HEF1 was carboxy-terminally tagged with the Myc epitope (HEF1-Mvc (H-M)), transfected into HeLa cells and compared with full length HEF1 (H), p130 Cas (p130), or empty vector (V) similarly transfected. Lysates from HEF1-Myc transfected cells have two anti-p130Cas immunoreactive bands (FIG. 15C). One band migrates at the same rate as the 28 kD protein observed in the HEF1- and p130Cas-transfected cells, and represents cleaved endogenous HEF1 and/or p130Cas. In contrast, the second band has a comparatively retarded electrophoretic mobility and corresponds to the 28 kD carboxy-terminal domain of HEF1 fused to the Myc-tag. Based on predicted molecular masses, potential caspase sites shared between HEF1 and p130 Cas, and the location of the anti-p130 Cas antibody epitope, a conserved DDYD motif is the likely candidate cleavage site (shown in FIG. 15D). These data indicate that at least some of the 28 kD form observed in MCF-7 cells is likely to be derived from HEF1.

Figure 16A:
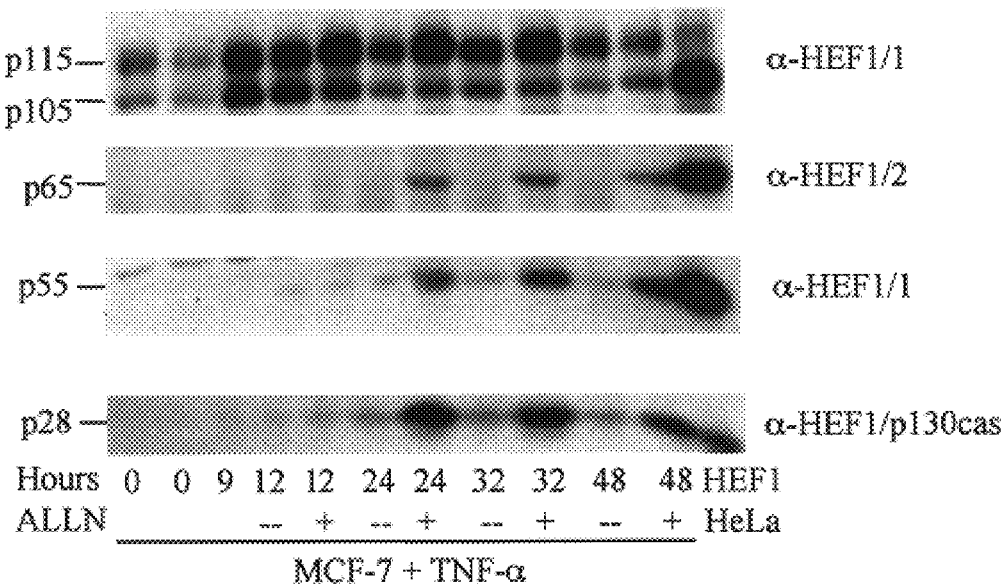
FIGS. 16A AND 16B. The stability of HEF1 and its cleavage products (65, 55. and 28 kD) is regulated by the proteosome.
Figure 16B:
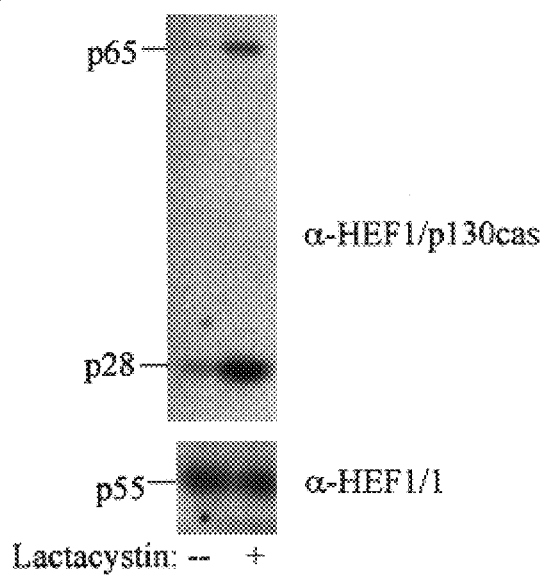

The above results indicate that caspases are required for processing of HEF1 to three distinct forms in apoptosis (p55, p65 and p28), but do not address differing abundance of the derivative species in apoptotic and mitotic cells. The possibility that levels of HEF1-derived peptides might additionally be regulated by proteasomal processing was investigated, as activity of the proteasome has been shown to be closely tied to caspase function (reviewed in (Orlowski (1999) Cell Death Differ 6: 303–13)). Addition of the calpain and proteosome inhibitor ALLN to MCF-7 cells treated with TNF-α led to a substantial increase in observed levels of the 65, 55, and 28 kD forms of HEF1, indicating that although these forms accumulate to levels higher than detected in normally dividing MCF-7 cells following TNF-α treatment, they are nevertheless being actively degraded (FIG. 15A). Similar results were obtained with a less potent analog of ALLN, ALLM, as well as the specific proteosome inhibitor lactacystin. In contrast, in a synchronized population of mitotic MCF-7 cells, the addition of lactacystin induced a marked increase in the 65 and 28 kD HEF1 forms compared to untreated cells, while the amount of the 55 kD form remained unchanged (FIG. 16). These results indicate, firstly, that the abundance of the HEF1 forms is controlled not only by caspases but also through degradation via the proteasome, and secondly, that the p55 form is subject to proteasomal degradation during apoptosis, but not mitosis.

Figure 17:
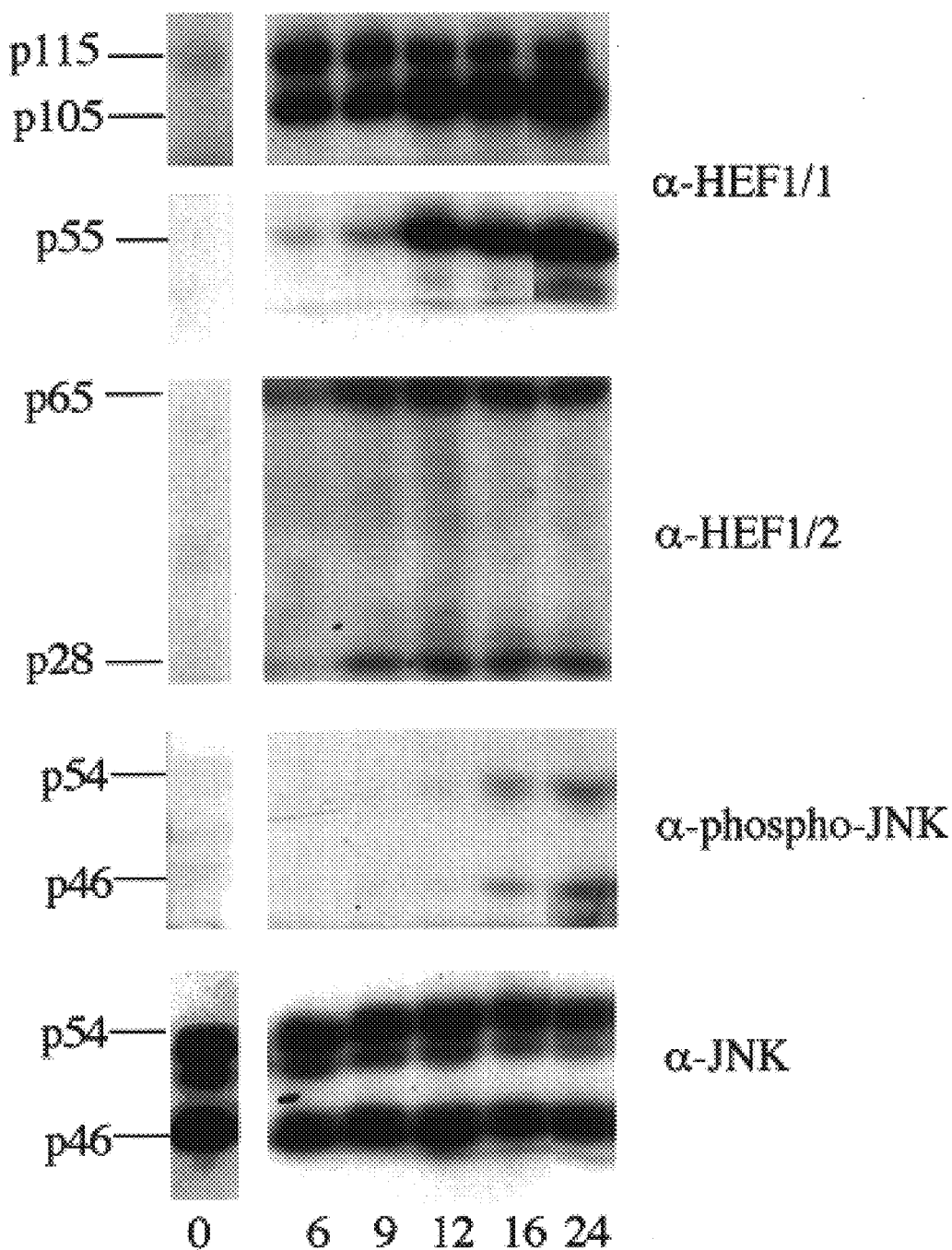
FIG. 17. HEF1 overexpression causes increased phospho-JNK levels. HEF1 cells were induced for HEF1 expression and total proteins extracted at the times indicated. Western blots of total proteins were probed with antibodies to HEF1(α HEF1/1and α HEF1/p130 Cas), anti-phospho-JNK antibodies (α-phospho-JNK) and to indicate equivalent loading of total proteins, blots were then probed with antibodies to JNK.

HEF1 induces activation of JNK signaling. The HEF1 family member p130Cas associates with the adaptor protein Crk to couple extracellular stimuli to activation of the JNK pathway (Dolfi et al. (1998) Proc. Natl. Acad. Sci. USA 955: 15394–9; Blaukat et al. (1999) J Biol Chem 274: 14893–901). In light of the previously reported association between HEF1 and Crk (Minegishi et al. (1996) J. Exp. Med. 184: 1365–1375; Manie et al (1997) J. Biol. Chem. 272: 4230–4236), and the putative role for JNK in apoptosis (reviewed in (Ip and Davis (1998) Curr Opin. Cell Biol. 10: 205–219)), JNK phosphorylation in HEF1 stable cell lines was examined using antibodies that recognize phosphorylated (activated) JNK I and JNK2. Full length 105/115 kD HEF1 is abundant by 6 hours after induction, with the accumulation of the p65, p55, and p28 cleavage products first noticeable at 9–12 hours (FIG. 17). JNK1 and JNK2 are phosphorylated and activated around 16 hours after induction of HEF1 expression, but not in the uninduced HEF1 cell lines nor in vector expressing control cell lines. Western blots of cell lysates were probed with antibodies to JNK demonstrating that there is approximately equivalent total JNK levels in all of the cell. extracts (FIG. 17). The observation that formation of the HEF1 cleavage products appears to precede JNK phosphorylation/activation suggests that these cleavage events may be associated with JNK activation and in turn may be a contributing factor to HEF1 induction of apoptosis.

The present invention is not limited to the embodiments specifically described above, but is capable of variation and modification without departure from the scope of the appended claims.

What is claimed is:

1. A method for detecting a germline alteration in a HEF1 gene in a human, said method comprising comparing a sequence selected from the group consisting of a HEF1 gene, HEF1 RNA from a human sample, and a sequence of cDNA made from mRNA from said human sample with a wild-type HEF1 nucleic acid sequence.

2. The method of claim 1 which comprises analyzing HEF1 RNA from the human.

3. A method for detecting a somatic cell nucleic acid alteration in a HEF1 gene in a human, said method comprising comparing a sequence selected from the group consisting of a HEF1 gene, HEF1 RNA from a human sample, and a sequence of cDNA made from mRNA from said human sample from said somatic cell with a wild-type HEF1 sequence.

4. The method of claim 1 which comprises analyzing HEF1 RNA isolated from somatic cells of the human.

* * * * *

```
                           SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
           (A) LENGTH: 3672 base pairs
           (B) TYPE: nucleic acid
           (C) STRANDEDNESS: single
           (D) TOPOLOGY: not relevant (ii) MOLECULE TYPE: DNA (cDNA)

(iii) HYPOTHETICAL: NO (iv) ANTI-SENSE: NO (xi) SEQUENCE DESCRIPTION: SEQ ID NO: 1:

ACCCCCACGC TACCGAAATG AAGTATAAGA ATCTTATGGC AAGGGCCTTA TATGACAATG      60

TCCCAGAGTG TGCCGAGGAA CTGGCCTTTC GCAAGGGAGA CATCCTGACC GTCATAGAGC    120

AGAACACAGG GGGACTGGAA GGATGGTGGC TGTGCTCGTT ACACGGTCGG CAAGGCATTG    180

TCCCAGGCAA CCGGGTGAAG CTTCTGATTG CCCCATGCA GGAGACTGCC TCCAGTCACG     240

AGCAGCCTGC CTCTGGACTG ATGCAGCAGA CCTTTGGCCA ACAGAAGCTC TATCAAGTGC    300

CAAACCCACA GGCTGCTCCC CGAGACACTA TCTACCAAGT GCCACCTTCC TACCAAAATC    360

AGGGAATTTA CCAAGTCCCC ACTGGCCACG GCACCCAAGA ACAAGAGGTA TATCAGGTGC    420

CACCATCAGT GCAGAGAAGC ATTGGGGGAA CCAGTGGGCC CCACGTGGGT AAAAAGGTGA    480

TAACCCCCGT GAGGACAGGC CATGGCTACG TATACGAGTA CCCATCCAGA TACCAAAAGG    540

ATGTCTATGA TATCCCTCCT TCTCATACCA CTCAAGGGGT ATACGACATC CCTCCCTCAT    600

CAGCAAAAGG CCCTGTGTTT TCAGTTCCAG TGGGAGAGAT AAAACCTCAA GGGGTGTATG    660

ACATCCCGCC TACAAAAGGG GTATATGCCA TTCCGCCCTC TGCTTGCCGG GATGAAGCAG    720

GGCTTAGGGA AAAAGACTAT GACTTCCCCC CTCCCATGAG ACAAGCTGGA AGGCCGGACC    780

TCAGACCGGA GGGGGTTTAT GACATTCCTC CAACCTGCAC CAAGCCAGCA GGGAAGGACC    840

TTCATGTAAA ATACAACTGT GACATTCCAG GAGCTGCAGA ACCGGTGGCT CGAAGGCACC    900

AGAGCCTGTC CCCGAATCAC CCACCCCCGC AACTCGGACA GTCAGTGGGC TCTCAGAACG    960

ACGCATATGA TGTCCCCCGA GGCGTTCAGT TTCTTGAGCC ACCAGCAGAA ACCAGTGAGA   1020

AAGCAAACCC CCAGGAAAGG GATGGTGTTT ATGATGTCCC TCTGCATAAC CCGCCAGATG   1080

CTAAAGGCTC TCGGGACTTG GTGGATGGGA TCAACCGATT GTCTTTCTCC AGTACAGGCA   1140

GCACCCGGAG TAACATGTCC ACGTCTTCCA CCTCCTCCAA GGAGTCCTCA CTGTCAGCCT   1200

CCCCAGCTCA GGACAAAAGG CTCTTCCTGG ATCCAGACAC AGCTATTGAG AGACTTCAGC   1260

GGCTCCAGCA GGCCCTTGAG ATGGGTGTCT CCAGCCTAAT GGCACTGGTC ACTACCGACT   1320

GGCGGTGTTA CGGATATATG GAAAGACACA TCAATGAAAT ACGCACAGCA GTGGACAAGG   1380

TGGAGCTGTT CCTGAAGGAG TACCTCCACT TTGTCAAGGG AGCTGTTGCA AATGCTGCCT   1440

GCCTCCCGGA ACTCATCCTC CACAACAAGA TGAAGCGGGA GCTGCAACGA GTCGAAGACT   1500

CCCACCAGAT CCTGAGTCAA ACCAGCCATG ACTTAAATGA GTGCAGCTGG TCCCTGAATA   1560
```

-continued

```
TCTTGGCCAT CAACAAGCCC CAGAACAAGT GTGACGATCT GGACCGGTTT GTGATGGTGG      1620

CAAAGACGGT GCCCGATGAC GCCAAGCAGC TCACCACAAC CATCAACACC AACGCAGAGG      1680

CCCTCTTCAG ACCCGGCCCT GGCAGCTTGC ATCTGAAGAA TGGGCCGGAG AGCATCATGA      1740

ACTCAACGGA GTACCCACAC GGTGGCTCCC AGGGACAGCT GCTGCATCCT GGTGACCACA      1800

AGGCCCAGGC CCACAACAAG GCACTGCCCC CAGGCCTGAG CAAGGAGCAG GCCCCTGACT      1860

GTAGCAGCAG TGATGGTTCT GAGAGGAGCT GGATGGATGA CTACGATTAC GTCCACCTAC      1920

AGGGTAAGGA GGAGTTTGAG AGGCAACAGA AAGAGCTATT GGAAAAAGAG AATATCATGA      1980

AACAGAACAA GATGCAGCTG GAACATCATC AGCTGAGCCA GTTCCAGCTG TTGGAACAAG      2040

AGATTACAAA GCCCGTGGAG AATGACATCT CGAAGTGGAA GCCCTCTCAG AGCCTACCCA      2100

CCACAAACAG TGGCGTGAGT GCTCAGGATC GGCAGTTGCT GTGCTTCTAC TATGACCAAT      2160

GTGAGACCCA TTTCATTTCC CTTCTCAACG CCATTGACGC ACTCTTCAGT TGTGTCAGCT      2220

CAGCCCAGCC CCCGCGAATC TTCGTGGCAC ACAGCAAGTT TGTCATCCTC AGTGCACACA      2280

AACTGGTGTT CATTGGAGAC ACGCTGACAC GGCAGGTGAC TGCCCAGGAC ATTCGCAACA      2340

AAGTCATGAA CTCCAGCAAC CAGCTCTGCG AGCAGCTCAA GACTATAGTC ATGGCAACCA      2400

AGATGGCCGC CCTCCATTAC CCCAGCACCA CGGCCCTGCA GGAAATGGTG CACCAAGTGA      2460

CAGACCTTTC TAGAAATGCC CAGCTGTTCA AGCGCTCTTT GCTGGAGATG CAACGTTCT       2520

GAGAAGAAAA AAAAGAGGAA GGGGACTGCG TTAACGGTTA CTAAGGAAAA CTGGAAATAC      2580

TGTCTGGTTT TTGTAAATGT TATCTATTTT TGTAGATAAT TTTATATAAA AATGAAATAT      2640

TTTAACATTT TATGGGTCAG ACAACTTTCA GAAATTCAGG GAGCTGGAGA GGGAAATCTT      2700

TTTTTCCCCC CTGAGTNGTT CTTATGTATA CACAGAAGTA TCTGAGACAT AAACTGTACA      2760

GAAAACTTGT CCACGTCCTT TTGTATGCCC ATGTATTCAT GTTTTTGTTT GTAGATGTTT      2820

GTCTGATGCA TTTCATTAAA AAAAAAACCA TGAATTACGA AGCACCTTAG TAAGCACCTT      2880

CTAATGCTGC ATTTTTTTTG TTGTTGTTAA AAACATCCAG CTGGTTATAA TATTGTTCTC      2940

CACGTCCTTG TGATGATTCT GAGCCTGGCA CTGGGAATCT GGGAAGCATA GTTTATTTGC      3000

AAGTGTTCAC CTTCCAAATC ATGAGGCATA GCATGACTTA TTCTTGTTTT GAAAACTCTT      3060

TTCAAAACTG ACCATCTTAA ACACATGATG GCCAAGTGCC ACAAAGCCCT CTTGCGGAGA      3120

CATTTACGAA TATATATGTG GATCCAAGTC TCGATAGTTA GGCGTTGGAG GGAAGAGAGA      3180

CCAGAGAGTT TAGAGGCCAG GACCACAGTT AGGATTGGGT TGTTTCAATA CTGAGAGACA      3240

GCTACAATAA AAGGAGAGCA ATTGCCTCCC TGGGGCTGTT CAATCTTCTG CATTTGTGAG      3300

TGGTTCAGTC ATGAGGTTTT CCAAAAGATG TTTTTAGAGT TGTAAAAACC ATATTTGCAG      3360

CAAAGATTTA CAAAGGCGTA TCAGACTATG ATTGTTCACC AAAATAGGGG AATGGTTTGA      3420

TCCGCCAGTT GCAAGTAGAG GCCTTTCTGA CTCTTAATAT TCACTTTGGT GCTACTACCC      3480

CCATTACCTG AGGAACTGGC CAGGTCCTTG ATCATGGAAC TATAGAGCTA CCAGACATAT      3540

CCTGCTCTCT AAGGGAATTT ATTGCTATCT TGCACCTTCT TTAAAACTCA AAAACATAT       3600

GCAGACCTGA CACTCAAGAG TGGCTAGCTA CACAGAGTCC ATCTAATTTT TGCAACTTCC      3660

CCCCCCGAAT TC                                                         3672
```

(2) INFORMATION FOR SEQ ID NO: 2:

(i) SEQUENCE CHARACTERISTICS:
        (A) LENGTH: 834 amino acids
        (B) TYPE: amino acid

```
        (C) STRANDEDNESS: not relevant
        (D) TOPOLOGY: not relevant (ii) MOLECULE TYPE: protein (iii) HYPOTHETICAL: NO (iv) ANTI-SENSE: NO (xi) SEQUENCE DESCRIPTION: SEQ ID NO: 2:

Met Lys Tyr Lys Asn Leu Met Ala Arg Ala Leu Tyr Asp Asn Val Pro
1               5                  10                  15

Glu Cys Ala Glu Glu Leu Ala Phe Arg Lys Gly Asp Ile Leu Thr Val
            20                  25                  30

Ile Glu Gln Asn Thr Gly Gly Leu Glu Gly Trp Trp Leu Cys Ser Leu
        35                  40                  45

His Gly Arg Gln Gly Ile Val Pro Gly Asn Arg Val Lys Leu Leu Ile
    50                  55                  60

Gly Pro Met Gln Glu Thr Ala Ser Ser His Glu Gln Pro Ala Ser Gly
65                  70                  75                  80

Leu Met Gln Gln Thr Phe Gly Gln Gln Lys Leu Tyr Gln Val Pro Asn
                85                  90                  95

Pro Gln Ala Ala Pro Arg Asp Thr Ile Tyr Gln Val Pro Pro Ser Tyr
            100                 105                 110

Gln Asn Gln Gly Ile Tyr Gln Val Pro Thr Gly His Gly Thr Gln Glu
        115                 120                 125

Gln Glu Val Tyr Gln Val Pro Pro Ser Val Gln Arg Ser Ile Gly Gly
    130                 135                 140

Thr Ser Gly Pro His Val Gly Lys Lys Val Ile Thr Pro Val Arg Thr
145                 150                 155                 160

Gly His Gly Tyr Val Tyr Glu Tyr Pro Ser Arg Tyr Gln Lys Asp Val
                165                 170                 175

Tyr Asp Ile Pro Pro Ser His Thr Thr Gln Gly Val Tyr Asp Ile Pro
            180                 185                 190

Pro Ser Ser Ala Lys Gly Pro Val Phe Ser Val Pro Val Gly Glu Ile
        195                 200                 205

Lys Pro Gln Gly Val Tyr Asp Ile Pro Pro Thr Lys Gly Val Tyr Ala
    210                 215                 220

Ile Pro Pro Ser Ala Cys Arg Asp Glu Ala Gly Leu Arg Glu Lys Asp
225                 230                 235                 240

Tyr Asp Phe Pro Pro Pro Met Arg Gln Ala Gly Arg Pro Asp Leu Arg
                245                 250                 255

Pro Glu Gly Val Tyr Asp Ile Pro Pro Thr Cys Thr Lys Pro Ala Gly
            260                 265                 270

Lys Asp Leu His Val Lys Tyr Asn Cys Asp Ile Pro Gly Ala Ala Glu
        275                 280                 285

Pro Val Ala Arg Arg His Gln Ser Leu Ser Pro Asn His Pro Pro Pro
    290                 295                 300

Gln Leu Gly Gln Ser Val Gly Ser Gln Asn Ala Tyr Asp Val Pro
305                 310                 315                 320

Arg Gly Val Gln Phe Leu Glu Pro Pro Ala Glu Thr Ser Glu Lys Ala
                325                 330                 335

Asn Pro Gln Glu Arg Asp Gly Val Tyr Asp Val Pro Leu His Asn Pro
            340                 345                 350

Pro Asp Ala Lys Gly Ser Arg Asp Leu Val Asp Gly Ile Asn Arg Leu
        355                 360                 365
```

```
Ser Phe Ser Ser Thr Gly Ser Thr Arg Ser Asn Met Ser Thr Ser Ser
    370                 375                 380
Thr Ser Ser Lys Glu Ser Ser Leu Ser Ala Ser Pro Ala Gln Asp Lys
385                 390                 395                 400
Arg Leu Phe Leu Asp Pro Asp Thr Ala Ile Glu Arg Leu Gln Arg Leu
                405                 410                 415
Gln Gln Ala Leu Glu Met Gly Val Ser Ser Leu Met Ala Leu Val Thr
                420                 425                 430
Thr Asp Trp Arg Cys Tyr Gly Tyr Met Glu Arg His Ile Asn Glu Ile
                435                 440                 445
Arg Thr Ala Val Asp Lys Val Glu Leu Phe Leu Lys Glu Tyr Leu His
    450                 455                 460
Phe Val Lys Gly Ala Val Ala Asn Ala Ala Cys Leu Pro Glu Leu Ile
465                 470                 475                 480
Leu His Asn Lys Met Lys Arg Glu Leu Gln Arg Val Glu Asp Ser His
                485                 490                 495
Gln Ile Leu Ser Gln Thr Ser His Asp Leu Asn Glu Cys Ser Trp Ser
                500                 505                 510
Leu Asn Ile Leu Ala Ile Asn Lys Pro Gln Asn Lys Cys Asp Asp Leu
    515                 520                 525
Asp Arg Phe Val Met Val Ala Lys Thr Val Pro Asp Asp Ala Lys Gln
    530                 535                 540
Leu Thr Thr Thr Ile Asn Thr Asn Ala Glu Ala Leu Phe Arg Pro Gly
545                 550                 555                 560
Pro Gly Ser Leu His Leu Lys Asn Gly Pro Glu Ser Ile Met Asn Ser
                565                 570                 575
Thr Glu Tyr Pro His Gly Gly Ser Gln Gly Gln Leu Leu His Pro Gly
                580                 585                 590
Asp His Lys Ala Gln Ala His Asn Lys Ala Leu Pro Pro Gly Leu Ser
                595                 600                 605
Lys Glu Gln Ala Pro Asp Cys Ser Ser Ser Asp Gly Ser Glu Arg Ser
    610                 615                 620
Trp Met Asp Asp Tyr Asp Tyr Val His Leu Gln Gly Lys Glu Glu Phe
625                 630                 635                 640
Glu Arg Gln Gln Lys Glu Leu Leu Glu Lys Glu Asn Ile Met Lys Gln
                645                 650                 655
Asn Lys Met Gln Leu Glu His His Gln Leu Ser Gln Phe Gln Leu Leu
                660                 665                 670
Glu Gln Glu Ile Thr Lys Pro Val Glu Asn Asp Ile Ser Lys Trp Lys
                675                 680                 685
Pro Ser Gln Ser Leu Pro Thr Thr Asn Ser Gly Val Ser Ala Gln Asp
690                 695                 700
Arg Gln Leu Leu Cys Phe Tyr Tyr Asp Gln Cys Glu Thr His Phe Ile
705                 710                 715                 720
Ser Leu Leu Asn Ala Ile Asp Ala Leu Phe Ser Cys Val Ser Ser Ala
                725                 730                 735
Gln Pro Pro Arg Ile Phe Val Ala His Ser Lys Phe Val Ile Leu Ser
                740                 745                 750
Ala His Lys Leu Val Phe Ile Gly Asp Thr Leu Thr Arg Gln Val Thr
    755                 760                 765
Ala Gln Asp Ile Arg Asn Lys Val Met Asn Ser Ser Asn Gln Leu Cys
    770                 775                 780
```

-continued

```
Glu Gln Leu Lys Thr Ile Val Met Ala Thr Lys Met Ala Ala Leu His
785                 790                 795                 800

Tyr Pro Ser Thr Thr Ala Leu Gln Glu Met Val His Gln Val Thr Asp
                805                 810                 815

Leu Ser Arg Asn Ala Gln Leu Phe Lys Arg Ser Leu Leu Glu Met Ala
                820                 825                 830

Thr Phe
```

(2) INFORMATION FOR SEQ ID NO: 3:

(i) SEQUENCE CHARACTERISTICS:
        (A) LENGTH: 872 amino acids
        (B) TYPE: amino acid
        (C) STRANDEDNESS: not relevant
        (D) TOPOLOGY: not relevant (ii) MOLECULE TYPE: protein (iii) HYPOTHETICAL: NO (iv) ANTI-SENSE: NO (xi) SEQUENCE DESCRIPTION: SEQ ID NO: 3:

```
Met Lys Tyr Leu Asn Val Leu Ala Lys Ala Leu Tyr Asp Asn Val Ala
1               5                   10                  15

Glu Ser Pro Asp Glu Leu Ser Phe Arg Lys Gly Asp Ile Met Thr Val
                20                  25                  30

Glu Arg Asp Thr Gln Gly Leu Asp Gly Trp Trp Leu Cys Ser Leu His
                35                  40                  45

Gly Arg Gln Gly Ile Val Pro Gly Asn Arg Leu Lys Ile Leu Val Gly
50                  55                  60

Met Tyr Asp Lys Lys Pro Ala Ala Pro Gly Pro Gly Pro Pro Ala Thr
65                  70                  75                  80

Pro Pro Gln Pro Gln Pro Ser Leu Pro Gln Gly Val His Thr Pro Val
                85                  90                  95

Pro Pro Ala Ser Gln Tyr Ser Pro Met Leu Pro Thr Ala Tyr Gln Pro
                100                 105                 110

Gln Pro Asp Asn Val Tyr Leu Val Pro Thr Pro Ser Lys Thr Gln Gln
                115                 120                 125

Gly Leu Tyr Gln Ala Pro Gly Asn Pro Gln Phe Gln Ser Pro Pro Ala
                130                 135                 140

Lys Gln Thr Ser Thr Phe Ser Lys Gln Thr Pro His His Ser Phe Pro
145                 150                 155                 160

Ser Pro Ala Thr Asp Leu Tyr Gln Val Pro Pro Gly Pro Gly Ser Pro
                165                 170                 175

Ala Gln Asp Ile Tyr Gln Val Pro Pro Ser Ala Gly Thr Gly His Asp
                180                 185                 190

Ile Tyr Gln Val Pro Pro Ser Leu Asp Thr Arg Ser Trp Glu Gly Thr
                195                 200                 205

Lys Pro Pro Ala Lys Val Val Val Pro Thr Arg Val Gly Gln Gly Tyr
                210                 215                 220

Val Tyr Glu Ala Ser Gln Ala Glu Gln Asp Glu Tyr Asp Thr Pro Arg
225                 230                 235                 240

His Leu Leu Ala Pro Gly Ser Gln Asp Ile Tyr Asp Val Pro Pro Val
                245                 250                 255

Arg Gly Leu Leu Pro Asn Gln Tyr Gly Gln Glu Val Tyr Asp Thr Pro
                260                 265                 270
```

```
Pro Met Ala Val Lys Gly Pro Asn Gly Arg Asp Pro Leu Leu Asp Val
        275                 280                 285

Tyr Asp Val Pro Pro Ser Val Glu Lys Gly Leu Pro Pro Ser Asn His
        290                 295                 300

His Ser Val Tyr Asp Val Pro Pro Ser Val Ser Lys Asp Val Pro Asp
305                 310                 315                 320

Gly Pro Leu Leu Arg Glu Glu Thr Tyr Asp Val Pro Pro Ala Phe Ala
                325                 330                 335

Lys Pro Lys Pro Phe Asp Pro Thr Arg His Pro Leu Ile Leu Ala Ala
                340                 345                 350

Pro Pro Pro Asp Ser Pro Pro Ala Glu Asp Val Tyr Asp Val Pro Pro
                355                 360                 365

Pro Ala Pro Asp Leu Tyr Asp Val Pro Pro Gly Leu Arg Arg Pro Gly
        370                 375                 380

Pro Gly Thr Leu Tyr Asp Val Pro Arg Glu Arg Val Leu Pro Pro Glu
385                 390                 395                 400

Val Ala Asp Gly Ser Val Ile Asp Asp Gly Val Tyr Ala Val Pro Pro
                405                 410                 415

Pro Ala Glu Arg Glu Ala Pro Thr Asp Gly Lys Arg Leu Ser Ala Ser
                420                 425                 430

Ser Thr Gly Ser Thr Arg Ser Ser Gln Ser Ala Ser Ser Leu Glu Val
        435                 440                 445

Val Val Pro Gly Arg Glu Pro Leu Glu Leu Glu Val Ala Val Glu Thr
        450                 455                 460

Leu Ala Arg Leu Gln Gln Gly Val Ser Thr Thr Val Ala His Leu Leu
465                 470                 475                 480

Asp Leu Val Gly Ser Ala Ser Gly Pro Gly Gly Trp Arg Ser Thr Ser
                485                 490                 495

Glu Pro Gln Glu Pro Pro Val Gln Asp Leu Lys Ala Ala Val Ala Ala
                500                 505                 510

Val His Gly Ala Val His Glu Leu Leu Glu Phe Ala Arg Ser Ala Val
        515                 520                 525

Ser Ser Ala Thr His Thr Ser Asp Arg Thr Leu His Ala Lys Leu Ser
530                 535                 540

Arg Gln Leu Gln Lys Met Glu Asp Val Tyr Gln Thr Leu Val Val His
545                 550                 555                 560

Gly Gln Val Leu Asp Ser Gly Arg Gly Gly Pro Gly Phe Thr Leu Asp
                565                 570                 575

Asp Leu Asp Thr Leu Val Ala Cys Ser Arg Ala Val Pro Glu Asp Ala
                580                 585                 590

Lys Gln Leu Ala Ser Phe Leu His Gly Asn Ala Ser Leu Leu Phe Arg
        595                 600                 605

Arg Thr Lys Ala Pro Gly Pro Gly Pro Glu Gly Ser Ser Leu His
610                 615                 620

Leu Asn Pro Thr Asp Lys Ala Ser Ser Ile Gln Ser Arg Pro Leu Pro
625                 630                 635                 640

Ser Pro Pro Lys Phe Thr Ser Gln Asp Ser Pro Asp Gly Gln Tyr Glu
                645                 650                 655

Asn Ser Glu Gly Gly Trp Met Glu Asp Tyr Asp Tyr Val His Leu Gln
                660                 665                 670

Gly Lys Glu Glu Phe Glu Lys Thr Gln Lys Glu Leu Leu Glu Lys Gly
        675                 680                 685

Asn Ile Val Arg Gln Gly Lys Gly Gln Leu Glu Leu Gln Gln Leu Lys
```

-continued

```
            690                 695                 700
Gln Phe Glu Arg Leu Glu Gln Glu Val Ser Arg Pro Ile Asp His Asp
705                 710                 715                 720

Leu Ala Asn Trp Thr Pro Ala Gln Pro Leu Val Pro Gly Arg Thr Gly
                725                 730                 735

Gly Leu Gly Pro Ser Asp Arg Gln Leu Leu Leu Phe Tyr Leu Glu Gln
                740                 745                 750

Cys Glu Ala Asn Leu Thr Thr Leu Thr Asp Ala Val Asp Ala Phe Phe
                755                 760                 765

Thr Ala Val Ala Thr Asn Gln Pro Pro Lys Ile Phe Val Ala His Ser
770                 775                 780

Lys Phe Val Ile Leu Ser Ala His Lys Leu Val Phe Ile Gly Asp Thr
785                 790                 795                 800

Leu Ser Arg Gln Ala Lys Ala Ala Asp Val Arg Ser Lys Val Thr His
                805                 810                 815

Tyr Ser Asn Leu Leu Cys Asp Leu Leu Arg Gly Ile Val Ala Thr Thr
                820                 825                 830

Lys Ala Ala Leu Gln Tyr Pro Ser Pro Ser Ala Ala Gln Asp Met
                835                 840                 845

Val Asp Arg Val Lys Glu Leu Gly His Ser Thr Gln Gln Phe Arg Arg
850                 855                 860

Val Leu Gly Gln Leu Ala Ala Ala
865                 870
```

(2) INFORMATION FOR SEQ ID NO: 4:

(i) SEQUENCE CHARACTERISTICS:
        (A) LENGTH: 78 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 4:

```
Leu Ser Gln Phe Gln Leu Leu Glu Gln Glu Ile Thr Lys Pro Val Glu
1               5                   10                  15

Asn Asp Ile Ser Lys Trp Lys Pro Ser Gln Ser Leu Pro Thr Thr Asn
                20                  25                  30

Asn Ser Val Gly Ala Gln Asp Arg Gln Leu Leu Cys Phe Tyr Tyr Asp
                35                  40                  45

Gln Cys Glu Thr His Phe Ile Ser Leu Leu Asn Ala Ile Asp Ala Leu
                50                  55                  60

Phe Ser Cys Val Ser Ser Ala Gln Pro Pro Arg Ile Phe Val
65                  70                  75
```